United States Patent
Ohtake et al.

(10) Patent No.: US 7,834,182 B2
(45) Date of Patent: Nov. 16, 2010

(54) PIPERIDINE DERIVATIVE

(75) Inventors: Norikazu Ohtake, Tsukuba (JP); Ryo Yoshimoto, Tsukuba (JP); Shigeru Tokita, Tsukuba (JP); Akio Kanatani, Ushiku (JP); Sayaka Mizutani, Tsuchiura (JP)

(73) Assignee: Banyu Pharmaceutical Co., Ltd., Chuo-ku, Tokyo (JP)

( * ) Notice: Subject to any disclaimer, the term of this patent is extended or adjusted under 35 U.S.C. 154(b) by 0 days.

(21) Appl. No.: 12/381,099

(22) Filed: Mar. 6, 2009

(65) Prior Publication Data

US 2009/0203710 A1 Aug. 13, 2009

Related U.S. Application Data

(62) Division of application No. 10/574,087, filed as application No. PCT/JP2004/013768 on Sep. 21, 2004, now Pat. No. 7,546,693.

(30) Foreign Application Priority Data

Sep. 22, 2003 (JP) .............................. 2003-330758

(51) Int. Cl.
| | |
|---|---|
| C07D 401/14 | (2006.01) |
| C07D 403/14 | (2006.01) |
| A61K 31/4545 | (2006.01) |
| A61K 31/496 | (2006.01) |
| A61K 31/454 | (2006.01) |
| A61K 31/4523 | (2006.01) |
| A61K 31/506 | (2006.01) |
| A61P 3/04 | (2006.01) |
| A61P 3/10 | (2006.01) |
| C07D 401/12 | (2006.01) |
| C07D 401/02 | (2006.01) |
| C07D 401/06 | (2006.01) |

(52) U.S. Cl. .................. 544/330; 544/331; 544/96; 544/124; 514/275; 514/228.8; 514/231.5; 514/315; 514/316; 514/317; 514/318; 514/336; 546/186; 546/208; 546/209; 540/450; 540/484; 540/544; 540/596

(58) Field of Classification Search ................. 544/330, 544/331; 514/275
See application file for complete search history.

(56) References Cited

U.S. PATENT DOCUMENTS 3,951,982 A 4/1976 Goel 7,547,693 B2 * 6/2009 Ohtake et al. ............ 514/228.8

OTHER PUBLICATIONS

Lubishch et al., "Preparation of 2-Phenylbenzimidazoles as Poly (ADP-Ribose) Polymerase Inhibitors", 2000, Database Accession No. 2000:314677.
European Search Report, dated Apr. 2, 2009, Application No. 04787951.5-1211/1669350.

* cited by examiner

Primary Examiner—Venkataraman Balasubramanian
(74) Attorney, Agent, or Firm—J. Eric Thies; Gerard M. Devlin

(57) ABSTRACT

Provided are a histamine-H3 receptor antagonist; and a preventive and/or a remedy for metabolic system diseases such as obesity, diabetes, hormone secretion disorder, hyperlipemia, gout, fatty liver, circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder; and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency. The histamine-H3 receptor antagonist comprises a piperidine derivative compound of formula (I) [wherein $X^1$ and $X^2$ independently represent a nitrogen atom or CH; Y represents a specific group; $X^3$ represents $O_s$—$(CH_2)_m$; $R^1$ and $R^2$ independently resent a hydrogen atom, a halogen atom, a linear or branched lower alkyl group, a lower alkoxy group, or an acetyl group substituted with 2 or 3 fluorine atoms; s is 0 or 1; and m is an integer to make (m+s) 0 or from 1 to 4], or its pharmaceutically-acceptable salt.

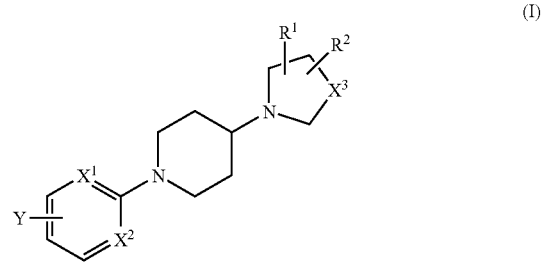

(I)

9 Claims, No Drawings

PIPERIDINE DERIVATIVE

CROSS REFERENCE TO RELATED APPLICATIONS

This application is a division of U.S. application Ser. No. 10/574,087 filed Mar. 21, 2006, now U.S. Pat. No. 7,546,693, which is a U.S. National Phase application under 35 U.S.C. §371 of PCT Application No. PCT/JP2004/013768, filed Sep. 21, 2004, which claims priority under 35 U.S.C. §119 from Japan Application No. JP2003-330758, filed Sep. 22, 2003.

TECHNICAL FIELD

The present invention relates to a novel piperidine derivative, to a histamine-H3 receptor antagonist containing the novel piperidine derivative as an active ingredient thereof, and to a preventive or remedy for metabolic system diseases, circulatory system diseases, central or peripheral nervous system diseases.

BACKGROUND ART

It has been known that, in organisms such as typically mammals, histamine that is a physiologically-active endogenous factor functions as a neurotransmitter and has extensive pharmacological activities (for example, see *Life Science*, 17, 1975, 503 (1975)). Immunohistochemical studies have made it clear that a histamine-agonistic (producing) cell body exists in the nodal papillary nucleus in a posterior hypothalamic region and that histamine nerve fibers project histamine in an extremely broad range in the brain, which supports various pharmacological effects of histamine (for example, see *Journal of Comprehensive Neurology*, 273, 283). The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see *Progress in Neurobiology*, 63, 637 (2001)). The existence of histamine projection to the brain region that relates to vigilance sustenance, for example, to cerebral cortex suggests the role of histamine in control of vigilance or vigilance-sleep cycle. The existence of histamine projection to many peripheral structures such as hippocampus and amygdaloid complex suggests the role of histamine in control of autonomic nerves, emotion, control of motivated action and leaning/memory process.

On the other hand, when released from producing cells, histamine acts with a specific polymer that is referred to as a receptor on the surface of a cell membrane or inside a target cell, therefore exhibiting its pharmacological effects for control of various body functions. Heretofore, four types of histamine receptors (H1 to H4) have been found. In particular, the presence of a histamine receptor that participates in the central and peripheral nervous functions, a histamine-H3 receptor, has been shown by various pharmacological and physiological studies (for example, see *Trends in Pharmacological Science*, 8, 24 (1986)); and recently, human and rodent histamine-H3 receptor genes have been identified and their existence has been made clear (for example, see *Molecular Pharmacology*, 55, 1101 (1999)). It is shown that a histamine-H3 receptor exists in the presynaptic membrane of central or peripheral neurocytes and functions as a self-receptor, therefore controlling the liberation of histamine and controlling the release of other neurotransmitters Specifically, it is reported that a histamine-H3 receptor agonist or its antagonist or inverse-agonist (generically referred to as antagonist) controls the release of histamine, noradrenaline, serotonin, acetylcholine or dopamine from nerve ending. For example, the release of these neurotransmitters is inhibited by an agonist such as (R)-(α)-methylhistamine, and the release of these neurotransmitters is promoted by an antagonist or inverse-agonist such as thioperamide (for example, see *Trends in Pharmacological Science*, 19, 177 (1998)). Recent studies have shown that a histamine-H3 receptor has extremely high homeostatic activities (endogenous agonistic factor, e.g., activity observed in the absence of histamine) in the receptor-expressing cells/tissues or in a membrane fraction derived from the expressing cells/tissues and even in living bodies (for example, see *Nature*, 408, 860). It is reported that these homeostatic activities are inhibited by an antagonist or an inverse-agonist. For example, a homeostatic self-receptor activity is inhibited by thioperamide or syproxyfan, and, as a result, the release of neurotransmitters from nerve ending, for example, the release and liberation of histamine from it is thereby promoted.

Various studies have been made for clarifying the effects of a histamine-H3 receptor. In animal experiments with rats, a high-level selective inhibitor of histamine synthase (histidine decarboxylase) inhibits the vigilance of rats, which suggests that a histamine-H3 receptor may function for controlling motive vigilance. Administration of a histamine-H3 receptor agonist, (R)-(α)-methylhistamine to cats increases their deep slow-wave sleep (for example, see *Brain Research*, 523, 325 (1990)). Contrary to this, it has been clarified that a histamine-H3 receptor antagonist or inverse-agonist, thioperamide dose-dependently increases vigilance, and decreases slow-wave and REM sleep (see *Science*, 48, 2397 (1991)). This suggests that a histamine-H3 receptor may participate in control of vigilance-sleep, and suggests a possibility that a selective histamine-H3 receptor agonist, or its antagonist or inverse-agonist may be useful for treatment of sleep disorders. Further, in animal experiments with rats, administration of histamine to the ventricle of rats inhibited their eating action, therefore suggesting that histamine may participate in control of eating action (for example, see *Research*, 793, 279 (1998)), and it has been clarified that thioperamide dose-dependently inhibits eating action and promotes intracerebral histamine liberation (for example, see *Life Science*, 69, 469 (2001)). These informations suggest that a histamine-H3 receptor may participate in eating action control, further suggesting a possibility that an a histamine-H3 receptor antagonist or inverse-agonist may be useful for prevention or remedy of metabolic diseases such as eating disorder, obesity, diabetes, emaciation, hyperlipemia. In addition, in animal experiments with rats, it has been clarified that administration of a histamine-H3 receptor agonist, (R)-(α)-methylhistamine to rats dose-dependently lowered their basal diastolic pressure, and its action was antagonized by a histamine-H3 receptor antagonist or inverse-agonist, thioperamide (for example, see *Journal of Physiology and Pharmacology*, 49, 191 (1998)). These informations suggest that a histamine-H3 receptor may participate in control of blood pressure, heart beat and cardiac output, further suggesting a possibility that a histamine-H3 receptor agonist or its antagonist or inverse-agonist may be useful for prevention or remedy of circulatory system diseases such as hypertension and various cardiac disorders.

It is reported that, in animal experiments with rats, administration of a histamine-H3 receptor agonist, (R)-(α)-methylhistamine to rats lowered their object recognition and learning effects in the object recognition test and the passive turnout test with them, while on the other hand, in the scopolamine-induced amnesia test with them, a histamine-H3 receptor antagonist or inverse-agonist, thioperamide dose-dependently relieved their amnesia induced by the chemical (for example, see *Behavioural Brain Research*, 104, 147 (1999)). These informations suggest a possibility that a histamine-H3 receptor antagonist or inverse-agonist may be useful for prevention or remedy of various diseases accompanied by memory and learning disorder, for example, Alzheimer's disease, Parkinson's disease or attention deficit/hyperactivity disorder. Further, it has been clarified that, in animal experiments with rats, a histamine-H3 receptor antagonist or inverse-agonist, thioperamide dose-dependently inhibited the spasm induced by electric shock or the epileptoid seizure induced by pentylene tetrazole (PTZ) (for example, see *European Journal of Pharmacology*, 234, 129 (1993) and *Pharmacology, Biochemistry and Behavior*, 68, 735 (2001)). These informations suggest a possibility that a histamine-H3 receptor antagonist or inverse-agonist may be useful for prevention or remedy of epilepsy or central spasm. In addition, a histamine-H3 receptor antagonist or inverse-agonist, thioperamide or GT-2331 reduces emotional cataplexy and sleep of narcoleptic dogs (for example, see *Brain Research*, 793, 279 (1998)).

These information suggest that an H3 receptor may participate in control of vigilance-sleep and sleep disorder-associated diseases, further suggesting a possibility that a selective histamine-H3 agonist or its antagonist or inverse-agonist may be useful for treatment of sleep disorders or various sleep disorder-associated diseases (for example, idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, melancholia, schizophrenia).

In animal experiments with rats, administration of a histamine-H3 receptor antagonist or inverse-agonist thioperamide or GT-2331 to rats relieved the condition of learning disorder (LD) and attention deficit hyperactivity disorder (ADHD) (for example, see *Life Science*, 69, 469 (2001)).

These informations suggest a possibility that a selective H3-agonist or its antagonist or inverse-agonist may be useful for remedy and/or prevention of learning disorder or attention deficit hyperactivity disorder.

There are known a novel imidazole derivative (for example, see JP-T 10-501001) as a histamine-H3 receptor antagonist and/or agonist, 4-(4(5)-imidazolyl)butyramidine, 2-(4)-imidazolylethylisothiourea or an N-methyl derivative thereof having an antagonistic activity against a histamine-H3 receptor (for example, see JP-A-6-87742), or a migraine remedy, a tranquilizer, a hypnotic, an anesthetic, a sedative, an anxiolytic, an antiasthmatic, an antibronchitic and an anti-inflammatory agent that comprise N-methyl derivative thereof; and a histamine receptor antagonist useful for remedy of allergic rhinitis, inflammatory intestinal disorders, asthma, bronchitis and vomition that comprises an N-methyl-N-(4-piperidin-1-yl)-2-arylbutyl)benzamide (for example, see JP-T-2002-504082).

However, no one knows that a piperidine derivative having a skeleton with a nitrogen-containing cyclo-ring and a specific nitrogen-containing heteroaryl ring or phenyl group bonding to piperidine could be a histamine-H3 antagonist, and no one also knows that the piperidine derivative could be effective for metabolic system diseases, circulatory system diseases, central or peripheral nervous system diseases, and especially effective for relieving obesity.

DISCLOSURE OF THE INVENTION

Problems that the Invention is to Solve

An object of the invention is to provide a novel piperidine derivative, and a histamine-H3 receptor antagonist comprising it and to provide a preventive or remedy for metabolic system diseases, circulatory system diseases, central or peripheral nervous system diseases, which is especially effective for obesity and has few side effects.

We, the present inventors have assiduously studied on the assumption that a piperidine derivative may have an antagonistic effect or an adverse effect against a histamine-H3 receptor and could be a histamine-H3 receptor antagonist, and, as a result, have found that a specific piperidine derivative having a skeleton with a specific nitrogen-containing cyclo-ring and a specific nitrogen-containing heteroaryl ring or phenyl group bonding to the piperidine ring thereof are effective for relieving metabolic system diseases, circulatory system diseases, central or peripheral nervous system diseases, and have completed the invention.

Specifically, the invention relates to a compound of a general formula (I):

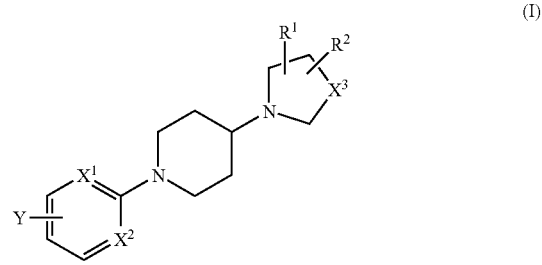

[in formula (I), $X^1$ and $X^2$ independently represent a nitrogen atom or CH; $X^3$ represents $O_s$—$(CH_2)_m$ (in which s indicates 0 or 1; m indicates an integer to make (m+s) 0 or 1 to 4); Y represents a group of a general formula (II):

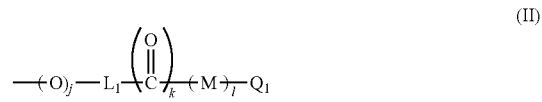

(in formula (II), j, k and l independently indicate 0 or 1; $L_1$ represents a C1 to C4 lower alkylene group or a single bond;

M represents an oxygen atom or a group of a general formula (III):

(in formula (III), $R^0$ represents a hydrogen atom or a C1 to C4 lower alkyl group); $Q_1$ represents a linear or branched lower alkyl group, an optionally-condensed C3 to C9 cycloalkyl group, a phenyl group, a naphthyl group, or an optionally-condensed 3- to 8-membered heterocyclic group (the hetero ring may have from 1 to 3 hetero atoms selected from a group consisting of an oxygen atom, a sulfur atom and a nitrogen atom), which is unsubstituted or has a substituent selected from a group consisting of a cyano group, a hydroxyl group, a lower alkyl group (the lower alkyl group may be further substituted with a hydroxyl group, a halogen atom, an amino group, an aryl group or a heteroaryl group), a cycloalkyl group, a lower alkoxy group (the lower alkoxy group may be further substituted with a halogen atom), a halogen atom, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group) (but excepting the following:

1) a case where Y is an alkoxycarbonyl group, or 2) a case where Y of formula (II) is a group of the following formula (II-1):

   (II-1)

(in formula (II-1), $L_1$ and $Q_1$ have the same meaning as $L_1$ and $Q_1$ in formula (II));

$R^1$ and $R^2$ independently represent a hydrogen atom, a halogen atom, a linear or branched lower alkyl group, a lower alkoxy group, or an acetyl group substituted with 2 or 3 fluorine atoms] (but excepting 1-[4-(piperidin-1-yl)piperidin-1-yl]-4-(7-carbamoyl-1H-benzimidazol-2-yl)benzene, 1-{4-(piperidin-1-yl)piperidin-1-yl}-4-(5-cyano-6-oxo-pyridin-2-yl)benzene and 1-{4-(pyrrolidin-1-yl)piperidin-1-yl}-4-(5-cyano-pyridin-2-yl)benzene) or its pharmaceutically-acceptable salt.

The invention also relates to the compound or its pharmaceutically-acceptable salt wherein, in formula (I), $R^1$ and $R^2$ are hydrogen atoms, m in $X^3$ is an integer of from 1 to 3, and s is 0.

The invention further relates to the compound or its pharmaceutically-acceptable salt wherein, in formula (II), Y is a group of a general formula (IV):

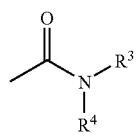   (IV)

in formula (IV), $R^3$ is a hydrogen atom, or a lower alkyl group, and $R^4$ is a group of a general formula (V):

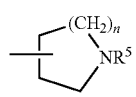   (V)

[in formula (V), $R^5$ represents a hydrogen atom, a lower alkyl group, a C3 to C8 cycloalkyl group, an aralkyl group, or a heteroaryl group; n indicates 0 or an integer of from 1 to 4]; or relates to the compound or its pharmaceutically-acceptable salt wherein, in formula (II), Y is a group of a general formula (IV):

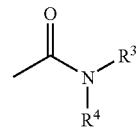   (IV)

in formula (IV), $R^3$ is a hydrogen atom, or a lower alkyl group, and $R^4$ is a group of a general formula (VI):

   (VI)

[in formula (VI), A represents an aryl group, a heteroaryl group, a condensed bicyclic group of a C4 to C7 cycloalkyl group and an aryl group, or a condensed bicyclic group of a C4 to C7 cycloalkyl group and a heteroaryl group; q indicates 0 or an integer of from 1 to 3]or relates to the compound or its pharmaceutically-acceptable salt wherein, in formula (II), Y is a group of a general formula (IV):

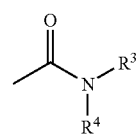   (IV)

in formula (IV), $R^3$ and $R^4$ form a nitrogen containing heterocyclic group as integrated with the nitrogen atom to which they bond.

The invention also relates to the compound or its pharmaceutically-acceptable salt, wherein Y is a group of a general formula (IV) wherein the nitrogen-containing heterocyclic group is a monocyclic group such as a piperidinyl group, a pyrrolidinyl group, an azetidinyl group, a homopiperidinyl group or a heptamethyleneiminyl group, or a bicyclic group of such a monocyclic group and a C4 to C7 cycloalkyl group, a phenyl group or a pyridyl group; or relates to the compound or its pharmaceutically-acceptable salt, wherein $X^1$ and $X^2$ are both $CH_2$, or one of them is a nitrogen atom; or relates to the compound or its pharmaceutically-acceptable salt wherein, in formula (II), Y is an aryl group or a 5-membered or 6-membered heteroaryl group (the heteroaryl group has, in the ring thereof, from 1 to 3 hetero atoms selected from a group consisting of a nitrogen atom, a sulfur atom and an oxygen atom), which is unsubstituted or substituted with 1 or 2 substituents selected from a group consisting of a lower alkyl group, a lower alkoxy group, a hydroxyl group and a halogen atom; or relates to the compound or its pharmaceutically-acceptable salt, wherein $X^1$ and $X^2$ are both nitrogen atoms; or relates to the compound or its pharmaceutically-acceptable salt wherein the piperidine derivative compound of formula (I) is any of the following:

N-methyl-N-(1-methylpiperidin-4-yl)-4-[4-(piperidin-1-yl)piperidin-1-yl]benzamide (1), N-(1-methylpiperidin-4-yl)-4-[4-(piperidin-1-yl)piperidin-1-yl]benzamide (2), N-methyl-N-(1-cyclobutylpiperidin-4-yl)-4-[4-(piperidin-1-yl)piperidin-1-yl]benzamide (3), N-methyl-N-(1-cyclopentylpiperidine-4-yl)-4-[4-(piperidin-1-yl)piperidin-1-yl]benzamide (4), N-methyl-N-(1-cyclohexylpiperidin-4-yl)-4-[4-(piperidin-1-yl)piperidin-1-yl]benzamide (5), N-methyl-N-(1-cyclohexylmethylpiperidin-4-yl)-4-[4-(piperidin-1-yl)piperidin-1-yl]benzamide (6),
N-methyl-N-[(3R)-1-cyclopentylpyrrolidin-3-yl]-4-[4-(piperidin-1-yl)piperidin-1-yl]benzamide (7),
N-methyl-N-[(3S)-1-cyclopentylpyrrolidin-3-yl)]-4-[4-piperidin-1-yl)piperidin-1-yl]benzamide (8),
N-methyl-N-[(3R)-1-benzylpyrrolidin-3-yl)]-4-[4-(piperidin-1-yl)piperidin-1-yl]benzamide (9),
N-methyl-N-[(3R)-1-benzylpyrrolidin-3-yl)]-4-[4-(piperidin-1-yl)piperidin-1-yl]benzamide (10),
N-(pyridin-4-yl)-4-[4-(piperidin-1-yl)piperidin-1-yl]benzamide trifluoroacetate (11),
2-{4-(piperidin-1-yl)piperidin-1-yl]benzoyl-1,2,3,4-tetrahydroisoquinoline (12),
1-{4-(piperidin-1-yl)piperidin-1-yl]benzoyl-1,2,3,4-tetrahydroquinoline (13),
1-{4-(piperidin-1-yl)piperidin-1-yl]benzoyl-4-phenylpiperazine (14),
N-methyl-N-[1-(pyrimidin-2-yl)piperidin-4-yl]-4-[4-(piperidin-1-yl)piperidin-1-yl]benzamide (15),
N-methyl-N-(thiophen-2-yl)methyl-4-[4-(piperidin-1-yl)piperidin-1-yl]benzamide (16),
N-methyl-N-phenethyl-4-[4-(piperidin-1-yl)piperidin-1-yl]benzamide (17),
1-{4-(piperidin-1-yl)piperidin-1-yl]benzoyl-3-(3,4-difluorophenyl)pyrrolidine (18),
4-{-4-(piperidin-1-yl)piperidin-1-yl]benzylpiperidin-1-yl (19),
N-methyl-N-(1-methylpiperidin-4-yl)-4-[4-(pyrrolidin-1-yl)piperidin-1-yl]benzamide (20),
N-methyl-N-(1-methylpiperidin-4-yl)-4-[4-(azetidin-1-yl)piperidin-1-yl]benzamide (21),
N-methyl-N-(1-methylpiperidin-4-yl)-5-[4-(piperidin-1-yl)piperidin-1-yl]pyridine-2-carboxamide (22),
N-methyl-N-(1-methylpiperidin-4-yl)-4-[4-(4,4-difluoropiperidin-1-yl)piperidin-1-yl]benzamide (23),
2-[(4-piperidin-1-yl)piperidin-1-yl]-5(4-cyanophenyl)pyrimidine (24),
2-[(4-piperidin-1-yl)piperidin-1-yl]-5-(3-pyridyl)pyrimidine (25),
2-[4-(piperidin-1-yl)piperidin-1-yl]-5-(3-trifluoromethylphenyl)pyrimidine (26),
2-[4-(piperidin-1-yl)piperidin-1-yl]-5-(3,5-dichlorophenyl)pyrimidine (27),
2-[4-(piperidin-1-yl)piperidin-1-yl]-5-(2-naphthyl)pyrimidine (28),
2-[4-(piperidin-1-yl)piperidin-1-yl]-5-[4-(pyrrolidin-1-ylcarbonyl)phenyl]pyrimidine (29),
1-[4-(piperidin-1-yl)piperidin-1-yl]-4-(3-pyridyl)benzene (30),
1 (piperidin-1-ylmethyl)-4-[4-(piperidin-1-yl)piperidin-1-yl]benzene (31).

The invention also relates to a histamine-H3 antagonist or inverse-agonist containing, as the active ingredient thereof, a compound or its pharmaceutically-acceptable salt of formula (I); or relates to a preventive or remedy containing, as the active ingredient thereof, a compound or its pharmaceutically-acceptable salt of formula (I), which is for metabolic system diseases such as obesity, diabetes, hormone secretion disorder, hyperlipemia, gout, fatty liver, circulatory system diseases, for example, stenocardia, acute/congestive cardiac insufficiency, cardiac infarction, coronary arteriosclerosis, hype ion, nephropathy, sleep disorder and various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder, and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency; or relates to a method for producing a compound of a general formula (I-1), which comprise reacting a compound of a general formula (Ia):

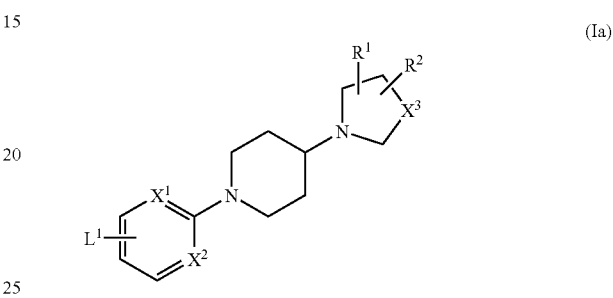

(Ia)

[wherein $X^1$, $X^2$, $X^3$, $R^1$ and $R^2$ have the same meanings as $X^1$, $X^2$, $X^3$, $R^1$ and $R^2$ in formula (I); and $L^1$ represents a leaving group] and a compound of a general formula (IIa):

Met-$Y^{1p}$ (IIa)

[wherein Met represents a metal atom-containing atomic group; and $Y^{1p}$ has the same meaning as Y in a general formula (II):

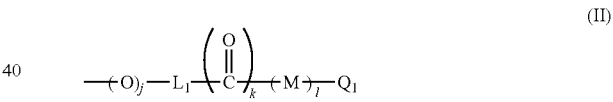

(II)

or represents a group corresponding to it but protected at the amino group, the hydroxyl group or the carboxyl group therein], in the presence of a catalyst to give a compound of a general formula (Ib):

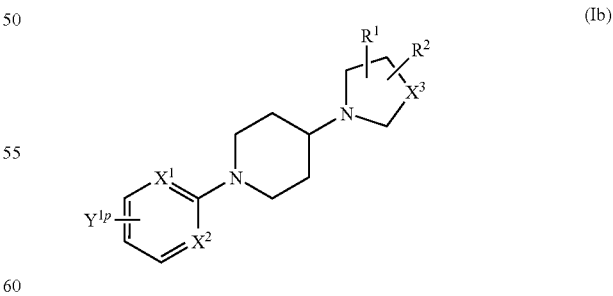

(Ib)

[wherein $X^1$, $X^2$, $X^3$, $R^1$ and $R^2$ have the same meanings as $X^1$, $X^2$, $X^3$, $R^1$ and $R^2$ in formula (Ia); and $Y^{1P}$ has the same meaning as $Y^{1p}$ in formula (IIa)], and optionally removing or converting the protective group for the functional group of $Y^{1p}$ to thereby produce a compound of a general formula (I-1):

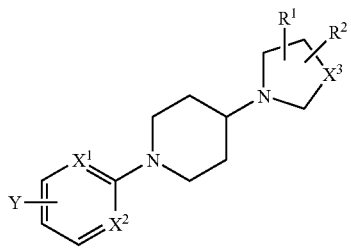
(I-1)

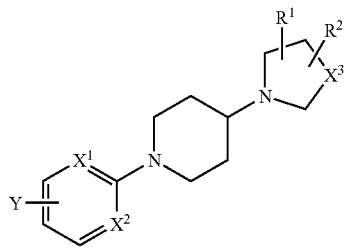
(I-2)

[wherein $X^1$, $X^2$, $X^3$, $R^1$ and $R^2$ have the same meanings as $X^1$, $X^2$, $X^3$, $R^1$ and $R^2$ in formula (Ib); and Y is a group derived from $Y^{1p}$ in formula (Ib) by removing or converting the protective group for the functional group of $Y^{1p}$]; or relates to a method for producing a compound of a general formula (I-2), which comprises reacting a compound of a general formula (Ic):

[wherein $X^1$, $X^2$, $X^3$, $R^1$ and $R^2$ have the same meanings as $X^1$, $X^2$, $X^3$, $R^1$ and $R^2$ in formula (Ie); and Y is a group derived from $Y^{1p}$ in formula (Ie) by removing or converting the protective group for the functional group of $Y^{1p}$]; or relates to a method for producing a compound of a general formula (I-3), which comprises reacting a compound of a general formula (If):

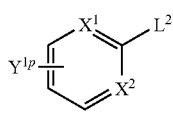
(Ic)

[wherein $X^1$ and $X^2$ have the same meanings as $X^1$ and $X^2$ in formula (I); $Y^{1p}$ has the same meaning as Y in formula (n), or represents a group corresponding to it but protected at the amino group, the hydroxyl group or the carboxyl group therein; and $L^2$ represents a leaving group] and a compound of a formula (Id):

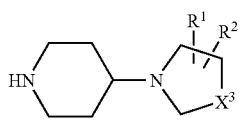
(Id)

[wherein $R^1$, $R^2$ and $X^3$ have the same meanings as $R^1$, $R^2$ and $X^3$ in formula a)] under a basic condition or in the presence of a catalyst to give a compound of a general formula (Ie):

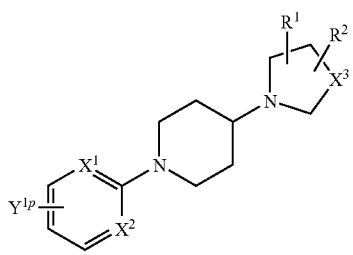
(Ie)

[wherein $X^1$, $X^2$ and $Y^{1p}$ have the same meanings as $X^1$, $X^2$ and $Y^{1p}$ in formula (Ic); $X^3$, $R^1$ and $R^2$ have the same meanings as $X^3$, $R^1$ and $R^2$ in formula (Id)], and optionally removing or converting the protective group for the functional group of $Y^{1p}$ to thereby produce a compound of a general formula (I-2):

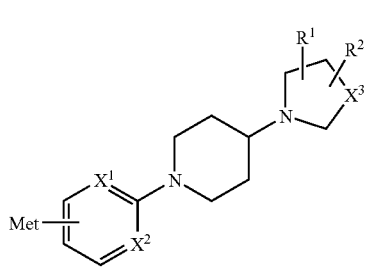
(If)

[wherein $X^1$, $X^2$, $X^3$, $R^1$ and $R^2$ have the same meanings as $X^1$, $X^2$, $X^3$, $R^1$ and $R^2$ in formula (I); Met represents a metal atom-containing atomic group] and a compound of a general formula (IIb):

$$Y^{1p}\text{-}L^2 \quad (\text{IIb})$$

[wherein $Y^{1p}$ has the same meaning as Y in a general formula (II), or represents a group corresponding to it but protected at the amino group, the hydroxyl group or the carboxyl group therein; and $L^2$ represents an ordinary leaving group] to give a compound of a general formula (Ig):

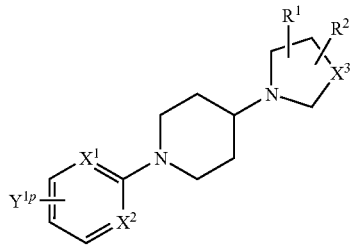
(Ig)

[wherein $X^1$, $X^2$, $X^3$, $R^1$ and $R^2$ have the same meanings as $X^1$, $X^2$, $X^3$, $R^1$ and $R^2$ in formula (If); and YIP has the same meaning as $Y^{1p}$ in formula (IIb)], and optionally removing or converting the protective group for the functional group of $Y^{1p}$ to thereby produce a compound of a general formula (I-3):

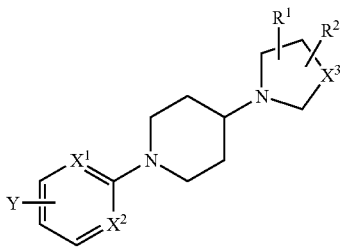

(I-3)

[wherein $X^1$, $X^2$, $X^3$, $R^1$ and $R^2$ have the same meanings as $X^9$, $X^2$, $X^3$, $R^1$ and $R^2$ in formula (Ig); and Y is a group derived from $Y^{1p}$ in formula (Ig) by removing or converting the protective group for the functional group of $Y^{1p}$].

BEST MODE FOR CARRYING OUT THE INVENTION

Unless otherwise specifically indicated, the group as referred to in this description concretely includes those mentioned below.

"Halogen atom" includes, for example, a fluorine atom, a chlorine atom, a bromine atom, an iodine atom.

"Lower alkyl group" may be a linear or branched C1 to C6 alkyl group, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-ethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Lower alkoxy group" means a hydroxyl group of which the hydrogen atom is substituted with the above-mentioned lower alkyl group, including, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Mono-lower alkylcarbonyloxy group" means a carbonyloxy group to be formed by substitution of the hydrogen atom of a formyloxy group with the above-mentioned lower alkyl group, including, for example, a methylcarbonyloxy group, an ethylcarbonyloxy group, a propylcarbonyloxy group, an isopropylcarbonyloxy group.

"Alkanoyl group" may be a lower alkanoyl group, including, for example, a formyl group, an acetyl group, a propionyl group, a butyryl group, a pivaloyl group.

"C3 to C9 cycloalkyl group" includes, for example, a cyclopropyl group, a cyclobutyl group, a cyclopentyl group, a cyclohexyl group, a cycloheptyl group, a cyclooctyl group, a cyclononyl group.

"Aryl group" includes, for example, a phenyl group, a 1-naphthyl group, a 2-naphthyl group.

"Aralkyl group" may be the above-mentioned lower alkyl group having the above-mentioned aryl group, including, for example, a benzyl group, a 1-phenylethyl group, a 2-phenylethyl group, a 1-naphthylmethyl group, a 2-naphthylmethyl group.

"Heteroaryl group" means a 5- or 6-membered monocyclic heteroaryl group having therein from 1 to 3 hetero atoms selected from an oxygen atom, a sulfur atom and a nitrogen atom, including, for example, a 5-membered cyclic group such as a 2-furyl group, a 3-furyl group, a 2-thienyl group, a 3-thienyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 1-(1,2,4-triazolyl) group, a 3-(1,2,4-triazolyl) group, a 1-(1,2,3-triazolyl) group, a 4-(1,2,3-triazolyl) group, a 2-thiazolyl group, a 4-thiazolyl group, a 5-thiazolyl group, a 4-(1,2,3-thiadiazolyl) group, a 3-(1,2,4-thiadiazolyl) group, a 2-(1,3,4-thiadiazolyl) group, a 3-isothiazolyl group, a 4 isothiazolyl group, a 2-oxazolyl group, a 4-oxazolyl group, a 5-oxazolyl group, a 3-isoxazolyl group, a 4 isoxazolyl group; and a 6-membered cyclic group such as a 2-pyridyl group, a 3-pyridyl group, a 4-pyridyl group, a 2-pyrimidinyl group, a 4-pyrimidinyl group, a 5-pyrimidinyl group, a 3-pyridazinyl group, a 4-pyridazinyl group, a 5-pyridazinyl group, a 2-pyrazinyl group.

"Heterocyclic group" may be a 3-membered to 8-membered monocyclic heterocyclic group containing from 1 to 3 hetero atoms selected from an oxygen atom, a sulfur atom and a nitrogen atom, including, for example, a 1-aziridinyl group, a 1-azetidinyl group, a 2-azetidinyl group, a 1-pyrrolidinyl group, a 2-pyrrolidinyl group, a 3-pyrrolidinyl group, a 1-piperidino group, a 2-piperidyl group, a 3-piperidyl group, a 4-piperidyl group, a 1-hexamethyleneiminyl group, a 2-hexamethyleneiminyl group, a 3-hexamethyleneiminyl group, a 4-hexamethyleneiminyl group, a 1-heptamethyleneiminyl group, a 2-heptamethyleneiminyl group, a 3-heptamethyleneiminyl group, a 4-heptamethyleneiminyl group, a 1-pyrazolidinyl group, a 3-pyrazolidinyl group, a 4 pyrazolidinyl group, a 1-piperazinyl group, a 2-piperazinyl group, a 1-homopiperazinyl group, a 2-homopiperazinyl group, a 5-homopiperazinyl group, a 6-homopiperazinyl group, a 2-oxetanyl group, a 3-oxetanyl group, a 2-tetrahydropyranyl group, a 3-tetrahydrofuranyl group, a 2-tetrahydropyranyl group, a 3-tetrahydropyranyl group, a 4-tetrahydropyranyl group, a 2-tetrahydrothiophenyl group, a 3-tetrahydrothiophenyl group, a 2-thianyl group, a 3-thianyl group, a 4-thianyl group, a 2-morpholinyl group, a 3-morpholinyl group, a morpholino group, a 2-thiazolidinyl group, a 3-thiazolidino group, a 4-thiazolidinyl group, a 5-thiazolidinyl group.

"Cycloalkyliminocarbamoyl group" means a carbamoyl group substituted with a cycloalkylamino group. The cycloalkylamino group means a group derived from the above-defined cycloalkyl group by substituting one $CH_2$ constituting the cycloalkyl group with NH. The cycloalkyliminocarbamoyl group includes, for example, an azetidin-2-yl-carbamoyl group, an azetidin-3-yl-carbamoyl group, a pyrrolidin-2-yl-aroyl group, a pyrrolidin-3-yl-carbamoyl group, a piperidin-2-yl-carbamoyl group, a piperidin-3-yl-carbamoyl group, a piperidin-4-yl-carbamoyl group, a hexamethyleneimine-2-yl-carbamoyl group, a hexamethyleneimine-3-yl-carbamoyl group, a hexamethyleneimine-4-yl-carbamoyl group, a heptamethyleneimine-2-yl-carbamoyl group, a heptamethyleneimine-3-yl-carbamoyl group, a heptamethyleneimine-4-yl-carbamoyl group, a heptamethyleneimine-5-yl-carbamoyl group.

"Mono-lower alkylcarbamoyl group" means a carbamoyl group substituted with one above-mentioned lower alkyl group, including, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group.

"Di-lower alkylcarbamoyl group" means a carbamoyl group substituted with two above-mentioned lower alkyl groups that may be the same or different, including, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

The di-lower alkylcarbamoyl group further includes a 5-membered to 8-membered monocyclic or spin cyclic group to be formed by the nitrogen atom constituting the carbamoyl group and the same or different lower alkyl groups bonding to the nitrogen atom, and a bicyclic group to be formed through condensation of the 5-membered to 8-membered monocyclic group with a benzene or pyridine ring. Concretely, these are groups of the following formula (b):

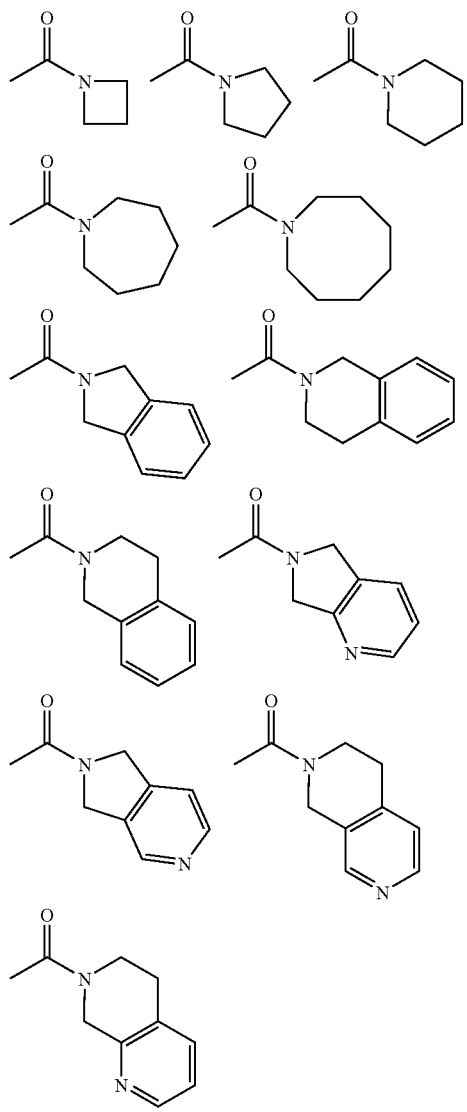

"Lactam ring" includes a 3-membered to 9-membered monocyclic group having a group of —N(R$^6$)—C(O)— in the ring, or a group having 1 or 2 carbon-carbon double bonds in the ring, or a group having 1 or 2 oxygen atoms or nitrogen atoms in addition to the nitrogen atom that constitutes —N—C(O)—. Not specifically defined, the bonding position of the lactam ring may be any one to which the ring may bond. R$^6$ represents a hydrogen atom or a lower alkyl group. More concretely, the lactam ring includes those of the following formula (c):

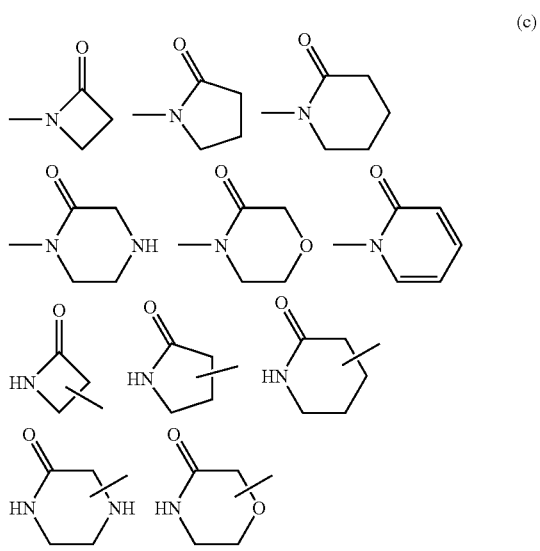

Of those, preferred are β-propiolactam, 2-pyrrolidone-1-yl, 2-piperidon-1-yl, 2-piperidon-1-yl, 2-morpholidon-1-yl.

"Mono-lower alkylamino group" means an amino group substituted with one above-mentioned lower alkyl group, including, for example, a methylamino group, an ethylamino group, a propylamino group, an isopropylamino group, a butylamino group, a sec-butylamino group, a tert-butylamino group.

"Di-lower alkylamino group" means an amino group substituted two above-mentioned lower alkyl groups, including, for example, a dimethylamino group, a diethylamino group, a dipropylamino group, a diisopropylamino group, a methylethylamino group, a methylpropylamino group.

"Mono-lower alkylaminocarbonyloxy group" means a carbonyloxy group to be formed by substituting the hydrogen atom of a formyloxy group with an ammo group substituted with one above-mentioned lower alkyl group, including, for example, a methylaminocarbonyloxy group, an ethylaminocarbonyloxy group, a propylaminocarbonyloxy group, an isopropylaminocarbonyloxy group.

"Di-lower alkylcarbamoyloxy group" means a carbamoyloxy group substituted with two above-mentioned lower alkyl groups that may be the same or different, including, for example, a dimethylcarbamoyloxy group, a diethylcarbamoyloxy group, a diisopropylcarbamoyloxy group, an ethylmethylcarbamoyloxy group.

"Alkylene group" means a C1 to C6 linear or branched alkylene group, including, for example, a methylene group, an ethylene group, a trimethylene group, a tetramethylene group, a pentamethylene group.

The novel piperidine derivatives of the invention are represented by the following general formula (I):

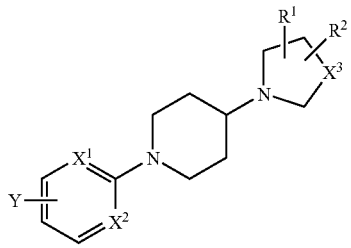

(I)

in which a predetermined nitrogen-containing heterocyclic group bonds to the 4-position of the piperidine ring and a predetermined aromatic ring bonds to the 1-position of the piperidine ring. Not specifically defined, the novel piperidine derivatives of the invention includes those as above and their pharmaceutically-acceptable salts.

In formula (I), $X^3$ in the nitrogen-containing heterocyclic group that bonds to the 4-position of the piperidine ring indicates $O_s$—$(CH_2)_m$; s indicates 0 or 1; m indicates an integer to make (m+s) 0 or from 1 to 4. The nitrogen-containing heterocyclic group may be a 4-membered to 8-membered group, concretely including a 1-azetidinyl group, a 1-pyrrolidinyl group, a piperidino group, a 1-hexamethyleneiminyl group, a 1-heptamethyleneiminyl group, a morpholino group. Of those, preferred are a 1-pyrrolidinyl group, a piperidino group, a 1-hexamethyleneiminyl group; and more preferred is a piperidino group.

$R^1$ and $R^2$ in the nitrogen-containing heterocyclic group are independently a hydrogen atom, a halogen atom, a linear or branched lower alkyl group, a lower alkoxy group, or an acetyl group substituted with 2 or 3 fluorine atoms. The halogen atom, the linear or branched lower alkyl group and the lower alkoxy group for $R^1$ and $R^2$ are concretely those mentioned hereinabove. The acetyl group substituted with 2 or 3 fluorine atoms for $R^1$ and $R^2$ includes, for example, a perfluoroacetyl group, a difluoroacetyl group. Of those substituents, $R^1$ and $R^2$ are preferably hydrogen atoms.

In formula (I), $X^1$ and $X^2$ in the aromatic ring bonding to the 1-position of the piperidin ring independently represent a nitrogen atom or CH. As so mentioned hereinunder, their preferred combinations may be selected depending on the hydrogen atom or the substituent Y bonding to the aromatic ring.

In formula (I), the substituent Y of the aromatic ring bonding to the 1-position of the piperidine ring is represented by the following general formula (II):

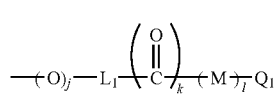

(II)

In formula (II), $L_1$ represents a C1 to C4 alkylene group or a single bond, preferably a single bond, or a C1 to C3 alkylene group such as a methylene group, an ethylene group, a propylene group; more preferably a single bond, a methylene group or an ethylene group.

In formula (II), M represents an oxygen atom or a group of the following general formula (III):

(III)

In formula (III), $R^0$ represents a hydrogen atom or a C1 to C4 alkyl group. The C1 to C4 alkyl group for $R^0$ includes, for example, a methyl group, an ethyl group, a propyl group, an n-butyl group, an isopropyl group, an isobutyl group, a tert-butyl group. Of those, preferred are a methyl group, an ethyl group, a propyl group, an n-butyl group, an isopropyl group; and more preferred are a methyl group, an ethyl group, a propyl group, an isopropyl group.

In formula (II), j, k and l independently indicate 0 or 1. A group represented by Y in formula (II) includes, for example, the following:

-$Q_1$, —$(CH_2)_n$-$Q_1$ (n indicates an integer of from 1 to 4, and the same shall apply hereinunder), —O-$Q_1$, —$(NR^0)$-$Q_1$, —$(CH_2)_n$—$(NR^0)$-$Q_1$, —(CO)-$Q_1$, —(CO)—$(CH_2)_n$-$Q_1$, —(CO)—O-$Q_1$, —(CO)—$(NR^0)$-$Q_1$, —(CO)—$(CH_2)_n$-$Q_1$, —(CO)—$(CH_2)_n$—$(NR^0)$-$Q_1$, —O—$(CH_2)_n$-$Q_1$, —O—O-$Q_1$, —O—$(NR^0)$-$Q_1$, —O—$(CH_2)_n$—O-$Q_1$, —O—$(CH_2)_n$—$(NR^0)$-$Q_1$, —O—(CO)—$(CH_2)_n$-$Q_1$, —O—(CO)—O-$Q_1$, —O—(CO)—$(NR^0)$-$Q_1$, —O—(CO)—$(CH_2)_n$—O-$Q_1$, —O—(CO)—$(CH_2)_n$—$(NR^0)$-$Q_1$.

Of those, preferred are —$(CH_2)_n$-$Q_1$, —(CO)-$Q_1$, —(CO)-$Q_1$, —$(CH_2)_n$—(CO)-$Q_1$, —$(CH_2)_n$—(CO)—O-$Q_1$, —(CO)—$(NR^0)$-$Q_1$, —$(CH_2)_n$—(CO)—$(NR^0)$-$Q_1$, —O—$(CH_2)_n$-$Q_1$; more preferred are —$(CH_2)_n$-$Q_1$, —(CO)—O-$Q_1$, —$(CH_2)_n$—(CO)—O-$Q_1$, —(CO)—$(NR^0)$-$Q_1$, —$(CH_2)$—(CO)—$(NR^0)$-$Q_1$, —O-$Q_1$, —O—$(CH_2)_n$-$Q_1$.

In formula (II), $Q_1$ represents a linear or branched lower alkyl group, an optionally-condensed C3 to C9 cycloalkyl group, a phenyl group, a naphthyl group, or an optionally-condensed 3-membered to 8-membered heterocyclic group. These groups may be unsubstituted, or may be substituted with one or more substituents selected from a cyano group, a hydroxyl group, a lower alkyl group (the lower alkyl group may be further substituted with a hydroxyl group, a halogen atom, an amino group, an aryl group or a heteroaryl group), a cycloalkyl group, a lower alkoxy group (the lower alkoxy group may be further substituted with a halogen atom), a halogen atom, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group.

The linear or branched lower alkyl group represented by $Q_1$ may be a linear or branched C1 to C6 alkyl group, concretely including those mentioned hereinabove. Of those, preferred are a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, an n-hexyl group, an isohexyl group; and more preferred are a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a hexyl group, an isohexyl group.

Of the substituents mentioned hereinabove, the substituent that the linear or branched lower alkyl group for $Q_1$ may have is more preferably a cyano group, a hydroxyl group, a lower alkoxy group (the lower alkoxy group may be further substituted with a halogen atom), a halogen atom, an amino group, an aryl group, a heteroaryl group, a di-lower alkylaminocarbonyloxy group, a di-lower alkylcarbamoyl group and a trifluoromethyl group, even more preferably a hydroxyl group, a lower alkoxy group (the lower alkoxy group may be further substituted with a halogen atom) and a trifluoromethyl group.

The lower alkoxy group for the substituent in the linear or branched lower alkyl group for $Q_1$ concretely includes those mentioned hereinabove. The lower alkoxy group may be further substituted with a halogen atom. The halogen atom concretely includes those mentioned hereinabove. The di-lower alkylcarbamoyl group, the di-lower alkylaminocarbonyloxy group, the aryl group and the heteroaryl group for the substituent in the linear or branched lower alkyl group for $Q_1$ concretely includes those mentioned hereinabove. The linear or branched lower alkyl group for $Q_1$ may have 1 or 2 abovementioned substituents at their bondable positions.

In formula (II), the C3 to C9 cycloalkyl group for $Q_1$ concretely includes those mentioned hereinabove. Of those, preferred are a cyclopropyl group, a cyclobutyl group, a cyclopentyl group, a cyclohexyl group, a cycloheptyl group; more preferred are a cyclopropyl group, a cyclobutyl group, a cyclopentyl group, a cyclohexyl group. The C3 to C9 cycloalkyl group for $Q_1$ may be a bicyclic group condensed with a benzene ring, for example, a 1-benzo[b]cyclopropyl group, a 1-benzo[b]cyclobutyl group, a 1-benzo[b]cyclopentyl group, a 1-benzo[b]cyclohexyl group, a 1-benzo[c]heptyl group, a 1-benzo[c]cyclooctyl group, a 1-benzo[c]cyclononyl group.

The substituent that the C3 to C9 cycloalkyl group for $Q_1$ may have is preferably a cyano group, a hydroxyl group, a lower alkyl group (the lower alkyl group may be further substituted with a hydroxyl group, a halogen atom, an amino group, an aryl group, a heteroaryl group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group. Of those, more preferred are a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group and an alkanoyl group. "Lower alkyl group", "lower alkoxy group", "halogen atom", "mono-lower alkylcarbonyloxy group", "di-lower alkylcarbamoyloxy group", "mono-lower alkylcarbamoyl group", "di-lower alkylcarbamoyl group", "cycloalkyliminocarbamoyl group", "lactam ring", "mono-lower alkylamino group", and "di-lower alkylamino group" for the substituent of the C3 to C9 cycloalkyl group for $Q^1$ are concretely the same as those mentioned hereinabove. The C3 to C9 cycloalkyl group for $Q^1$ may have 1 or 2 these substituents at their bondable positions.

Of the substituents mentioned hereinabove, the substituent that the phenyl group for $Q^1$ in formula (II) may have is preferably a cyano group, a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group. Of those, more preferred are a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group and an alkanoyl group. "Lower alkyl group", "lower alkoxy group", "halogen atom", "mono-lower alkylcarbonyloxy group", "di-lower alkylcarbamoyloxy group", "mono-lower alkylcarbamoyl group", "di-lower alkylcarbamoyl group", "cycloalkyliminocarbamoyl group", "lactam ring", "mono-lower alkylamino group", and "di-lower alkylamino group" for the substituent of the phenyl group for $Q^1$ are concretely the same as those mentioned hereinabove. The phenyl group for $Q^1$ may have 1 or 2 these substituents at their bondable positions.

Of the substituents mentioned hereinabove, the substituent that the naphthyl group for $Q^1$ in formula (II) may have is preferably a cyano group, a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group. Of those, more preferred are a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group and an alkanoyl group. "Lower alkyl group", "lower alkoxy group", "halogen atom", "mono-lower alkylcarbonyloxy group", "di-lower alkylcarbamoyloxy group", "mono-lower alkylcarbamoyl group", "di-lower alkylcarbamoyl group", "lactam ring", "mono-lower alkylamino group", and "di-lower alkylamino group" for the substituent of the naphthyl group for $Q^1$ are concretely the same as those mentioned hereinabove. The naphthyl group for $Q^1$ may have 1 or 2 these substituents at their bondable positions.

In formula (II), the optionally-condensed 3-membered to 8-membered heterocyclic group for $Q^1$ is a 3-membered to 8-membered cyclic compound residue containing from 1 to 3 hetero atoms selected from an oxygen atom, a sulfur atom and a nitrogen atom. The heterocyclic group includes a monocyclic group of a 5-membered or 6 membered heteroaryl group having from 1 to 3 hetero atoms selected from an oxygen atom, a sulfur atom and a nitrogen atom; a bicyclic or tricyclic group formed through condensation of the monocyclic heteroaryl group with a benzene ring or a pyridine ring; a monocyclic group of a 3-membered to 8-membered heterocyclic group; and a bicyclic group formed through condensation of the monocyclic heterocyclic group with a benzene ring or a pyridine ring. The 5-membered or 6-membered heteroaryl group includes the same as those mentioned hereinabove. Of those, preferred are a furyl group, a thienyl group, a pyrrolyl group, a pyrazolyl group, a thiazolyl group, a thiadiazolyl group, an isothiazolyl group, an oxazolyl group, an isoxazolyl group, a pyridyl group, a pyrimidinyl group, a pyrazinyl group; and more preferred are a pyrazolyl group, a thiazolyl group, a thiadiazolyl group, an isothiazolyl group, an oxazolyl group, an isoxazolyl group, a pyridyl group, a pyrimidinyl group, a pyrazinyl group.

The bicyclic or tricyclic group to be formed through condensation of a monocyclic heteroaryl group and a benzene ring or a pyridine ring for $Q^1$ includes, for example, a bicyclic group such as a 2-benzofuranyl group, a 3-benzofuranyl group, a 1-indolyl group, a 2-indolyl group, a 3-indolyl group, a 2-quinolyl group, a 4-quinolyl group, a 8-quinolyl group, a 1-isoquinolyl group, a 3-isoquinolyl group, a 4-isoquinolyl group, a 2-benzoxazolyl group, a 3-benzoxazolyl group, a 1-benzimidazolyl group, a 2-benzimidazolyl group, a 1-phthalazinyl group, a 2-phthalazinyl group, a quinoxalinyl group, a 2-quinazolinyl group, a 4-quinazolinyl group a 4-(4H-quinolidinyl) group, a 3-cinnolinyl group, a 4-cinnolinyl group, a 1-pyridoimidazolyl group, a 2-imidazopyridyl group, a 2-(1,5-naphthyridinyl) group, a 2-(1,8-naphthyridinyl) group, a 2-(2,7-naphthyridinyl) group, a 2-benzisoxazolyl group, a benzothiazolyl group, a pyridooxazolyl group, a pyridothiazolyl group, a pyridoisothiazolyl group, a benzothienyl group; and a tricyclic group such as a 2-benzo[g]quinolyl group, a 2-pyrido[g]quinolyl group, a 2-benzo[g]quinazolinyl group, a 2-pyrido[g]quinazolinyl group, a 3-benzo[g]-cinnolyl group, a 3-pyrido[g]cinnolyl group, a 2-benzo[g]quinoxaloyl group, a 2-pyrido[g]quinoxaloyl group. Of those, preferred are a benzofuranyl group, an indolyl group, a quinolinyl group, an isoquinolinyl group, a benzoxazolyl group, a benzimidazolyl group, a phthalazinyl group, a naphthyridinyl group, an quinoxalinyl group, a quinazolinyl group, a cinnolinyl group, an imidazopyridinyl group; and more preferred are a quinolinyl group, an isoquinolinyl group, a benzoxazolyl group, a benzimidazolyl group, a phthalazinyl group, a naphthyridinyl group, a quinoxalinyl group, a quinazolinyl group, a cinnolinyl group, an imidazopyridinyl group.

The 3-membered to 8-membered heterocyclic group for $Q^1$ may be the same as those mentioned hereinabove. Of those, preferred are an oxetanyl group, a tetrahydrofuranyl group, a tetrahydropyranyl group, a pyrrolidinyl group, a piperidinyl group, a homopiperidinyl group, a morpholinyl group, a homomorpholinyl group; and more preferred are an oxetanyl group, a tetrahydrofuranyl group, a tetrahydropyranyl group, a piperidinyl group, a homopiperidinyl group.

The bicyclic group formed through condensation of a monocyclic 3-membered to 8-membered heterocyclic group and a benzene ring or a pyridine ring for $Q^1$ includes, for example, a 1-benzo[b]azetidinyl group, a 2-benzo[c]azetidinyl group a 1-benzo[b]pyrrolidinyl group, a 2-benzo[d]pyrrolidinyl group, a 3-benzo[d]pyrrolidinyl group, a 1-benzo[b]piperidino group, a 2-benzo[e]piperidyl group, a 3-benzo[e]piperidyl group, a 4-benzo[b]piperidyl group, a 1-benzo[c]hexamethyleneiminyl group, a 2-benzo[d]hexamethyleneiminyl group, a 3-benzo[e]hexamethyleneiminyl group, a 4-benzo[f]hexamethyleneiminyl group, a 1-benzo[e]heptamethyleneiminyl group, a 2-benzo[e]heptamethyleneiminyl group, a 3-benzo[c]heptamethyleneiminyl group, a 4-benzo[c]heptamethyleneiminyl group, a 1-benzo[d]pyrazolidinyl group, a 3-benzo[d]pyrazolidinyl group, a 4-benzo[d]pyrazolidinyl group, a 1-benzo[b]piperazinyl group, a 2-benzo[b]piperazinyl group, a 1-benzo[b]homopiperazinyl group, a 2-benzo[e]homopiperazinyl group, a 5-benzo[f]homopiperazinyl group, a 6-benzo[b]homopiperazinyl group, a 2-pyrido[b]tetrahydrofuranyl group, a 3-pyrido[b]tetrahydrofuranyl group, 2-pyrido[b]tetrahydropyranyl group, 3-pyrido[d]tetrahydropyranyl group, a 4-pyrido[b]tetrahydropyranyl group, a 2-pyrido[e]morpholinyl group, a 3-pyrido[e]morpholinyl group, a pyrido[b]morpholino group, a 2-benzo[d]thiazolidinyl group, a 3-benzo[d]thiazolidino group.

Of the substituents mentioned hereinabove, the substituent that the optionally-condensed 3-membered to 8-membered heterocyclic group for $Q^1$ may have is preferably a cyano group, a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a carbamoyl group, a lactam ring, a trifluoromethyl group, a mono-lower alkylamino group, a di-lower alkylamino group and an alkanoyl group, more preferably a hydroxyl group, a lower alkyl group (the lower alkyl group may be further substituted with a hydroxyl group, a halogen atom or an amino group), a lower alkoxy group (the lower alkoxy group may be further substituted with a halogen atom), a halogen atom, a mono-lower alkylcarbonyloxy group, a di-lower alkylcarbamoyloxy group, a mono-lower alkylcarbamoyl group, a di-lower alkylcarbamoyl group, a cycloalkyliminocarbamoyl group, a lactam ring, a mono-lower alkylamino group, a di-lower alkylamino group and an alkanoyl group. "Lower alkyl group", "lower alkoxy group", "halogen atom", "mono-lower alkylcarbonyloxy group", "di-lower alkylcarbamoyloxy group", "mono-lower alkylcarbamoyl group", "di-lower alkylcarbamoyl group", "lactam ring", "mono-lower alkylamino group", and "di-lower alkylamino group" in the 3-membered to 8-membered heterocyclic group for $Q^1$ are concretely the same as those mentioned hereinabove. The 3-membered to 8-membered heterocyclic group and the bicyclic or tricyclic group formed through condensation of the heterocyclic group with a benzene or pyridine ring for $Q^1$ may have 1 or 2 these substituents at their bondable positions.

Y in formula (II) is preferably the following (1) and (2):

Case (1):

Y in formula (II) is preferably a group of the following general formula (V):

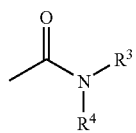

(IV)

Y of formula (V) preferably includes the following 4 embodiments.

The first embodiment is as follows: In formula (IV), $R^3$ represents a hydrogen atom or a lower alkyl group, and $R^4$ represents a group of the following general formula (V):

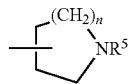

(V)

(wherein $R^5$ represents a hydrogen atom, a lower alkyl group, a C3 to C8 cycloalkyl group, an aralkyl group or a heteroaryl group; n indicates 0 or an integer of from 1 to 4). In formula (IV), the alkyl group for $R^3$ concretely includes a methyl group, an ethyl group. The group for $R^3$ is preferably a methyl group, a hydrogen atom or an ethyl group in that order. The lower alkyl group for R⁵ in formula (V) that represents R⁴ includes a methyl group, an ethyl group. The aralkyl group concretely includes the same as those mentioned hereinabove. The C3 to C8 cycloalkyl group may be the same as those mentioned hereinabove for the above-mentioned C3 to C9 cycloalkyl group, but excepting a cyclononyl group. The heteroaryl group may be a 5-membered or 6-membered monocyclic heteroaryl group having a hetero atom selected from the group consisting of an oxygen atom, a sulfur atom and a nitrogen atom, and it may include the same as those mentioned hereinabove for the above-mentioned heteroaryl group.

The second embodiment is as follows: In formula (IV), $R^3$ represents a hydrogen atom or a lower alkyl group, $R^4$ represents a group of the following general formula (V):

—(CH$_2$)$_q$-A     (VI)

(wherein A represents an aryl group, a heteroaryl group, a condensed bicyclic group of a C4 to C7 cycloalkyl group and an aryl group, or a condensed bicyclic group of a C4 to C7 cycloalkyl group and a heteroaryl group; q indicates 0 or an integer of from 1 to 3). In formula (IV), the lower alkyl group for $R^3$ concretely includes a methyl group, an ethyl group. The aryl group and the heteroaryl group for A in formula (VI) that represents $R^3$ concretely includes the same as those mentioned hereinabove. The C4 to C7 cycloalkyl group concretely includes a cyclobutyl group, a cyclopentyl group, a cyclohexyl group, a cycloheptyl group.

The third embodiment is as follows: In formula (IV), $R^3$ and $R^4$ form a nitrogen containing heterocyclic group along with the nitrogen atom bonding to them. The nitrogen-containing heterocyclic group may be a monocyclic group, including, for example, a piperidinyl group, a pyrrolidinyl group, an azetidinyl group, a homopiperidinyl group, a heptamethyleneiminyl group.

The fourth embodiment is as follows: The nitrogen-containing heterocyclic group in the third embodiment is condensed with a phenyl group or a pyridyl group to form a bicyclic group. The bicyclic group may include the same as those mentioned hereinabove for the above-mentioned heterocyclic group.

When Y in formula (II) indicates any of the above-mentioned for 4 embodiments, then the aromatic ring in formula (I) to which Y bonds is preferably a phenyl group where $X^1$ and $X^2$ are both CH; or a pyridyl group where any of them is a nitrogen atom Case (2):

Y in formula (II) is preferably an aryl group or a 5-membered or 6-membered heteroaryl group, which is unsubstituted or has, in the ring thereof, 1 or 2 substituents selected from a group consisting of a lower alkyl group, a lower alkoxy group, a hydroxyl group and a halogen atom, and may have, in the ring thereof, from 1 to 3 hetero atoms selected from a group consisting of a nitrogen atom, a sir atom and an oxygen atom. The aryl group or the 5-membered or 6-membered heteroaryl group may include the same as those mentioned hereinabove for the aryl group or the 5-membered or 6-membered heteroaryl group for $R^5$ in formula (V) or for A in formula (VI). The substituent in the ring of the aryl group or the 5-membered or 6-membered heteroaryl group includes, for example, a lower alkyl group such as a methyl group, an ethyl group; a lower alkoxy group such as a methoxy group, an ethoxy group; a halogen atom such as a fluorine atom, a chlorine atom, an iodine atom; and a hydroxyl group. When Y in formula (II) is an aryl group or a heteroaryl group that is unsubstituted or has the above-mentioned substituent, then the aromatic ring which bonds to the 1-position of the piperidine ring in formula (I) and to which Y bonds is preferably a pyrimidine ring where $X^1$ and $X^2$ are both nitrogen atoms.

Concretely, the piperidine derivatives of formula (I) include compounds listed in Table 1 to Table 5.

TABLE 1

| $X^1$ | $X^2$ | Heterocyclic Group Bonding to Piperidine Ring | $R^1$ | $R^2$ |
|---|---|---|---|---|
| CH | CH | —N⟨azetidinyl⟩ | H | H |
| N | N | —N⟨pyrrolidinyl⟩ | F | F |
|  |  | —N⟨piperidinyl⟩ |  | —CH$_3$ |
|  |  | —N⟨morpholinyl⟩ |  | —COCH$_3$ |
|  |  | —N⟨azepanyl⟩ |  | —OCF$_3$ |
|  |  | —N⟨azocanyl⟩ |  |  |

| Y |
|---|
| —CH$_3$ |
| —C$_2$H$_5$ |
| —C$_3$H$_7$ |
| —C$_4$H$_9$ |
| —C(CH$_3$)C$_2$H$_5$ |
| —C$_5$H$_{11}$ |
| —CH$_2$CH(CH$_3$)C$_2$H$_5$ |
| —C(CH$_3$)HC$_3$H$_7$ |
| —C$_6$H$_{13}$ |
| cyclopropyl |
| cyclobutyl |
| cyclopentyl |

TABLE 1-continued
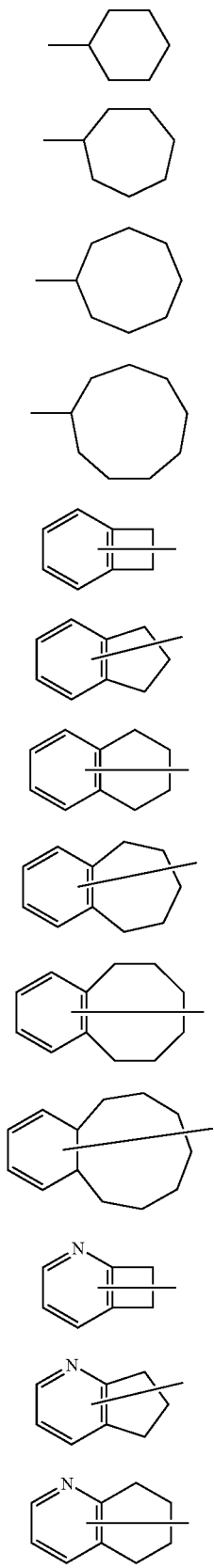
TABLE 1-continued
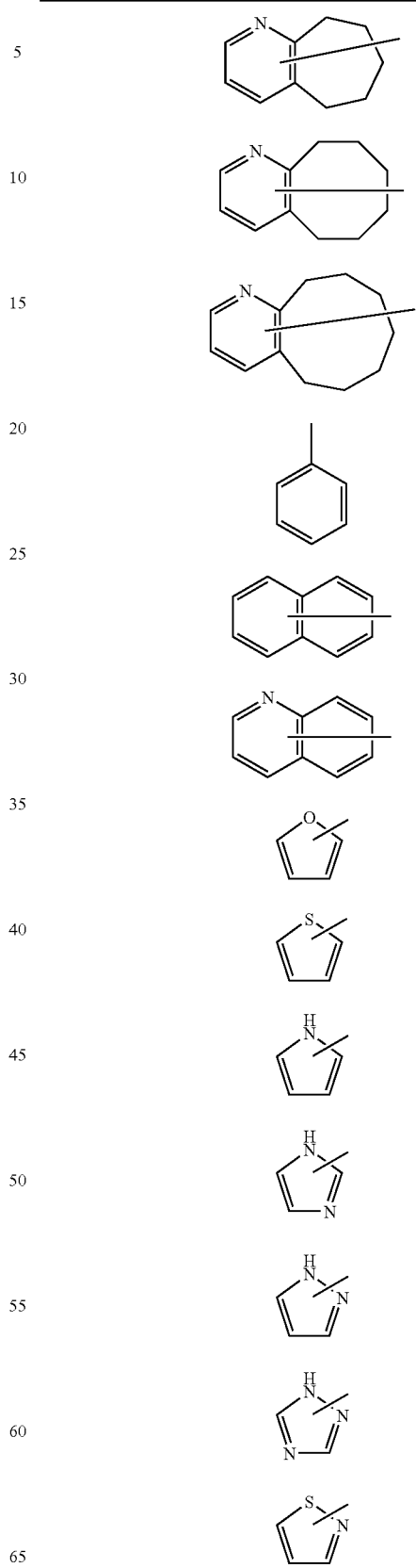

TABLE 1-continued
| | | |
|---|---|---|
|  | 5 | 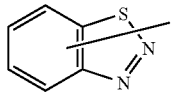 |
|  | 10 | 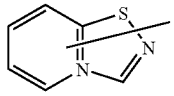 |
|  | 15 | 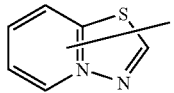 |
|  | 20 | 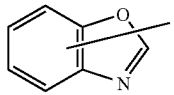 |
|  | 25 | 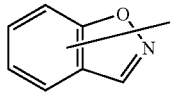 |
| 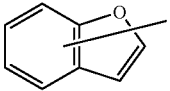 | 30 | 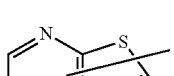 |
| 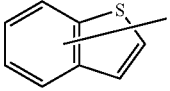 | 35 | 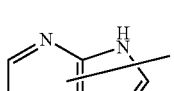 |
| 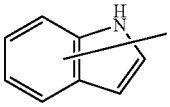 | 40 | 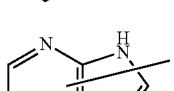 |
| 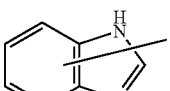 | 45 | 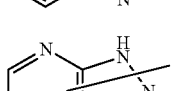 |
| 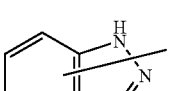 | 50 | 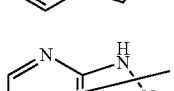 |
| 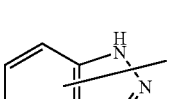 | 55 | 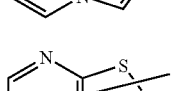 |
| 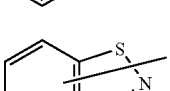 | 60 | 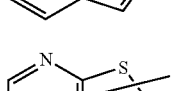 |
| 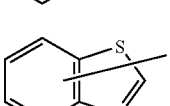 | 65 | 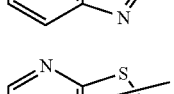 |

TABLE 1-continued
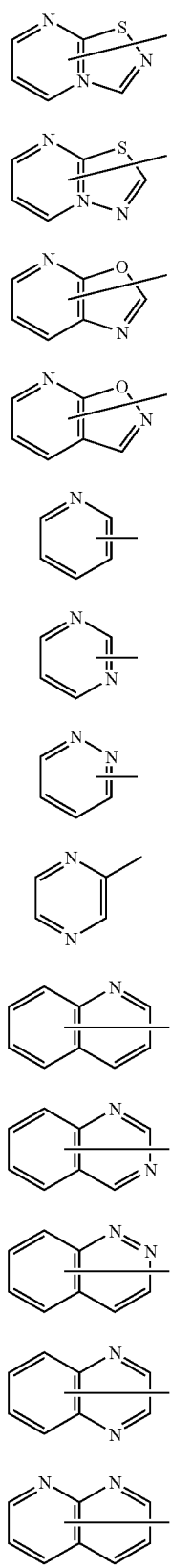
TABLE 1-continued
Substituent for Y
—CN
—OH
—OCH₃
—OC₂H₅
—OCH₂Cl
—OCH₂F
—OC₂H₄Cl
—OC₂H₄F
—NH₂
—F
—Cl
—CONH(CH₃)
—CONH(C₂H₅)
—OCON(CF₃)₂
—OCON(C₂H₅)₂
—OCON(C₂H₅)(CH₃)
—CF₃

TABLE 1-continued
—CN
—OH
—CH$_3$
—C$_2$H$_5$
—CH$_2$Cl
—CH$_2$OH
—CH$_2$(NH$_2$)
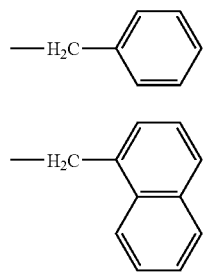
—F
—Cl
—OCOCH$_3$
—OCOCH$_2$F
—OCOCH$_2$Cl
—OCOC$_2$H$_4$F
—OCOC$_2$H$_4$Cl
—CONH$_2$
—CONH(CH$_3$)
—CONH(C$_2$H$_5$)
—CON(C$_3$H$_7$)$_2$
—CON(C$_3$H$_7$)(CH$_3$)
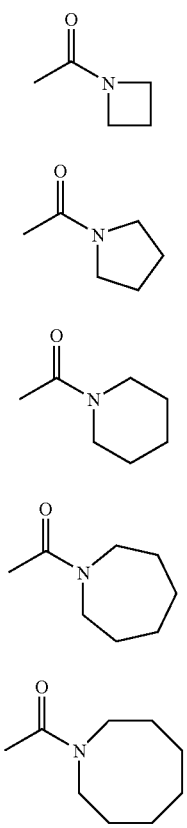
TABLE 1-continued
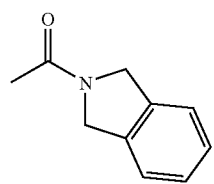
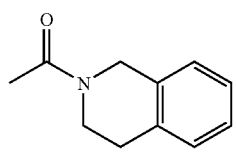
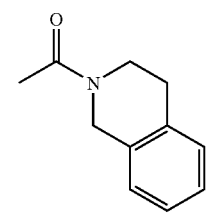
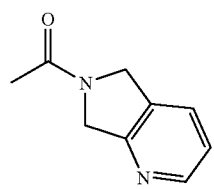
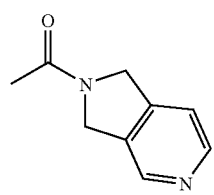
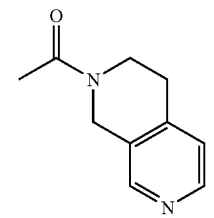
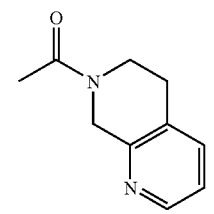
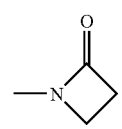

TABLE 1-continued
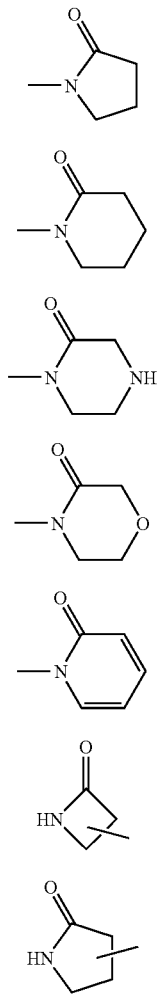
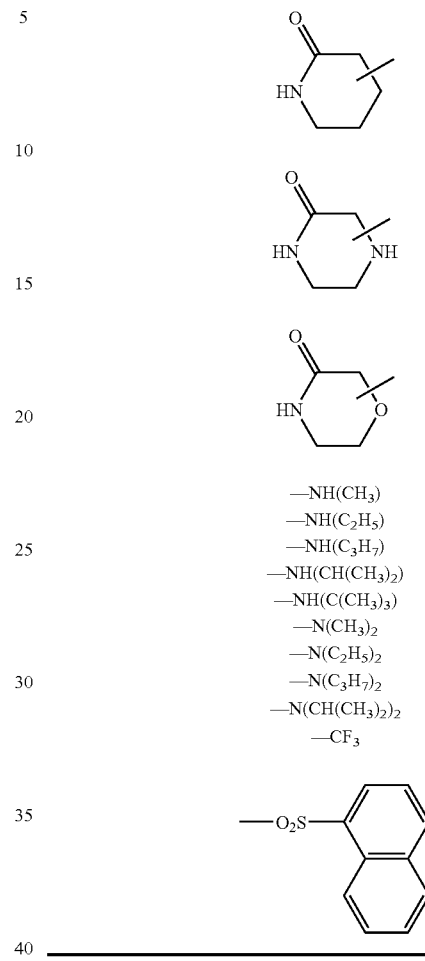
—NH(CH$_3$)
—NH(C$_2$H$_5$)
—NH(C$_3$H$_7$)
—NH(CH(CH$_3$)$_2$)
—NH(C(CH$_3$)$_3$)
—N(CH$_3$)$_2$
—N(C$_2$H$_5$)$_2$
—N(C$_3$H$_7$)$_2$
—N(CH(CH$_3$)$_2$)$_2$
—CF$_3$
TABLE 2
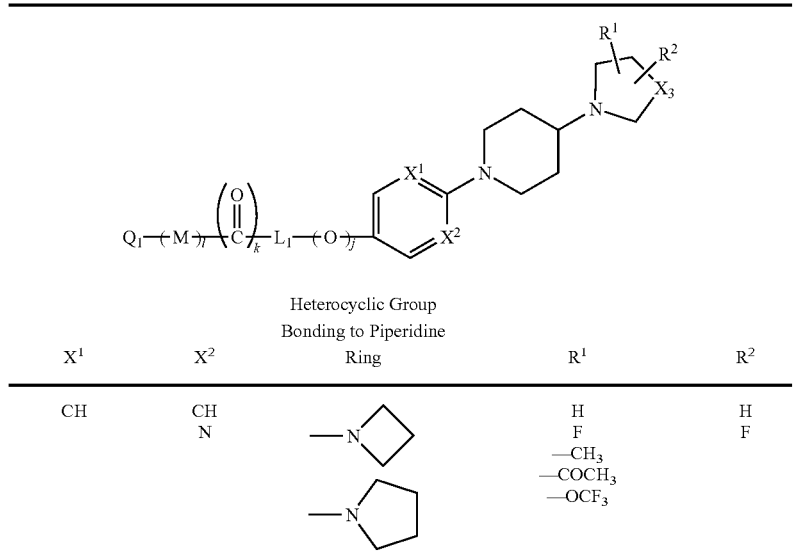
| X$^1$ | X$^2$ | Heterocyclic Group Bonding to Piperidine Ring | R$^1$ | R$^2$ |
|---|---|---|---|---|
| CH | CH | azetidinyl; pyrrolidinyl | H<br>F<br>—CH$_3$<br>—COCH$_3$<br>—OCF$_3$ | H<br>F |
|  | N |  |  |  |

TABLE 2-continued

| | $Q_1$ |
|---|---|
| $-\!(\!O\!)_j\!-\!L_1\!-\!\left(\!\!\begin{array}{c}O\\\|\\C\end{array}\!\!\right)_k\!-\!(M)_l\!-$ | |
| $-(CH_2)_n-$ <br> (n = 1~3) <br> $-O-$ | $-CH_3$  $-C_2H_5$  $-C_3H_7$  $-C_4H_9$ <br> $-C(CH_3)C_2H_5$  $-C_5H_{11}$ <br> $-CH_2CH(CH_3)C_2H_5$  $-C(CH_3)HC_3H_7$ <br> $-C_6H_{13}$ |
| $-(CO)-O-$ <br> $-(CO)-(NR^O)-$ <br> $-(CH_2)_n-(CO)-O-$ <br> $-(CH_2)_n-(CO)-(NR^O)-$ <br> $-O-(CH_2)_n-$ | (cyclopropyl) <br> (cyclobutyl) <br> (cyclopentyl) <br> (cyclohexyl) <br> (cycloheptyl) <br> (cyclooctyl) <br> (cyclononyl) <br> (benzocyclobutyl) <br> (indanyl) |

TABLE 2-continued
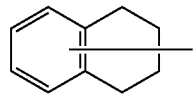
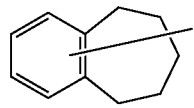
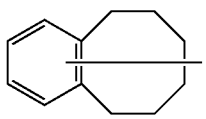
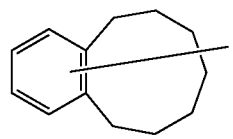
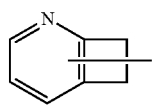
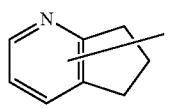
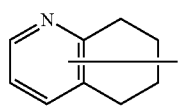
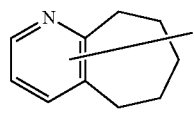
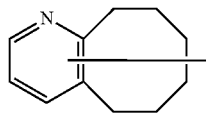
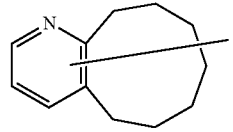
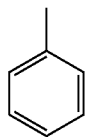
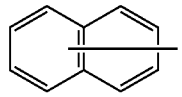

TABLE 2-continued
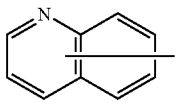
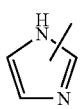
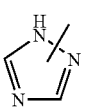
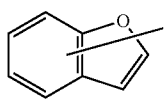

TABLE 2-continued
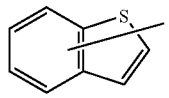
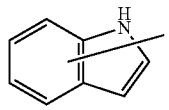
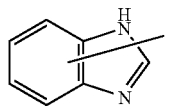
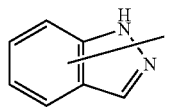
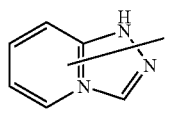
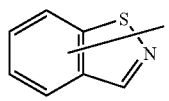
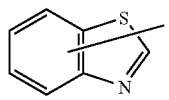
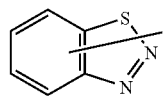
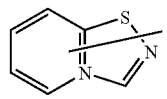
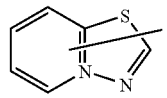
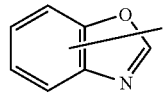
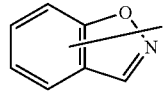
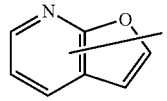
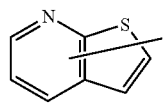

TABLE 2-continued
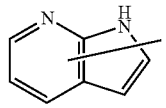
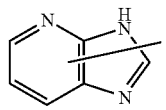
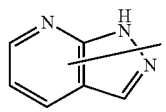
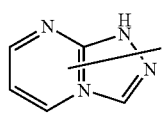
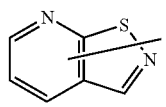
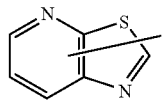
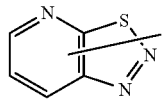
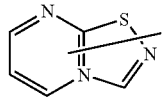
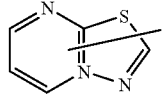
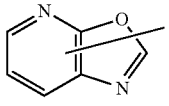
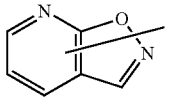
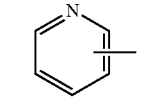
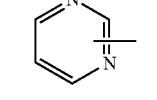

TABLE 2-continued
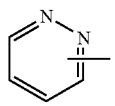
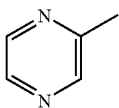
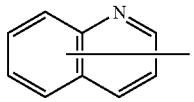
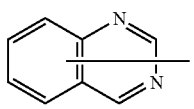
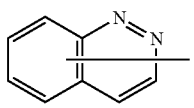
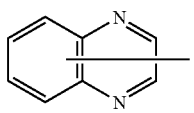
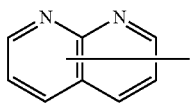
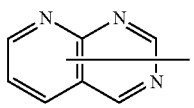
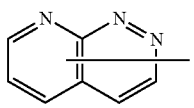
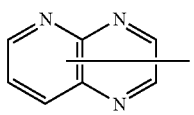
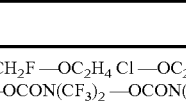
Substituent for Q1
—CN —OH —OCH$_3$ —OC$_2$H$_5$ —OCH$_2$Cl —OCH$_2$F —OC$_2$H$_4$Cl —OC$_2$H$_4$F —NH$_2$ —F —Cl —CONH(CH$_3$) —CONH(C$_2$H$_5$) —OCON(CF$_3$)$_2$ —OCON(C$_2$H$_5$)$_2$ —OCON(C$_2$H$_5$)(CH$_3$) —CF$_3$
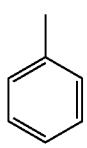
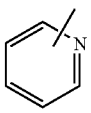

TABLE 2-continued
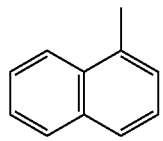
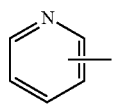
—CN —OH —CH$_3$ —C$_2$H$_6$ —CH$_2$Cl —CH$_2$OH —CH$_2$(NH$_2$)
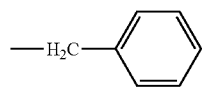
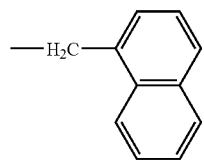
—F —Cl —OCOCH$_3$ —OCOCH$_2$F —OCOCH$_2$Cl —OCOC$_2$H$_4$F
—OCOC$_2$H$_4$Cl —CONH$_2$ —CONH(CH$_3$) —CONH(C$_2$H$_5$) —CON(C$_3$H$_7$)$_2$ —CON(C$_3$H$_7$)(CH$_3$)
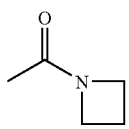
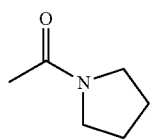
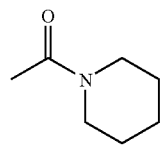
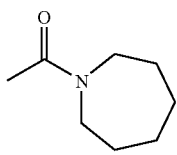

TABLE 2-continued
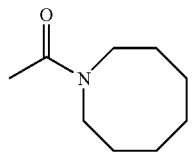
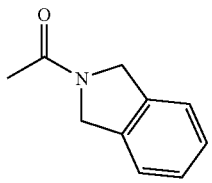
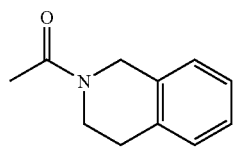
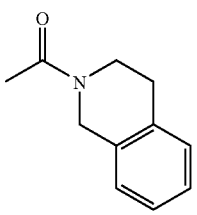
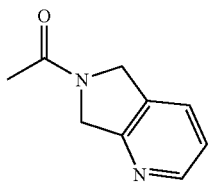
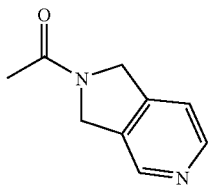
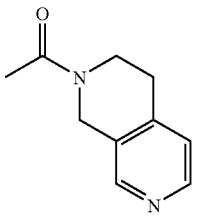
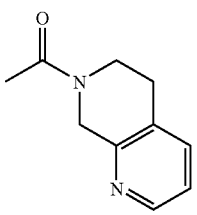

TABLE 2-continued
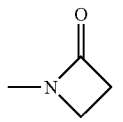
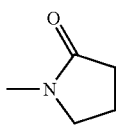
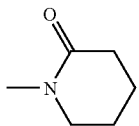
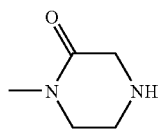
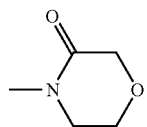
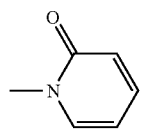
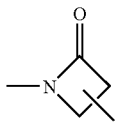
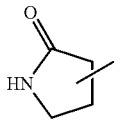
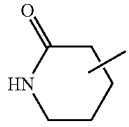
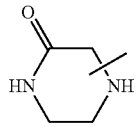
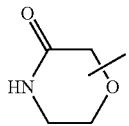
—NH(CH$_3$)  —NH(C$_2$H$_5$)  —NH(C$_3$H$_7$)  —NH(CH(CH$_3$)$_2$)  —NH(C(CH$_3$)$_3$)  —N(CH$_3$)$_2$
—N(C$_2$H$_5$)$_2$  —N(C$_3$H$_7$)$_2$  —N(CH(CH$_3$)$_2$)$_2$  —CF$_3$ TABLE 2-continued
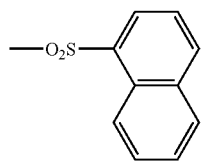
TABLE 3
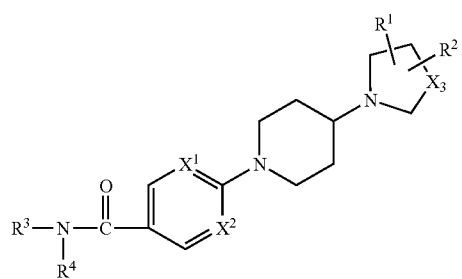
| X¹ | X² | X³ | R¹ | R² | R³ | R⁴ | | R⁵ | |
|---|---|---|---|---|---|---|---|---|---|
| CH | CH | ![piperidine] | H | H | —CH₃ | ![azetidine-NR⁵] | | —CH₃ | —C₂H₅ —C₃H₇ —C₄H₉ |
| N | | | F | F | —H | ![pyrrolidine-NR⁵] | | —C(CH₃)C₂H₅ | —C₅H₁₁ |
| | | | —CH₃ | —C₂H₅ | | ![piperidine-NR⁵] | | —CH₂(CH₃)C₂H₅ | —C(CH₃)HC₃H₇ |
| | | —COCH₃ | | | | ![azepane-NR⁵] | | —C₆H₁₃ | ![cyclopropyl] |
| | | —OCF₃ | | | | ![azocane-NR⁵] | | ![cyclobutyl] | ![cyclopentyl] |
| | | | | | | | | ![cyclohexyl] | ![cycloheptyl] |
| | | | | | | | | ![cyclooctyl] | ![cyclononyl] |
| | | | | | | | | —H₃C—C₆H₄— | —C₂H₅—C₆H₄— |

TABLE 3-continued
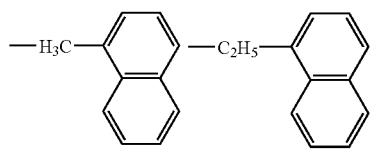
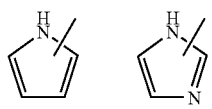
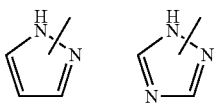
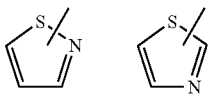
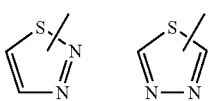
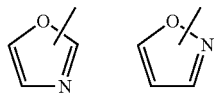
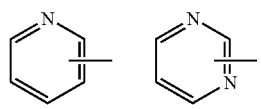
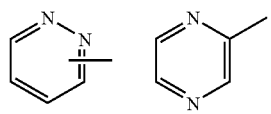
| $X^1$ | $X^2$ | $X^3$ | $R^1$ | $R^2$ | $R^3$ | $R^4$ | A |
|---|---|---|---|---|---|---|---|
| CH | CH | ―N⟨piperidine⟩ | H | H | ―CH$_3$ | H | phenyl, naphthyl |
| N | | | F | F | ―H | ―(CH$_2$)$_{1-3}$―A | benzocyclobutenyl, indanyl |
| | | | ―CH$_3$ | ―C$_2$H$_5$ | | | tetrahydronaphthyl, benzocycloheptyl |

TABLE 3-continued
—COCH₃
—OCF₃
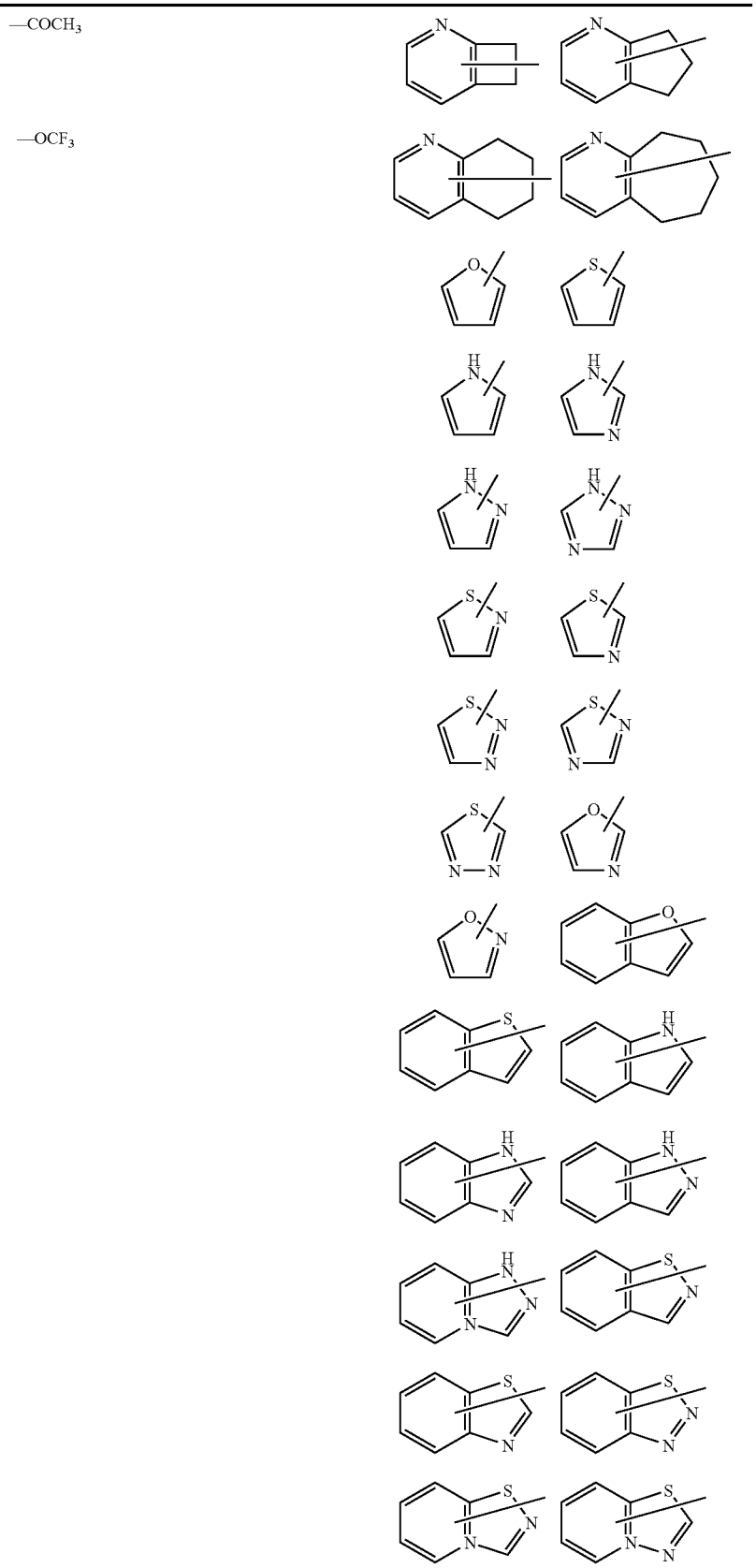

TABLE 3-continued
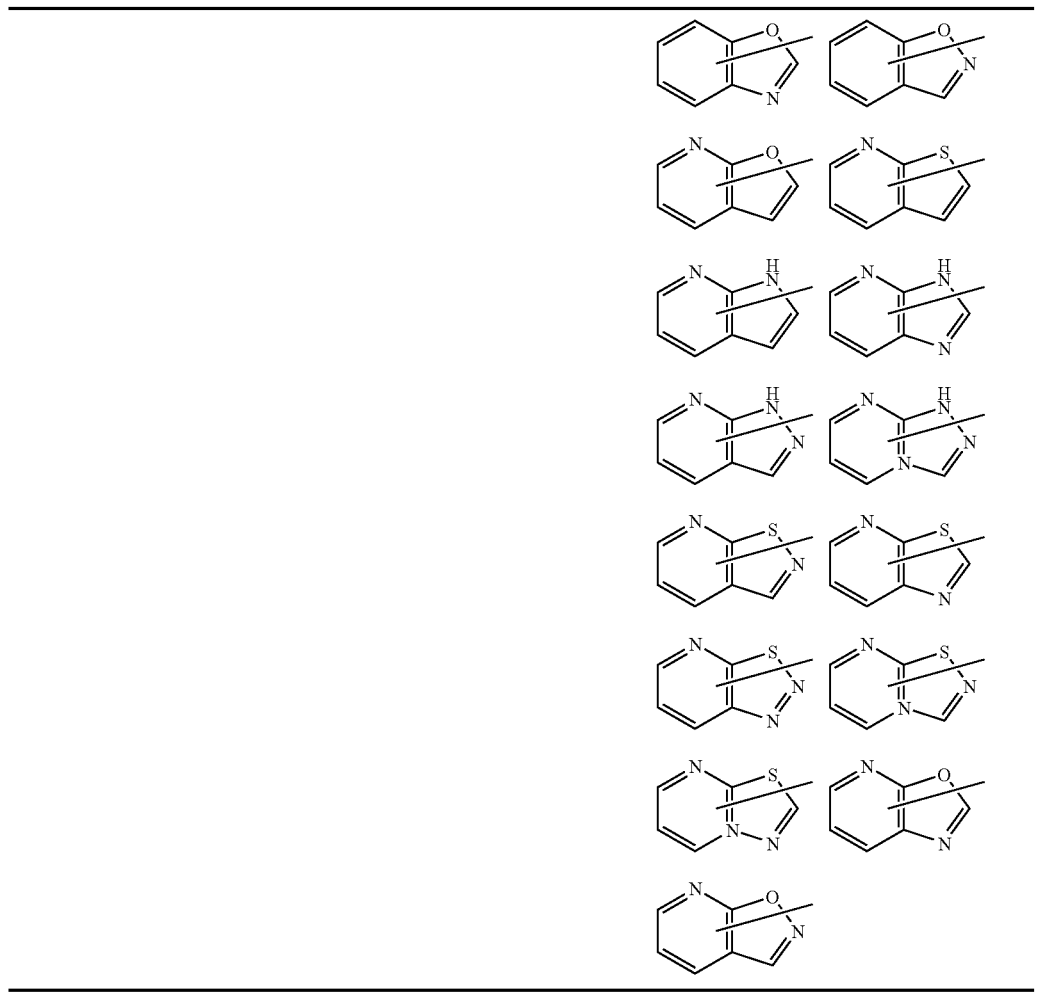
| TABLE 4 | | | | | |
|---|---|---|---|---|---|
| 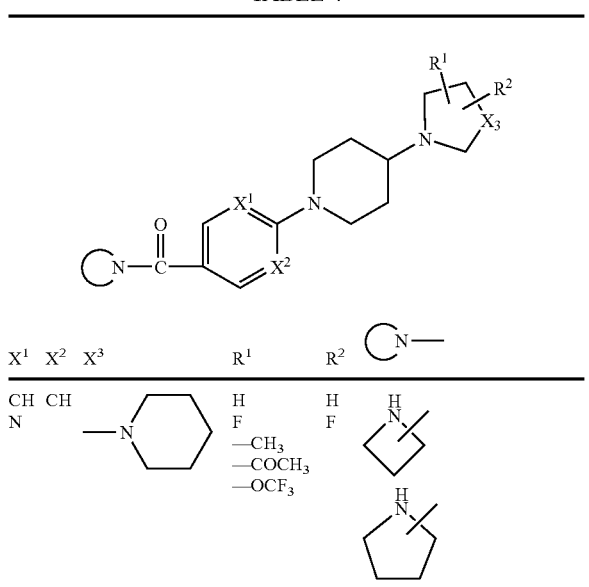 | | | | | |
| $X^1$ | $X^2$ | $X^3$ | $R^1$ | $R^2$ | ⟨N−⟩ |
| CH | CH | N | *N-piperidinyl* | H<br>F<br>—CH$_3$<br>—COCH$_3$<br>—OCF$_3$ | H<br>F | *azetidinyl*<br>*pyrrolidinyl* |
| TABLE 4-continued | | | | | |
|---|---|---|---|---|---|
| 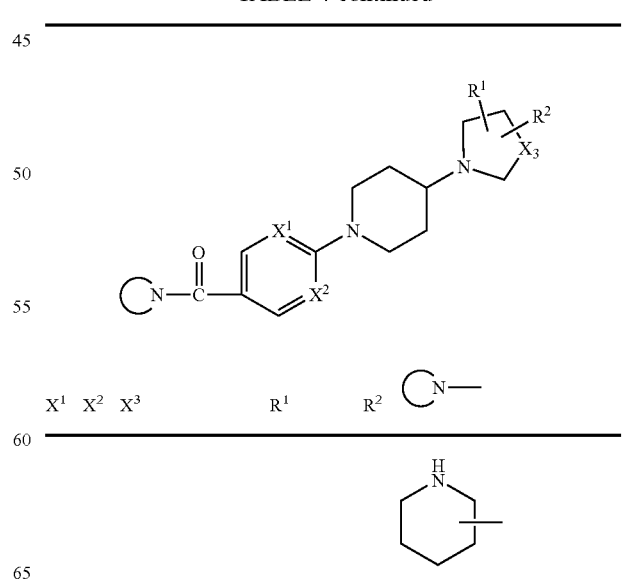 | | | | | |
| $X^1$ | $X^2$ | $X^3$ | $R^1$ | $R^2$ | ⟨N−⟩ |
| | | | | | *piperidinyl* |

TABLE 4-continued
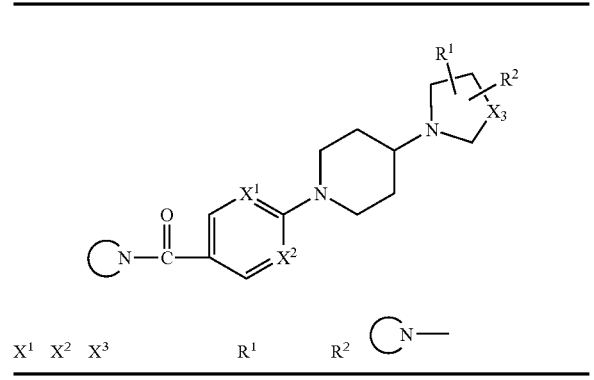
TABLE 4-continued
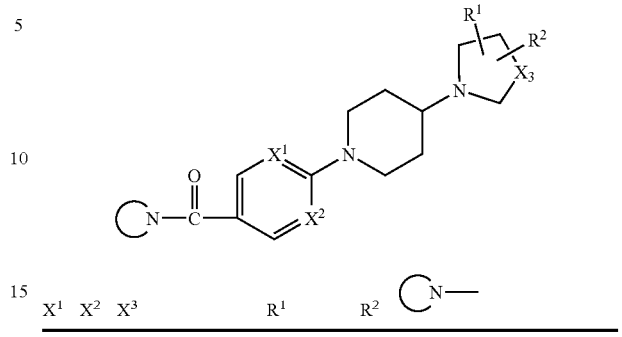
TABLE 5
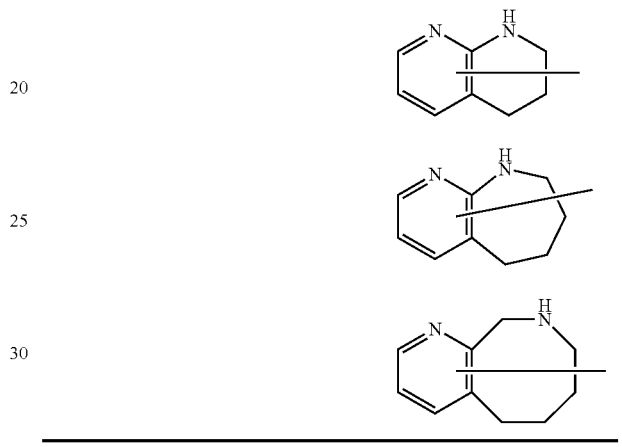
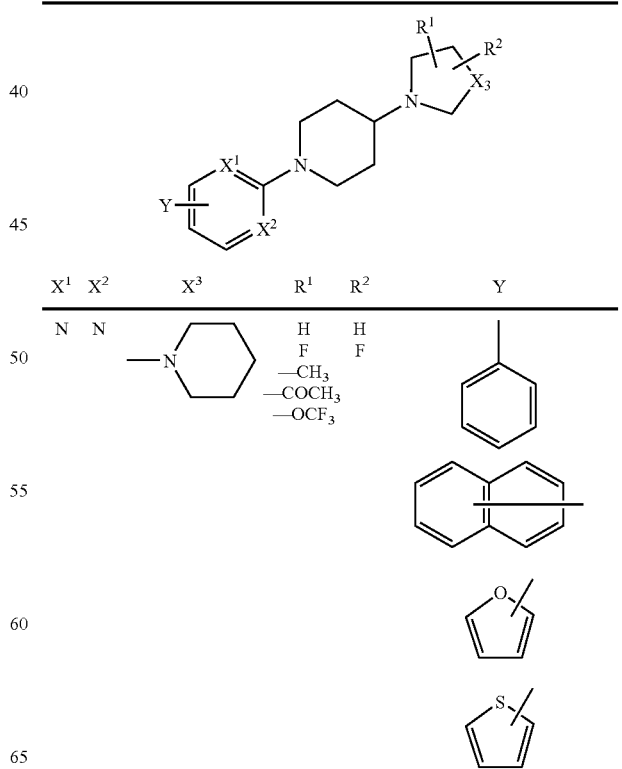

TABLE 5-continued

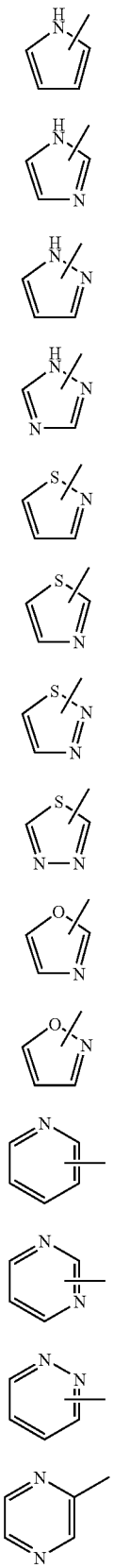

| Substituent for Y |
|---|
| —CH₃ —C₂H₅ —C₃H₇ —C₄H₉ —C(CH₃)C₂H₅ —C₅H₁₁ |
| —CH₂CH(CH₃)C₂H₅ —C(CH₃)HC₃H₇ —C₆H₁₃ |
| CH₃CO— |
| C₂H₅CO— |
| OH |
| Cl F |

Of those piperidine derivatives, preferred are the following:

N-methyl-N-(1-methylpiperidin-4-yl)-4-[4-(piperidin-1-ylpiperidin-1-yl]benzamide (1),
N-(1-methylpiperidin-4-yl)-4-[4-(piperidin-1-yl)piperidin-1-yl]benzamide (2),
N-methyl-N-(1-cyclobutylpiperidin-4-yl)-4-[4-(piperidin-1-yl)piperidin-1-yl]benzamide (3),
N-methyl-N-(1-cyclopentylpiperidine-4-yl)-4-[4-(piperidin-1-yl)piperidin-1-yl]benzamide (4),
N-methyl-N-(1-cyclohexylpiperidin-4-yl)-4-[4-(piperidin-1-yl)piperidin-1-yl]benzamide (5),
N-methyl-N-(1-cyclohexylmethylpiperidin-4-yl)-4-[4-(piperidin-1-yl)piperidin-1-yl]benzamide (6),
N-methyl-N-[(3R)-1-cyclopentylpyrrolidin-3-yl]-4-[4-(piperidin-1-yl)piperidin-1-yl]benzamide (7),
N-methyl-N-[(3S)-1-cyclopentylpyrrolidin-3-yl)]-4-[4-(piperidin-1-yl)piperidin-1-yl]benzamide (8),
N-methyl-N-[(3R)-1-benzylpyrrolidin-3-yl)]-4-[4-(piperidin-1-yl)piperidin-1-yl]benzamide (9),
N-methyl-N-[(3R)-1-benzylpyrrolidin-3-yl)]-4-[4-(piperidin-1-yl)piperidin-1-yl]benzamide (10),
N-(pyridin-4-yl)-4-[4-(piperidin-1-yl)piperidin-1-yl]benzamide (11),
2-{4-(4-piperidin-1-yl)piperidin-1-yl]benzoyl-1,2,3,4-tetrahydroisoquinoline (12),
1-{4-(4-piperidin-1-yl)piperidin-1-yl]benzoyl-1,2,3,4-tetrahydroquinoline (13),
1-{4-(4-piperidin-1-yl)piperidin-1-yl]benzoyl-4-phenylpiperazine (14),
N-methyl-N-[1-(pyrimidin-2-yl)piperidin-4-yl]-4-[4-(piperidin-1-yl)piperidin-1-yl]benzamide (15),
N-methyl-N-(thiophen-2-yl)methyl-4-[4-(piperidin-1-yl)piperidin-1-yl]benzamide (16),
N-methyl-N-phenethyl-4-[4-(piperidin-1-yl)piperidin-1-yl]benzamide (17),
1-{4-(4-piperidin-1-yl)piperidin-1-yl]benzoyl-3-(3,4-difluorophenyl)pyrrolidine (18),
1-{4-(4-piperidin-1-yl)piperidin-1-yl]benzylpiperidin (19),
N-methyl-N-(1-methylpiperidin-4-yl)-4-[4-(pyrrolidin-1-yl)piperidin-1-yl]benzamide (20).

Also preferably, the piperidine derivatives of the invention are the following:

N-methyl-N-(1-methylpiperidin-4-yl)-4-[4(azetidin-1-yl)piperidin-1-yl]benzamide (21),
N-methyl-N-(1-methylpiperidin-4-yl)-5-[4(piperidin-1-yl)piperidin-1-yl]pyridine-2-carboxamide (22),
N-methyl-N-(1-methylpiperidin-4-yl)-4-[4-(4,4-difluoropiperidin-1-yl)piperidin-1-yl]benzamide (23),
2-[(4-piperidin-1-yl)piperidin-1-yl]-5-(4-cyanophenyl)-pyrimidine (24),
2-[(4-piperidin-1-yl)piperidin-1-yl]-5-(3-pyridyl)pyrimidine (25),
2-[4-(piperidin-1-yl)piperidin-1-yl]-5-(3-trifluoromethylphenyl)pyridine (26),
2-[4-(piperidin-1-yl)piperidin-1-yl]-5-(3,5-dichlorophenyl)pyrimidine (27),
2-[4-(piperidin-1-yl)piperidin-1-yl]-5-(2-naphthyl)pyrimidine (28), 2-[4-(piperidin-1-yl)piperidin-1-yl]-5-[4-(pyrrolidin-1-yl-carbonyl)phenyl]pyrimidine (29), 1-[4(piperidin-1-yl)piperidin-1-yl]-4-(3-pyridyl)benzene (30), 1-(piperidin-1-ylmethyl)-4-[4-(piperidin-1-yl)piperidin-1-yl]benzene (31).

Not specifically defined, pharmaceutically-acceptable salts of piperidine derivatives of formula (I) are, for example, hydrohalides such as hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzesulfonates, p-toluenesulfonates; organic acid salts such as fumarates, succinates, citrates, tartrates, oxalates, maleates; and other acid-addition salts with organic acids such as amino acids, for example, glutamates, aspartates. The salts may also be base-addition salts, for example, salts with alkali metals such as sodium, potassium; salts with alkaline earth metals such as calcium, magnesium; ammonium salts; salts with organic bases such as guanidine, triethylamine, dicyclohexylamine. Further, the piperidine derivatives of formula (I) of the invention may be in the form of their esters, or hydrates or solvates of their free compounds or pharmaceutically-acceptable salts or esters.

Methods for producing the piperidine derivatives of formula (I) of the invention are described below. The piperidine derivatives of formula (I) may be produced, using any known reaction methods or according to any per-se known methods. They may be produced not only according to ordinary liquid-phase production methods but also according to any solid-phase methods such as combinatorial production methods or parallel production methods that are being significantly developed these days.

Methods for producing the piperidine derivatives of formula (I) of the invention are described below.

[Production Method 1]

A compound of a general formula (Ia):

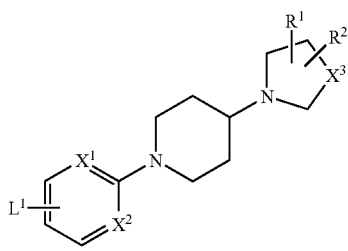

(Ia)

[wherein $X^1$, $X^2$, $X^3$, $R^1$ and $R^2$ have the same meanings as $X^1$, $X^2$, $X^3$, $R^1$ and $R^2$ in formula (I); and $L^1$ represents a leaving group] is reacted with a compound of a general formula (IIa):

(IIa)

[wherein Met represents a metal atom-containing atomic group; and $Y^{1p}$ has the same meaning as Y in a general formula (II):

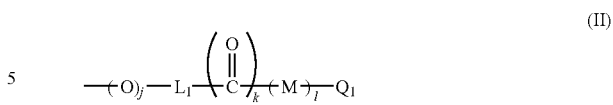

(II)

or represents a group corresponding to it but protected at the amino group, the hydroxyl group or the carboxyl group therein], in the presence of a catalyst to give a compound of a general formula (Ib):

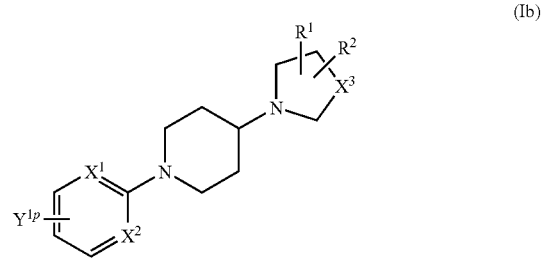

(Ib)

[wherein $X^1$, $X^2$, $X^3$, $R^1$ and $R^2$ have the same meanings as $X^1$, $X^2$, $X^3$, $R^1$ and $R^2$ in formula (Ia); and $Y^{1p}$ has the same meaning as $Y^{1p}$ in formula (IIa)], and optionally the protective group for the functional group of $Y^{1p}$ is removed or converted (e.g., for amine residue acylation, carboxylic acid residue amidation, alcohol residue alkylation) to thereby produce a compound of a general formula (I-1):

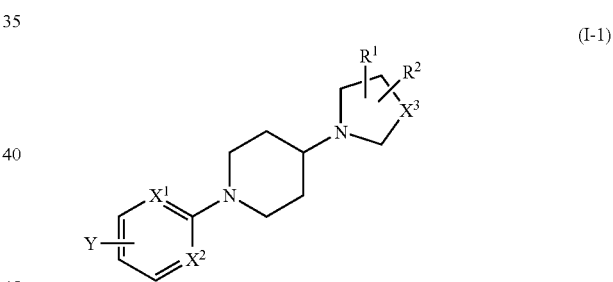

(I-1)

[wherein $X^1$, $X^2$, $X^3$, $R^1$ and $R^2$ have the same meanings as $X^1$, $X^2$, $X^3$, $R^1$ and $R^2$ in formula (Ib); and Y is a group derived from $Y^{1p}$ in formula (Ib) by removing or converting the protective group for the functional group of $Y^{1p}$].

The metal atom-containing atomic group for Met in formula (IIa) is preferably an organic metal-containing atomic group generally used in cross-coupling reaction. The metal atom to be in the metal atom-containing atomic group includes, for example, lithium, boron, silicon, magnesium, aluminium, zinc, tin, more preferably boron, zinc, tin. Regarding the concrete embodiments of the metal atom-containing atomic group, for example, boron is in the form of boric acid or borates; zinc is in the form of zinc chloride, zinc bromide or zinc iodide; and tin is in the form of tri-lower alkyl-tin. $Y^{1p}$ in formula (IIa) that contains a protective group for Y is described hereinunder.

The reaction of producing a compound of formula (Ib) from a compound of formula (Ia) and a compound of formula (IIa) is carried out, generally using from 0.5 mols to 5 mols, preferably from 0.7 mols to 3 mols of the compound (IIa) relative to 1 mol of the compound (Ia). The catalyst for the reaction is, for example, a transition metal generally used in cross-coupling reaction, such as copper, nickel, palladium. More concretely, preferred are tetrakis(triphenylphosphine)palladium(0), palladium(II) acetate, bis(triphenylphosphine)palladium(II) chloride, [1,1'-bis(diphenylphosphino)ferrocene]palladium(II) dichloride. The reaction is effected generally in an inert solvent. The insert solvent is, for example, preferably water, benzene, toluene, xylene, methylene chloride, chloroform, dimethoxyethane, tetrahydrofuran, dioxane, dimethylformamide, and their mixed solvents. The reaction temperature may be generally from room temperature to the boiling point of the solvent used in the reaction, preferably from 20° C. to 200° C. The reaction time may be generally from 30 minutes to 7 days, preferably from 3 hours to 2 days.

Preferably, the reaction of a compound of formula (Ia) and a compound of formula (IIa) is effected in the presence of a base. The base includes, for example, an inorganic base such as sodium hydroxide, potassium hydroxide, sodium hydrogencarbonate, sodium carbonate, potassium carbonate, cesium carbonate; and an organic base such as triethylamine, diisopropylamine. The amount of the base to be used may be generally from 0.5 mols to 5 mols, preferably from 0.7 mols to 3 mols relative to 1 mol of the compound of formula (a).

In the reaction of a compound of formula (Ia) and a compound of formula (IIa), the amino group, the imino group, the hydroxyl group, the carboxyl group, the oxo group or the carbonyl group in the compound of formula (Ia) or in $Y^{1p}$ in formula (IIa) may be protected with a protective group, and then the reaction may be effected, and, after the reaction, the protective group may be removed. The protective group for such an amino group or an imino group may be any one having its own function, including, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group; a tetrahydropyranyl group; a trimethylsilylethoxymethyl group; a lower alkylsulfonyl group such as a methylsulfonyl group, an ethylsulfonyl group; an arylsulfonyl group such as a benzenesulfonyl group, a toluenesulfonyl group. Preferred particularly are an acetyl group, a benzoyl group, a tert-butoxycarbonyl group, a trimethylsilylethoxymethyl group, a methylsulfonyl group and the like.

The protective group for the hydroxyl group not participating in the reaction, in the compound of formula (a) or in $Y^{1p}$ in formula (IIa), may be any one having its own function. For example, it includes a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Preferred particularly are a methyl group, a methoxymethyl group, a tetrahydropyranyl group, a trityl group, a trimethylsilylethoxymethyl group, a tert-butyldimethylsilyl group, an acetyl group and the like.

The protective group for the carboxyl group not participating in the reaction, in the compound of formula (a or in $Y^{1p}$ in formula (IIa), may be any one having its own function. For example, it includes a lower alkyl group such as a methyl group, an ethyl group, a propyl group, an isopropyl group, a tert-butyl group; a halo-lower alkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, a trityl group. Preferred particularly are a methyl group, an ethyl group, a tert-butyl group, a 2-propenyl group, a benzyl group, a p-methoxybenzyl group, a benzhydryl group and the like.

The protective group for the oxo group or the carbonyl group not participating in the reaction, in the compound of formula (Ia) or in $Y^{1p}$ in formula (IIa), may be any one having its own function. For example, it includes acetals and ketals such as ethylene ketal, trimethylene ketal, dimethyl ketal.

The compound of formula (Ib) thus obtained in the manner as above is, after purified or not purified, subjected to removal or conversion of the protective group when $Y^{1p}$ in the formula has a protected amino group, hydroxyl group, carboxyl group, oxo group or carbonyl group, whereby the intended compound of formula (I-1) may be produced. The removal of the protective group may differ, depending on the type of the protective group and on the stability of the intended product compound (I-1). For example, it may be attained through solvolysis with an acid or a base according to methods described in references (see Protective Groups in Organic Synthesis written T. W. Green; published by John Wiley & Sons, 1981) or according to methods similar to these, for example, according to a method of reacting the product with from 0.01 mol to a large excessive amount of an acid, preferably trifluoroacetic acid, formic acid or hydrochloric acid, or with an equimolar amount or a large excessive amount of a base, preferably potassium hydroxide or calcium hydroxide, or through chemical reduction with a metal hydride complex, or through catalytic reduction with a palladium-carbon catalyst or a Raney nickel catalyst or the like.

[Production Method 2]

A compound of a general formula (Ic):

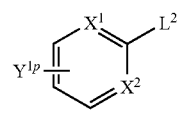

(Ic)

[wherein $X^1$ and $X^2$ have the same meanings as $X^1$ and $X^2$ in formula (I); $Y^{1p}$ has the same meaning as Y in a general formula (II), or represents a group corresponding to it but protected at the ammo group, the hydroxyl group or the carboxyl group therein; and $L^2$ represents a leaving group] is reacted with a compound of a formula (Id):

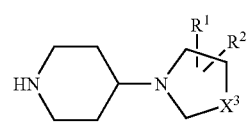

(Id)

[wherein $R^1$, $R^2$ and $X^3$ have the same meanings as $R^1$, $R^2$ and $X^3$ in formula (I)] under a basic condition or in the presence of a catalyst to give a compound of a general formula (Ie):

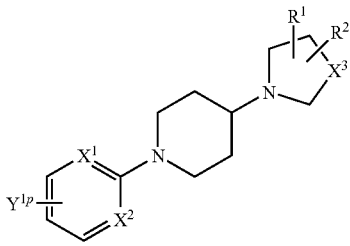

(Ie)

[wherein $X^1$, $X^2$ and $Y^{1p}$ have the same meanings as $X^1$, $X^2$ and $Y^{1p}$ in formula (Ic); $X^3$, $R^1$ and $R^2$ have the same meanings as $X^3$, $R^1$ and $R^2$ in formula (Id)], and optionally the protective group for the functional group of $Y^{1p}$ is removed or converted (e.g., for amine residue acylation, carboxylic acid residue amidation, alcohol residue alkylation) to thereby produce a compound of a general formula (I-2):

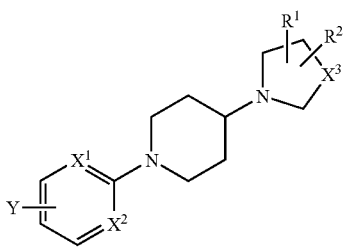

(I-2)

[wherein $X^1$, $X^2$, $X^3$, $R^1$ and $R^2$ have the same meanings as $X^1$, $X^2$, $X^3$, $R^1$ and $R^2$ in formula (Ie); and Y is a group derived from $Y^{1p}$ in formula (Ie) by removing or converting the protective group for the functional group of $Y^{1p}$.

The introduction of a protective group to the functional group not participating in the reaction in the compounds or in $Y^{1p}$, as well as the removal and the conversion of the protective group after the reaction, and the treatment after the reaction may be attained according to the methods described for the Production Method 1.

[Production Method 3]

A compound of a general formula (If):

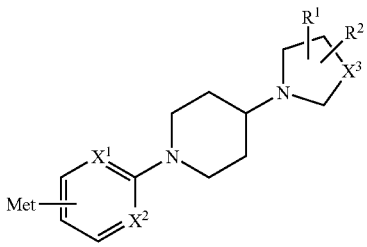

(If)

[wherein $X^1$, $X^2$, $X^3$, $R^1$ and $R^2$ have the same meanings as $X^1$, $X^2$, $X^3$, $R^1$ and $R^2$ in formula (I); Met represents a metal atom-containing atomic group] is reacted with a compound of a general formula (IIb):

$Y^{1p}$-$L_2$ (IIb)

[wherein $Y^{1p}$ has the same meaning as Y in formula (II), or represents a group corresponding to it but protected at the amino group, the hydroxyl group or the carboxyl group therein; and $L^2$ represents an ordinary leaving group], in the presence of a catalyst to give a compound of a general formula (Ig):

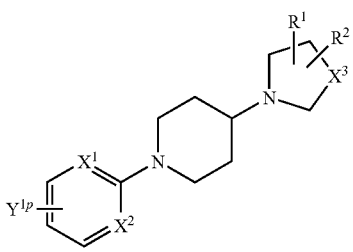

(Ig)

[wherein $X^1$, $X^2$, $X^3$, $R^1$ and $R^2$ have the same meanings as $X^1$, $X^2$, $X^3$, $R^1$ and $R^2$ in formula (If); and $Y^{1p}$ has the same meaning as $Y^{1p}$ in formula (IIb)], and optionally the protective group for the functional group of $Y^{1p}$ is removed or converted (e.g., for amine residue acylation, carboxylic acid residue amidation, alcohol residue alkylation) to thereby produce a compound of a general formula (I-3):

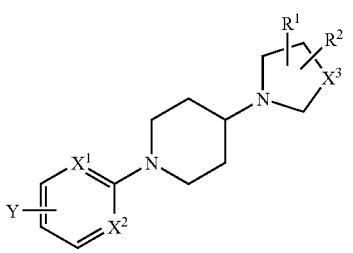

(I-3)

[wherein $X^1$, $X^2$, $X^3$, $R^1$ and $R^2$ have the same meanings as $X^1$, $X^2$, $X^3$, $R^1$ and $R^2$ in formula (Ig); and Y is a group derived from $Y^{1p}$ in formula (Ig) by removing or converting the protective group for the functional group of $Y^{1p}$].

The starting substances, compounds of formula (Ia) and (IIa), as well as compounds of formula (Ic) and (Id), and compounds of formula (IIb) that are used in the above-mentioned production methods may be prepared in known methods or according to such known methods, or according to the methods described in Examples and Reference Examples herein, optionally by suitably combining them.

The compounds of formula (If) that are the starting substance for use in the above-mentioned production methods may be prepared as follows:

1) Reaction of a compound of formula (Ia) with a lower alkyl metal,

2) Reaction of a compound of formula (Ia) with a lower alkyl metal followed by further reaction of the intermediate with a metal halide or an ester, 3) Reaction of a compound of formula (Ia) with, for example, a bis(tri-lower alkyl tin) or bis(boronate) in the presence of a catalyst.

The compounds of formula (Ib), (I-1), (Ie), (I-2), (Ig) or (I-3) produced in the above-mentioned production methods may be readily isolated and purified in any ordinary separation method. The method includes, for example, solvent extraction, recrystallization, column chromatography, preparative thin-layer chromatography.

Pharmaceutically-acceptable salts of the piperidine derivatives of formula (I) may be produced by a method of adding an acid or a base to the piperidine derivative obtained in any of the above-mentioned methods. For producing acid-addition salts of the piperidine derivative, for example, a hydrohalic acid such as hydrochloric acid, hydrofluoric acid, hydrobromic acid or hydroiodic acid, or an inorganic acid such as nitric acid, perchloric acid, sulfuric acid, phosphoric acid or carbonic acid, or a lower alkylsulfonic acid such as methanesulfonic acid, trifluoromethanesulfonic acid or ethanesulfonic acid, or an arylsulfonic acid such as benzenesulfonic acid or p-toluenesulfonic acid, or an organic acid such as fumaric acid, succinic acid, citric acid, tartaric acid, oxalic acid, maleic acid, or any other organic acid such as an amino acid, e.g., glutamic acid or aspartic acid may be added to the piperidine derivative. For producing acid-addition salts of the piperidine derivative, for example, an alkali metal salt with sodium or potassium, or an alkaline earth metal salt with calcium or magnesium, or an ammonium salt, or an organic base such as guanidine, triethylamine or dicyclohexylamine may be added to the piperidine derivative.

Esters of the piperidine derivative of formula (I) may also be produced in known methods. On the contrary, the pharmaceutically-acceptable salts or esters of the piperidine derivative of formula (I) may be converted into the corresponding free piperidine derivatives by converting ester according to ordinary methods.

The piperidine derivative of formula (I) or its pharmaceutically-acceptable salt significantly inhibits histamine-H3 receptor-expressing cells from bonding to Nα-methylhistamine (histamine analogue), and therefore effectively acts as a histamine-H3 receptor antagonist or inverse-agonist. In addition, it significantly detracts from the in-vitro action of R-α-methylhistamine (selective agonist).

Not specifically defined, the histamine-H3 receptor antagonist or inverse-agonist of the invention may comprise, as the active ingredient thereof, a piperidine derivative of formula (I) or its pharmaceutically-acceptable salt, and its administration route may be either orally or parenterally. It may be formulated into a preparation suitable for its administration, and may be adminstered. The histamine-H3 receptor antagonist or inverse-agonist is effective, for example, for metabolic system diseases such as obesity, diabetes, hormone secretion disorder, hyperlipemia, gout, fatty liver, circulatory system diseases such as stenocardia, acute/congestive cardiac insufficiency, cardiac infarction, coronary arteriosclerosis, hypertension, nephropathy, electrolyte metabolism disorder, and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

In clinical use of the piperidine derivatives of formula (I) or their pharmaceutically-acceptable salts of the invention, pharmaceutically-acceptable additives may be added thereto to formulate various preparations in accordance with the intended administration route thereof and the preparations may be administered. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the piperidine derivative of formula (I) or its pharmaceutically-acceptable salt of the invention in an amount of from 1.0 to 100% by weight, preferably from 1.0 to 60% by weight of the total medicines.

When the piperidine derivatives of formula (I) or their pharmaceutically-acceptable salts of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions. Not limited to the dose ranges as above, any ordinary physicians, veterinarians and clinicians may readily determine the effective dose necessary for retarding, inhibiting or stopping the development of diseases.

In their use, the piperidine derivatives of formula (I) and their pharmaceutically-acceptable salts of the invention may be combined with one or more other agents effective for treatment of metabolic disorders and/or dietary disorders, circulatory system diseases, and central or peripheral nervous system diseases. The individual ingredients to be combined may be administered at the same time or at different times or successively in order during the treatment period, either as one preparation or as divided different preparations. The ingredients include, for example, co-medicines effective for hypertension, obesity-related hypertension, hypertension-related disorders, cardiomegaly, left ventricle hypertrophy, metabolic disorders, obesity, obesity-related disorders. In other words, the compounds of the invention may be combined with any other co-medicines for so-called combination therapy.

When one or more such co-medicines are combined with a piperidine derivative of formula (I) or its pharmaceutically-acceptable salt of the invention for such combination therapy and when they are administered all at a time, then they may be in the form of a pharmaceutical composition for single administration. On the other hand, when they are administered at the same time or differently or successively, then they may be in different packages. The dose of the co-medicine may depend on the clinical use thereof, and may be suitably determined in accordance with the administration object, the administration route, the diseases and the combination. The form of the co-medicine for administration is not specifically defined, and it may be combined with the piperidine derivative of formula (I) or its pharmaceutically-acceptable salt of the invention when they are administered. The administration with co-medicines mode includes, for example, the following: (1) A compound of the invention is combined with a co-medicine to give a single preparation for single administration; (2) a compound of the invention and a co-medicine are separately formulated into different two preparations, and the two preparations are simultaneously administered in one administration route; (3) a compound of the invention and a co-medicine are separately formulated into different two preparations, and they are administered at different times in one and the same administration route; (4) a compound of the invention and a co-medicine are separately formulated into different two preparations, and they are administered at the same time in two different administration routes; (5) a compound of the invention and a co-medicine are separately formulated into different two preparations, and they are administered at different times in different administration routes (for example, a compound of the invention and a co-medicine are administered in that order, or in an order contrary to this). The blend ratio of the piperidine derivative of formula (I) or its pharmaceutically-acceptable salt of the invention and the co-medicine may be suitably determined depending on the administration object, the administration route, and the disease for the administration.

Therapeutical medicines for diabetes that may be used for such co-medicines include, for example 1) PPAR-γ agonists such as glitazones [e.g., ciglitazone, darglitazone, englitazone, isaglitazone, MCC-555], pioglitazone, rosiglitazone, troglitazone, BRL49653, CLX-0921, 5-BTZD, GW-0207, LG-100641, LY-300512; 2) biguanides such as metformin, buformin, phenformin; 3) protein tyrosine phosphatase 1B inhibitors; 4) sulfonylureas such as acetohexamide, chlorpropamide, diabinese, glibenclamide, glipizide, glyburide, glimepiride, gliclazide, glipentide, gliquidone, glisolamide, trazamide, tolubutamide; 5) meglitinides such as repaglinide, nateglinide; 6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14; 7) α-amylase inhibitors such as tendamistat, trestatin, A13688; 8) insulin secretion promoters such as linogliride, A-4166; 9) fatty acid oxidation inhibitors such as clomoxir, etomoxir, 10) A2 antagonists such as midaglizole, isaglidole, deriglidole, idazoxan, earoxan, fluparoxan; 11) insulin or insulin mimetix such as biota, LP-100, novalapid, insulin determir, insulin lispro, insulin glargine, insulin zinc, Lys-Pro-insulin, GLP-1 (73-7), GLP1 amide (7-36); 12) non-thiazolidinediones such as JT-501, farglitazar, 13) PPARα/γ co-agonists such as CLX-0940, GW-1536, GW-1929, GW-2433, KPR-297, L-796449, L-90, SB219994.

Therapeutical medicines for hyperlipemia that may be used for the above-mentioned co-medicines include, for example, 1) bile acid absorption promoters such as cholesterylamine, colesevelem, colestipol, crosslinked dextran dialkylaminoalkyl derivatives, Colestid®, LoCholest®, Questran®; 2) HMG-CoA reductase inhibitors such as atorvastatin, itavastatin, fluvastatin, lovastatin, pravastatin, rivastatin, rosuvastatin, simvastatin, ZD4522; 3) HMG-CoA synthase inhibitors; 4) cholesterol absorption inhibitors such as snatol ester, β-sitosterol, sterol glucoside, ezetimibe; 5) acyl-coenzyme A cholesterol transacylase inhibitors such as avasimibe, eflucimibe, KY-505, SMP-709; 6) CETP inhibitors such as JTT705, torcetrapib, CP532632, BAY-63-2149, SC-591, SC-795; 7) squalane synthesis inhibitors; 8) antioxidants such as probucol; 9) PPARα agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid®, Lopid®, Tricor®); 10) FXR receptor antagonists such as GW4064, SR-103912; 11) LXR receptor agonists such as GW3965, T9013137, XTCO-179628; 12) lipoprotein synthesis inhibitors such as niacin; 13) renin-angiotensin system inhibitors; 14) microsome triglyceride transportation inhibitors; 15) bile acid reabsorption inhibitors such as BARA1453, SC435, PHA384640, S-435, AZD7706; 16) PPARδ agonists such as GW501516, GW590735; 17) triglyceride synthesis inhibitors; 18) MTTP inhibitors such as LAB687, CP346086; 19) low-density lipoprotein 20) squalane epoxidase inhibitors; 21) platelet agglutination inhibitors; 22) 5-lipoxygenase activation protein inhibitors such as MK-591.

Therapeutical medicines for hypertension that may be used for the above-mentioned co-medicines include, for example, 1) thiazide diuretics such as chlorothialidon, chlorothiazide, dichlorofenamide, hydrofluorothiazide, indapamide, hydrochlorothiazide; loop diuretics such as bumetamide, ethacrynic acid, flosemide, tolusemide; sodium diuretics such as amiloride, triamteren, aldosterone antagonist diuretics such as spironolactone, epilenone; 2), β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tartatolol, tilisolol, timolol; 3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil; 4) angiotensin transferase inhibitors such as benazepril, captopril cilazapril, delapril, enalapril, fosinopril, imidapril, rosinopril, moexipril, quinapril, quinapirat, ramipril, perindopril, periondopril, quanipril, spirapril, tenocapril, transolapril, zofenopril; 5) neutral endopeptidase inhibitors such as omapatrilat, cadoxatril, ecadotril, fosidotril, sampatrilat, AVE7688, ER4030; 6) encloserine antagonists such as tezosentan, A308165, YM62899; 7) vasodilators such as hydraladine, clonidine, minoxidil, nicotinyl alcohol; 8) angiotensin II antagonists such as candesartan, eporsartan, inbesartan, rosartan, pratosartan, tasosartan, telmisartan, balsartan, EXP-3137, FH6828K, RNH6270; 9) α/β adrenaline blockers such as nipradilol, arotinolol, amoslalol; 10) αI blockers such as terazosin, urapidil, purazosin, bunazosine, trimazosin, doxazocin, naphthopidil, indolamin, WHIP164, XEN010; 11) α2 agonists such as lofexidine, tiamenidine, moxonidine, rilmenidine, guanabenz; 12) aldosterone inhibitors.

Anti-obesity medicines that may be used for the above-mentioned co-medicines include, for example, 1) 5HT (serotonin) transporter inhibitors such as paraxetin, fluoxetine, fenfluramine, fluvoxamine, sertraline, imipulamin; 2) norepinephrine transporter inhibitors such as GW320659, decipulamin, talsupramin, nomifensin; 3) cannabinoid-1 receptor 1 (CB-1) antagonists/inverse-agonists such as limonabant (Sanofi Synthelabo), SR-147778 (Sanofi Synthelabo), BAY-65-2520 (Bayer), SLV-318 (Sorbei), as well as compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624, 941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, EP-658546; 4) glerin antagonists such as compounds disclosed in WO01/87355, WO02/08250; 5) histamine (H3) antagonists/inverse-agonists such as thioperamide, 3-(1H-imidazol-4-yl)propyl-N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Phrmazie, 56: 927-32 (2001), benzophenone derivatives Sasse, A. et al., Arch. Pharm. (Weinheim) 334:45-52 (2001)), substituted N-phenylcarbamates (Reidemister, S. et al., Pharmazie, 55: 83-6 (2000)), proxyfen derivatives (Sasse, A. et al., J. Med. Chem., 43: 3335-43 (2000)); 6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A-2001-226269; 7) MCH-2R agonists/antagonists; 8) NPY1 antagonists such as isopropyl 3-chloro-5-(1-(6-[2-(5-ethyl-4-methyl-thiazol-2-yl)ethyl]-4-morpholinyl-4-yl-pyridin-2-ylamino)-ethyl) phenyl]carbamate, BIBP3226, BIB03304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528; 9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120526A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,239,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO0/107409, WO00/185714, WO0/185730, WO00/64880, WO00/68197, WO0/69849, WO01/09120, WO01/14376, WO01/85714, WO01/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312 (2000); 10) reptins such as human recombinant reptin (PEG-OB, Hoffman La Roche), recombinant methionylreptin (Amgen); 11) reptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, 96/23518, WO96/23519, WO96/23520; 12) opioid antagonists such as narmefen (Revex®), 3-methoxynartorexon, naroxon, nartolexon, compounds disclosed in WO00/21509; 13) aurexin antagonists such as SB-334867A, and other compounds disclosed in WO01/96302, WO01/68609, WO02/51232, WO02/51838, WO03/023561; 14) vonbesin receptor subtype-3 agonists; 15) cholecistokinin A (CCK-A) agonists such as AR-R15849, GI-181771, JMV-180, A-71378, A-71623, SR-146131, and other compounds disclosed in U.S. Pat. No. 5,739,106; 16) CNTF (ciliary neurotrophic factors) such as GI-181771 (Glaxo-Smith Kline), SR146131 (Sanofi Synthelabo), butabindide, PD170,292, PD149164 (Pfizer); 17) CNTF derivatives such as axokine (Regeneron), and other compounds disclosed in WO94/09134, WO98/22128, WO99/43813; 18) growth hormone secretion receptor agonists such as NN703, hexarelin, MK-0677, SM-130686, CP424,391, L-692,429, L-163,255, and compounds disclosed in U.S. Pat. No. 6,358,951, US Patent Application Nos. 2002/049196, 2002/022637, WO01/56592, WO02/32888; 19) serotonin receptor-2C agonists such as BVT933, DPCA37215, IK264, PNU22394, WAY161503, R-1065, YN348, and other compounds disclosed in U.S. Pat. No. 3,914,250, WO02/36596, WO02/48124, WO02/10169, WO01/66548, WO02/44152, WO02/51844, WO02/40456, WO02/40457; 20) melanocholtin-3 receptor agonists; 21) melanocholtin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847; 22) monoamine reabsorption inhibitors such as cibtramin (Meridia®/Recuctil®) and its salts, and other derivatives disclosed in U.S. Pat. No. 4,476,680, U.S. Pat. No. 4,806,570, U.S. Pat. No. 5,436,272, US Patent Application No. 2002/0006964, WO01/27068, WO01/62341; 23) serotonin re-uptake inhibitors such as dexfenfluramine, fluoxetine, and other compounds disclosed in U.S. Pat. No. 6,365,633, WO01/27060, WO01/162341; 24) glucagon-like peptide-1 agonists; 25) topiramate (Topimax®); 26) phytopharm compound 57 (e.g., CP644,673); 27) acetyl CoA carboxylase-2 (ACC2) inhibitors; 28) β-adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. No. 5,705,515, U.S. Pat. No. 5,451,677, WO01/74782, WO02/32898; 29) diacylglycerol acyltransferase-1 inhibitors; 30) diacylglycerol acyltransferase-2 inhibitors, 31) fatty acid synthesis inhibitors such as carulenin, C75; 32) phosphodiesterase inhibitors such as theofylline, pentoxifylline, zaprinast, sildenafil, amrinone, milrinone, cilostamide, rolipram, cilomilast; 32) thyroid hormone-β, agonists such as KB-2611 (KaroBioBMS), and other compounds disclosed in WO02/15845, JP-A-2000-256190; 33) phytanic acids such as phytanic acid, 4-[(E)-2-(5,6,7,8-tetrahydro-5,5,8,8-tetramethyl-2-naphthalenyl-1-propenyl]benzoic acid (TTNPB), retinoic acid, and other compounds disclosed in WO99/00123; 34) acylestrogens such as oleoylestrone, and other compounds disclosed in del Mar-Grasa, M. et al., Obesity Research, 9:202-9 (2001); 35) glucocorticoid antagonists; 36) 11-βhydroxysteroid dehydrogenase-1 inhibitors such as BVT3498, BVT2733, and other compounds disclosed in WO01/90091, WO01/90090, WO01/90092; 37) stearoyl-CoA desaturase-1 inhibitors; 38) dipeptidyl peptidase-IV inhibitors such as isoleucine thiazolidine, valine pyrrolidine, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002539, WO03/000180, WO03/000181; 39) lipase inhibitors such as tetrahydroliptatin (Orlistat/Xenical®), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and other compounds disclosed in WO01/7094, U.S. Pat. No. 4,598,089, U.S. Pat. No.

4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438, U.S. Pat. No. 4,242,453; 39) fatty acid transporter inhibitors; 40) dicarboxylate transporter inhibitors; 41) glucose transporter inhibitors; 42) phosphate transporter inhibitors.

Regarding the combination of the piperidine derivative of formula (I) or its pharmaceutically-acceptable salt of the invention with any of the above-mentioned co-medicines, a combination with one or more selected from a group consisting of medicines for diabetes and medicines for hyperlipemia is useful for prevention or remedy of metabolic disorders. In particular, a combination with a medicine for hypertension and a medicine for obesity along with a medicine for diabetes and/or a medicine for hyperlipemia is useful for prevention or remedy of metabolic disorders owing to the synergistic effect thereof.

Not specifically defined, the preventive or the remedy for metabolic disorders of the invention may comprise a piperidine derivative of formula (I) or its pharmaceutically-acceptable salt as the active ingredient thereof.

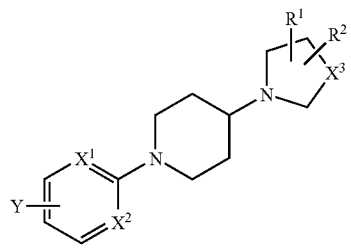
(I)

In formula (I), $X^1$ and $X^2$ independently resent a nitrogen atom or CH; $X^3$ presents $O_s$—$(CH_2)_m$ (in which indicates 0 or 1; m indicates an integer to make (m+s) 0 or 1 to 4); Y represents a group of a general formula (II):

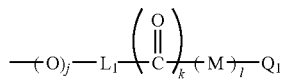
(II)

(in formula (II), j, k and l independently indicate 0 or 1; $L^1$ represents a C1 to C4 alkylene group or a single bond, M represents an oxygen atom or a group of a genera formula (III):

(III)

(in formula (III), $R^0$ represents a hydrogen atom or a C1 to C4 alkyl group); $Q_1$ represents a linear or branched lower alkyl group, an optionally-condensed C3 to C9 cycloalkyl group, a phenyl group, a naphthyl group, or an optionally-condensed 3-membered to 8-membered heterocyclic group (the hetero ring may have from 1 to 3 hetero atoms selected from a group consisting of an oxygen atom, a sulfur atom and a nitrogen atom), which is unsubstituted or has a substituent selected from a group consisting of a cyano group, a hydroxyl group, a lower alkyl group (the lower alkyl group may be further substituted with a hydroxyl group, a halogen atom, an amino group, an aryl group or a heteroaryl group), a cycloalkyl group, a lower alkoxy group (the lower alkoxy group may be further substituted with a halogen atom), a halogen atom, a mono-lower alkylcarbamoyl group, a di-lower alkylcarbamoyl group, a cycloalkyliminocarbamoyl group, a lactam ring, a trifluoromethyl group, a mono-lower alkylamino group, a di-lower alkylamino group and an alkanoyl group)); $R^1$ and $R^2$ independently represent a hydrogen atom, a halogen atom, a linear or branched lower alkyl group, a lower alkoxy group, or an acetyl group substituted with 2 or 3 fluorine atoms; s indicates 0 or 1; m indicates an integer to make (m+s) 0 or 1 to 4.

The preventive or the remedy for metabolic system diseases of the invention is preferably as follows: In formula (I), $R^1$ and $R^2$ are hydrogen atoms, m in $X^3$ indicates an integer of from 1 to 3, s indicates 0. Also preferably, in formula (II), Y is a group of the following general formula (IV):

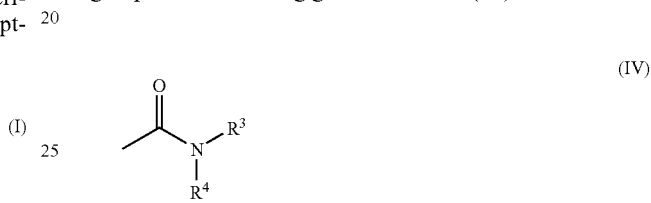
(IV)

Also preferably, in formula (IV), $R^3$ is a hydrogen atom or a lower alkyl group, $R^4$ is a group of the following general formula (V):

(V)

[in formula (V), $R^5$ represents a hydrogen atom, a lower alkyl group, a C3 to C8 cycloalkyl group, an aralkyl group, or a heteroaryl group; n indicates 0 or an integer of from 1 to 4].

Also preferably, in formula (V), $R^3$ is a hydrogen atom, or a lower alkyl group, and $R^4$ is a group of the following general formula (VI):

—$(CH_2)_q$-A (VI)

[in formula (VI), A represents an aryl group, a heteroaryl group, a condensed bicyclic group of a C4 to C7 cycloalkyl group and an aryl group, or a condensed bicyclic group of a C4 to C7 cycloalkyl group and a heteroaryl group; q indicates 0 or an integer of from 1 to 3].

Also preferably, in formula (V), $R^3$ and $R^4$ form a nitrogen-containing heterocyclic group as integrated with the nitrogen atom to which they bond; more preferably, the nitrogen-containing heterocyclic group is a monocyclic group such as a piperidinyl group, a pyrrolidinyl group, an azetidinyl group, a homopiperidinyl group or a heptamethyleneiminyl group, or a bicyclic group of such a monocyclic group and a C4 to C7 cycloalkyl group, a phenyl group or a pyridyl group. Preferably in this case, $X^1$ and $X^2$ are both $CH_2$, or one of them is a nitrogen atom.

Also preferably, the preventive or remedy for metabolic system diseases of the invention is as follows: Y in formula (II) is an aryl group or a 5-membered or 6-membered heteroaryl group, which is unsubstituted or has, in the ring thereof, 1 or 2 substituents selected from a group consisting of a lower alkyl group, a lower alkoxy group, a hydroxyl group and a halogen atom. Preferably in this case, $X^1$ and $X^2$ are both nitrogen atoms.

For the active ingredient of the preventive or remedy for metabolic system diseases of the invention, piperidine derivatives of formula (I) mentioned below are preferred.

N-methyl-N-(1-methylpiperidine-4-yl)-4-[4-(piperidin-1-yl)piperidin-1-yl]benzamide (1),
N-(1-methylpiperidin-4-yl)-4-[4-(piperidin-1-yl)piperidin-1-yl]benzamide (2),
N-methyl-N-(1-cyclobutylpiperidin-4-yl)-4-[4-(piperidin-1-yl)piperidin-1-yl]benzamide (3),
N-methyl-N-(1-cyclopentylpiperidine-4-yl)-4-[4-(piperidin-1-yl)piperidin-1-yl]benzamide (4),
N-methyl-N-(1-cyclohexylpiperidin-4-yl)-4-[4-(piperidin-1-yl)piperidin-1-yl]benzamide (5),
N-methyl-N-(1-cyclohexylmethylpiperidin-4-yl)-4-[4-(piperidin-1-yl)piperidin-1-yl]benzamide (6),
N-methyl-N-[(3R)-1-cyclopentylpyrrolidin-3-yl]-4-[4-(piperidin-1-yl)piperidin-1-yl]benzamide (7),
N-methyl-N-[(3S)-cyclopentylpyrrolidin-3-yl)]-4-[4-(piperidin-1-yl)piperidin-1-yl]benzamide (8),
N-methyl-N-[(3R)-1-benzylpyrrolidin-3-yl)]-4-[4-(piperidin-1-yl)piperidin-1-yl]benzamide (9),
N-methyl-N-[(3R)-1-benzylpyrrolidin-3-yl)]-4-[4-(piperidin-1-yl)piperidin-1-yl]benzamide (10),
N-(pyridin-4-yl)-4-[4-(piperidin-1-yl)piperidin-1-yl]benzamide trifluoroacetate (11),
2-{4-(piperidin-1-yl)piperidin-1-yl]benzoyl-1,2,3,4-tetrahydroisoquinoline (12),
1-{4-(piperidin-1-yl)piperidin-1-yl]benzoyl-1,2,3,4-tetrahydroquinoline (13),
1-{4-(piperidin-1-yl)piperidin-1-yl]benzoyl-4-phenylpiperazine (14),
N-methyl-N-[1-(pyrimidin-2-yl)piperidin-4-yl]-4-[4-(piperidin-1-yl)piperidin-1-yl]benzamide (15),
N-methyl-N-(thiophen-2-yl)methyl-4-[4-(piperidin-1-yl)piperidin-1-yl]benzamide (16),
N-methyl-N-phenethyl-4-[4-(piperidin-1-yl)piperidin-1-yl]benzamide (17),
1-{4-(piperidin-1-yl)piperidin-1-yl]benzoyl-3-3,4-difluorophenyl)pyrrolidine (18),
4-{4-(piperidin-1-yl)piperidin-1-yl]benzylpiperidin-1-yl (19),
N-methyl-N-(1-methylpiperidin-4-yl)-4-[4-(pyrrolidin-1-yl)piperidin-1-yl]benzamide (20),
N-methyl-N-(1-methylpiperidin-4-yl)-4-[4-(azetidin-1-yl)piperidin-1-yl]benzamide (21),
N-methyl-N-(1-methylpiperidin-4-yl)-5-[4-(piperidin-1-yl)piperidin-1-yl]pyridine-2-carboxamide (22),
N-methyl-N-(1-methylpiperidin-4-yl) [4-(4,4-difluoropiperidin-1-yl)piperidin-1-yl]benzamide (23),
2-[(4-piperidin-1-yl)piperidin-1-yl]-5-(4-cyanophenyl)pyrimidine (24),
2-[(4-piperidin-1-yl)piperidin-1-yl]-5-(3-pyridyl)pyrimidine (25),
2-[4-(piperidin-1-yl)piperidin-1-yl]-5-(3-trifluoromethylphenyl)pyrimidine (26),
2-[4-(piperidin-1-yl)piperidin-1-yl]-5-(3,5-dichlorophenyl)pyrimidine (27),
2-[4-(piperidin-1-yl)piperidin-1-yl]-5-(2-naphthyl)pyrimidine (28),
2-[4-(piperidin-1-yl)piperidin-1-yl]-5-[4(pyrrolidin-1-ylcarbonyl)phenyl]pyrimidine (29),
1-[4-(piperidin-1-yl)piperidin-1-yl]-4-(3-pyridyl)benzene (30),
1-piperidin-1-ylmethyl)-4-[4-(piperidin-1-yl)piperidin-1-yl]benzene (31).

Not specifically defined, the preventive or the remedy for circulatory system diseases of the invention may comprise a piperidine derivative of formula (I) or its pharmaceutically-acceptable salt as the active ingredient thereof.

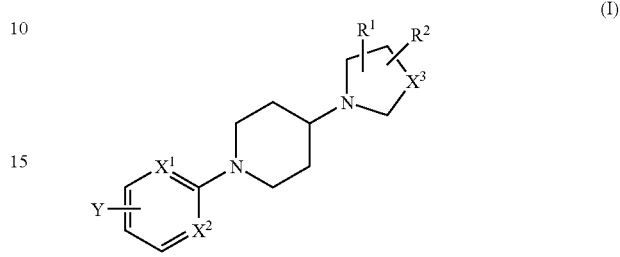

(I)

In formula (I), $X^1$ and $X^2$ independently represent a nitrogen atom or CH; $X^3$ represents $O_s$—$(CH_2)_m$ (in which indicates 0 or 1; m indicates an integer to make (m+s) 0 or 1 to 4); Y represents a group of a general formula (I):

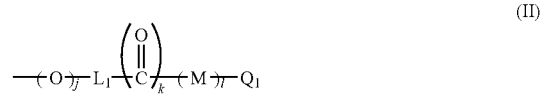

(II)

(in formula (II), j, k and l independently indicate 0 or 1; $L^1$ represents a C1 to C4 alkylene group or a single bond; M represents an oxygen atom or a group of a general formula (III):

(III)

(in formula (III), $R^0$ represents a hydrogen atom or a C1 to C4 alkyl group); $Q_1$ represents a linear or branched lower alkyl group, an optionally-condensed C3 to C9 cycloalkyl group, a phenyl group, a naphthyl group, or an optionally-condensed 3-membered to 8-membered heterocyclic group (the hetero ring may have from 1 to 3 hetero atoms selected from a group consisting of an oxygen atom, a sulfur atom and a nitrogen atom), which is unsubstituted or has a substituent selected from a group consisting of a cyano group, a hydroxyl group, a lower alkyl group (the lower alkyl group may be further substituted with a hydroxyl group, a halogen atom, an amino group, an aryl group or a heteroaryl group), a cycloalkyl group, a lower alkoxy group (the lower alkoxy group may be further substituted with a halogen atom), a halogen atom, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group) (but excepting a case where Y is an alkoxycarbonyl group); $R^1$ and $R^2$ independently represent a hydrogen atom, a halogen atom, a linear or branched lower allyl group, a lower alkoxy group, or an acetyl group substituted with 2 or 3 fluorine atoms; s indicates 0 or 1; m indicates an integer to make (m+s) 0 or 1 to 4.

The preventive or the remedy for circulatory system diseases of the invention is preferably as follows: In formula (I), $R^1$ and $R^2$ are hydrogen atoms, m in $X^3$ indicates an integer of from 1 to 3, s indicates 0. Also preferably, in formula (II), Y is a group of the following general formula (IV):

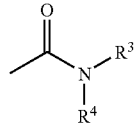

(IV)

Also preferably, in formula (IV), $R^3$ is a hydrogen atom or a lower alkyl group, $R^4$ is a group of the following general formula (V):

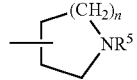

(V)

[in formula (V), $R^5$ represents a hydrogen atom, a lower alkyl group, a C3 to C8 cycloalkyl group, an aralkyl group, or a heteroaryl group; n indicates 0 or an integer of from 1 to 4].

Also preferably, in formula (IV), $R^3$ is a hydrogen atom, or a lower alkyl group, and $R^4$ is a group of the following general formula (VI):

—$(CH_2)_q$-A    (VI)

[in formula (VI), A represents an aryl group, a heteroaryl group, a condensed bicyclic group of a C4 to C7 cycloalkyl group and an aryl group, or a condensed bicyclic group of a C4 to C7 cycloalkyl group and a heteroaryl group; q indicates 0 or an integer of from 1 to 3].

Also preferably, in formula (IV), $R^3$ and $R^4$ form a nitrogen-containing heterocyclic group as integrated with the nitrogen atom to which they bond; more preferably, the nitrogen-containing heterocyclic group is a monocyclic group such as a piperidinyl group, a pyrrolidinyl group, an azetidinyl group, a homopiperidinyl group or a heptamethyleneiminyl group, or a bicyclic group of such a monocyclic group and a C4 to C7 cycloalkyl group, a phenyl group or a pyridyl group. Preferably in this case, $X^1$ and $X^2$ are both $CH_2$, or one of them is a nitrogen atom.

Also preferably, the preventive or remedy for circulatory system diseases of the invention is as follows: Y in formula (II) is an aryl group or a 5-membered or 6-membered heteroaryl group, which is unsubstituted or has, in the ring thereof, 1 or 2 substituents selected from a group consisting of a lower alkyl group, a lower alkoxy group, a hydroxyl group and a halogen atom. Preferably in this case, $X^1$ and $X^2$ are both nitrogen atoms.

For the active ingredient of the preventive or remedy for circulatory system diseases of the invention, piperidine derivatives of formula (I) mentioned below are preferred.

N-methyl-N-(1-methylpiperidin-4-yl)-4-[4-(piperidin-1-yl) piperidin-1-yl]benzamide (1),
N-(1-methylpiperidin-4-yl)-4-[4-(piperidin-1-yl)piperidin-1-yl]benzamide (2),
N-methyl-N-(1-cyclobutylpiperidin-4-yl)-4-[4-(piperidin-1-yl)piperidin-1-yl]benzamide (3),
N-methyl-N-(1-cyclopentylpiperidine-4-yl)-4-[4-(piperidin-1-yl)piperidin-1-yl]benzamide (4),
N-methyl-N-(1-cyclohexylpiperidin-4-yl)-4-[4-(piperidin-1-yl)piperidin-1-yl]benzamide (5),
N-methyl-N-(1-cyclohexylmethylpiperidin-4-yl)-4-[4-(piperidin-1-yl)piperidin-1-yl]benzamide (6),
N-methyl-N-[(3R)-1-cyclopentylpyrrolidin-3-yl]-4-[4-(piperidin-1-yl)piperidin-1-yl]benzamide (7),
N-methyl-N-[(3S)-1-cyclopentylpyrrolidin-3-yl)]-4-[4-(piperidin-1-yl)piperidin-1-yl]benzamide (8),
N-methyl-N-[(3R)-1-benzylpyrrolidin-3-yl)]-4-[4-(piperidin-1-yl)piperidin-1-yl]benzamide (9),
N-methyl-N-[(3R)-1-benzylpyrrolidin-3-yl)]-4-[4-(piperidin-1-yl)piperidin-1-yl]benzamide (10),
N-(pyridin-4-yl)-4-[4-(piperidin-1-yl)piperidin-1-yl]benzamide trifluoroacetate (11),
2-{4-(piperidin-1-yl)piperidin-1-yl]benzoyl-1,2,3,4-tetrahydroisoquinoline (12),
1-{-4-(piperidin-1-yl)piperidin-1-yl]benzoyl-1,2,3,4-tetrahydroquinoline (13),
1-{4-(piperidin-1-yl)piperidin-1-yl]benzoyl-4-phenylpiperazine (14),
N-methyl-N-[1-(pyrimidin-2-yl)piperidin-4-yl]-4-[4-(piperidin-1-yl)piperidin-1-yl]benzamide (15),
N-methyl-N-(thiophen-2-yl)methyl-4-[4(piperidin-1-yl)piperidin-1-yl]benzamide (16),
N-methyl-N-phenethyl-4-[4-(piperidin-1-yl)piperidin-1-yl] benzamide (17),
1-{4(piperidin-1-yl)piperidin-1-yl]benzoyl-3-(3,4-difluorophenyl)pyrrolidine (18),
4-{4-(piperidin-1-yl)piperidin-1-yl]benzylpiperidin-1-yl (19),
N-methyl-N-(1-methylpiperidin-4-yl)-4-[4-pyrrolidin-1-ylpiperidin-1-yl]benzamide (20),
N-methyl-N-(1-methylpiperidin-4-yl)-4-[4-azetidin-1-yl)piperidin-1-yl]benzamide (21),
N-methyl-N-(1-methylpiperidin-4-yl)-5-[4-(piperidin-1-yl) piperidin-1-yl]pyridine-2-carboxamide (22),
N-methyl-N-(1-methylpiperidin-4-yl)-4-[4-(4,4-difluoropiperidin-1-yl)piperidin-1-yl]benzamide (23),
2-[(4-piperidin-1-yl)piperidin-1-yl]-5-(4-cyanophenyl)pyrimidine (24),
2-[(4-piperidin-1-yl)piperidin-1-yl]-5-(3-pyridyl)pyrimidine (25),
2-[4-(piperidin-1-yl)piperidin-1-yl]-5-(3-trifluoromethylphenyl)pyrimidine (26),
2-[4-(piperidin-1-yl)piperidin-1-yl]-5-(3,5-dichlorophenyl) pyrimidine (27),
2-[4-(piperidin-1-yl)piperidin-1-yl]-5-(2-naphthyl)pyrimidine (28),
2-[4-(piperidin-1-yl)piperidin-1-yl]-5-[4-(pyrrolidin-1-ylcarbonyl)phenyl]pyrimidine (29),
1-[4-(piperidin-1-yl)piperidin-1-yl]-4-(3-pyridyl)benzene (30),
1-piperidin-1-ylmethyl)-4-[4-(piperidin-1-yl)piperidin-1-yl] benzene (31).

The preventive or remedy for circulatory system diseases of the invention is effective especially for stenocardia, acute/congestive cardiac insufficiency, cardiac infarction, coronary arteriosclerosis, hypertension, nephropathy, sleep disorder and various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, or electrolyte metabolism disorder.

Not specifically defined, the preventive or remedy for central or peripheral nervous system diseases of the invention may comprise a piperidine derivative of formula (I) or its pharmaceutically-acceptable salt as the active ingredient thereof.

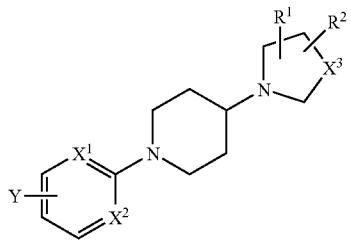

In formula (I), $X^1$ and $X^2$ independently represent a nitrogen atom or CH; $X^3$ represents $O_s$—$(CH_2)_m$ (in which s indicates 0 or 1; m indicates an integer to make (m+s) 0 or 1 to 4); Y represents a group of a general formula (II):

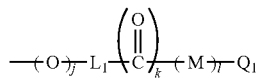

(in formula (II), j, k and l independently indicate 0 or 1; $L^1$ represents a C1 to C4 alkylene group or a single bond; M represents an oxygen atom or a group of a general formula (III):

(in formula (III), $R^0$ represents a hydrogen atom or a C1 to C4 alkyl group); $Q_1$ represents a linear or branched lower alkyl group, an optionally-condensed C3 to C9 cycloalkyl group, a phenyl group, a naphthyl group, or an optionally-condensed 3-membered to 8-membered heterocyclic group (the hetero ring may have from 1 to 3 hetero atoms selected from a group consisting of an oxygen atom, a sulfur atom and a nitrogen atom), which is unsubstituted or has a substituent selected from a group consisting of a cyano group, a hydroxyl group, a lower alkyl group (the lower alkyl group may be further substituted with a hydroxyl group, a halogen atom, an amino group, (an aryl group) or a heteroaryl group), a cycloalkyl group, a halogen atom, a cycloalkyliminocarbamoyl group, a lactam ring and a trifluoromethyl group) (but excepting a case where Y is an alkoxycarbonyl group); $R^1$ and $R^2$ independently represent a hydrogen atom, a halogen atom, a linear or branched lower alkyl group, a lower alkoxy group, or an acetyl group substituted with 2 or 3 fluorine atoms; s indicates 0 or 1; m indicates an integer to make (m+s) 0 or 1 to 4.

Preferably, in formula (I), $R^1$ and $R^2$ are hydrogen atoms, m in $X^3$ indicates an integer of from 1 to 3, s indicates 0. Also preferably, in formula (II), Y is a group of the following general formula (IV):

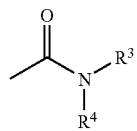

Also preferably, in formula (V), $R^3$ is a hydrogen atom or a lower alkyl group, $R^4$ is a group of the following general formula (V):

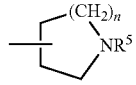

[in formula (V), $R^1$ represents a hydrogen atom, a lower alkyl group, a C3 to C8 cycloalkyl group, an aralkyl group, or a heteroaryl group; n indicates 0 or an integer of from 1 to 4].

Also preferably, in formula (V), $R^3$ is a hydrogen atom, or a lower alkyl group, and $R^4$ is a group of the following general formula (VI):

[in formula (VI), A represents an aryl group, a heteroaryl group, a condensed bicyclic group of a C4 to C7 cycloalkyl group and an aryl group, or a condensed bicyclic group of a C4 to C7 cycloalkyl group and a heteroaryl group; q indicates 0 or an integer of from 1 to 3].

Also preferably, in formula (IV), $R^3$ and $R^4$ form a nitrogen-containing heterocyclic group as integrated with the nitrogen atom to which they bond; more preferably, the nitrogen-containing heterocyclic group is a monocyclic group such as a piperidinyl group, a pyrrolidinyl group, an azetidinyl group, a homopiperidinyl group or a heptamethyleneiminyl group, or a bicyclic group of such a monocyclic group and a C4 to C7 cycloalkyl group, a phenyl group or a pyridyl group. Preferably in this case, $X^1$ and $X^2$ are both $CH_2$, or one of them is a nitrogen atom.

Also preferably, the preventive or remedy for central or peripheral nervous system diseases of the invention is as follows: Y in formula (II) is an aryl group or a 5-membered or 6-membered heteroaryl group, which is unsubstituted or has, in the ring thereof, 1 or 2 substituents selected from a group consisting of a lower alkyl group, a lower alkoxy group, a hydroxyl group and a halogen atom. Preferably in this case, $X^1$ and $X^2$ are both nitrogen atoms.

For the active ingredient of the preventive or remedy for central or peripheral nervous system diseases of the invention, piperidine derivatives of formula (I) mentioned below are preferred.

N-methyl-N-(1-methylpiperidin-4-yl)-4-[4-(piperidin-1-yl)piperidin-1-yl]benzamide (1), N-(1-methylpiperidin-4-yl)-4-[4-(piperidin-1-yl)piperidin-1-yl]benzamide (2), N-methyl-N-(1-cyclobutylpiperidin-4-yl)-4-[4-(piperidin-1-yl)piperidin-1-yl]benzamide (3), N-methyl-N-(1-cyclopentylpiperidine-4-yl)-4-[4-(piperidin-1-yl)piperidin-1-yl]benzamide (4), N-methyl-N-(1-cyclohexylpiperidin-4-yl)-4-[4-(piperidin-1-yl)piperidin-1-yl]benzamide (5), N-methyl-N-(1-cyclohexylmethylpiperidin-4-yl)-4-[4-(piperidin-1-yl)piperidin-1-yl]benzamide (6), N-methyl-N-[(3R)-1-cyclopentylpyrrolidin-3-yl]-4-[4-(piperidin-1-yl)piperidin-1-yl]benzamide (7), N-methyl-N-[(3S)-1-cyclopentylpyrrolidin-3-yl)]-4-[4-(piperidin-1-yl)piperidin-1-yl]benzamide (8), N-methyl-N-[(3R)-1-benzylpyrrolidin-3-yl)]-4-[4-(piperidin-1-yl)piperidin-1-yl]benzamide (9), N-methyl-N-[(3R)-1-benzylpyrrolidin-3-yl)]-4-[4-(piperidin-1-yl)piperidin-1-yl]benzamide (10), N-(pyridin-4-yl)-4-[4-(piperidin-1-yl)piperidin-1-yl]benzamide trifluoroacetate (11), 2-{4-(piperidin-1-yl)piperidin-1-yl]benzoyl-1,2,3,4-tetrahydroisoquinoline (12),
1-{-4-(piperidin-1-yl)piperidin-1-yl]benzoyl-1,2,3,4-tetrahydroquinoline (13),
1-{4-(piperidin-1-yl)piperidin-1-yl]benzoyl-4-phenylpiperazine (14),
N-methyl-N-[1-(pyrimidin-2-yl)piperidin-4-yl]-4-[4-(piperidin-1-yl)piperidin-1-yl]benzamide (15),
N-methyl-N-(thiophen-2-yl)methyl-4-[4(piperidin-1-yl)piperidin-1-yl]benzamide (16),
N-methyl-N-phenethyl-4-[4-(piperidin-1-yl)piperidin-1-yl]benzamide (17),
1-{4(piperidin-1-yl)piperidin-1-yl]benzoyl-3-(3,4-difluorophenyl)pyrrolidine (18),
4-{4-(piperidin-1-yl)piperidin-1-yl]benzylpiperidin-1-yl (19),
N-methyl-N-(1-methylpiperidin-4-yl)-4-[4-pyrrolidin-1-ylpiperidin-1-yl]benzamide (20),
N-methyl-N-(1-methylpiperidin-4-yl)-4-[4-azetidin-1-yl)piperidin-1-yl]benzamide (21),
N-methyl-N-(1-methylpiperidin-4-yl)-5-[4-(piperidin-1-yl)piperidin-1-yl]pyridine-2-carboxamide (22),
N-methyl-N-(1-methylpiperidin-4-yl)-4-[4-(4,4-difluoropiperidin-1-yl)piperidin-1-yl]benzamide (23),
2-[(4-piperidin-1-yl)piperidin-1-yl]-5-(4-cyanophenyl)pyrimidine (24),
2-[(4-piperidin-1-yl)piperidin-1-yl]-5-(3-pyridyl)pyrimidine (25),
2-[4-(piperidin-1-yl)piperidin-1-yl]-5-(3-trifluoromethylphenyl)pyrimidine (26),
2-[4-(piperidin-1-yl)piperidin-1-yl]-5-(3,5-dichlorophenyl)pyrimidine (27),
2-[4-(piperidin-1-yl)piperidin-1-yl]-5-(2-naphthyl)pyrimidine (28),
2-[4-(piperidin-1-yl)piperidin-1-yl]-5-[4-(pyrrolidin-1-ylcarbonyl)phenyl]pyrimidine (29),
1-[4-(piperidin-1-yl)piperidin-1-yl]-4-(3-pyridyl)benzene (30),
1-(piperidin-1-ylmethyl)-4-[4-(piperidin-1-yl)piperidin-1-yl]benzene (31).

The preventive or remedy for central and peripheral nervous system diseases of the invention is effective especially for bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, recognition disorder, motion disorder, paresthesia, dysosmia, epilepsy, morphine resistance, narcotic dependency, alcoholic dependency.

The invention is described more concretely with reference to the following Formulation Examples and Production Examples, which, however, do not restrict the invention.

For thin-layer chromatography of compounds, used was a plate of Silicagel $60F_{245}$ (Merck); and for detection, used was a UV detector. Wakogel® C-300 (Wako Pure Chemicals) was used for the column silica gel; and LC-SORB® SP-B-ODS (Chemco) or YMCGEL® ODS-AQ 120-S50 (Yamamura Chemical Laboratories) was for the reversed-phase column silica gel.

Mass spectrum was determined according to an electrospray ionization (ES process, using QuattroII (Micromass).

Example 1

Production of Piperidine Derivatives

Compound 1

N-methyl-N-(1-methylpiperidinyl)-4-[4-(piperidin-1-yl)piperidin-1-yl]benzamide

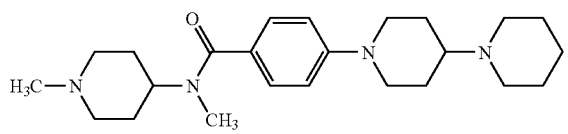

(1)

At room temperature, 1-methyl(4-methylamino)piperidine (0.056 ml, 0.38 mmols), O-(7-azabenzotriazol-1-yl-N,N,N',N'-tetramethyluronium hexafluorophosphate (121 mg, 0.32 mmols) and diisopropylethylamine (0.17 ml, 0.96 mmols) were added to a dimethylformamide solution (1.0 ml) of 4-[(4-piperidin-1-yl)piperidin-1-yl]benzoic acid hydrochloride (103 mg, 0.32 mmols) obtained in Reference Example 1, and s in a nitrogen atmosphere at room temperature for 14 hours. The reaction solution was extracted with ethyl acetate, the organic layer was washed with water, saturated sodium bicarbonate solution and saturated saline solution in the order, dried with anhydrous magnesium sulfate, and then concentrated. The residue was purified through preparative thin-layer chromatography (chloroform/methanol/aqueous ammonia=10/1/0.1) to obtain the entitled compound (56 mg, 44%).

$^1$H NMR (400 MHz, CDCl$_3$, δ ppm): 1.43-2.07 (18H, m), 2.24-2.31 (3H, m), 2.50-2.70 (4H, m), 2.72-2.82 (2H, m), 2.86-2.96 (5H, m), 3.79-3.87 (2H, m), 6.87 (2H, d, J=8.8 Hz), 7.28 (2H, d, J=8.8 Hz);

Mass spectrum (ESI): 399 (M+H)

The following compounds 2 to 23 were produced in the same production method as that for the compound 1, or according to the method, or in combination of the method with an ordinary method.

Compound 2

N-(1-methylpiperidin-4-yl)-4-[4-(piperidin-1-yl)piperidin-1-yl]benzamide

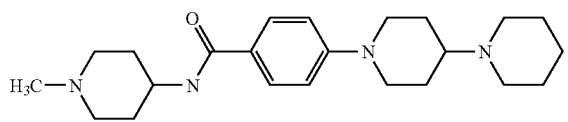

(2)

The compound was produced according to the same production method as that for the compound 1, for which, however, 1-methyl-4-aminopiperidine was used in place of 1-methyl(4-methylamino)piperidine.

$^1$H NMR (400 MHz, CDCl$_3$, δ ppm): 1.41-1.78 (10H, m), 1.88-1.96 (2H, m), 1.99-2.06 (2H, m), 2.11-2.20 (2H, m), 2.29 (3H, s), 2.41-2.58 (5H, m), 2.74-2.85 (4H, m), 3.83-3.90

(2H, m), 3.92-4.02 (1H, m), 5.80 (1H, brd, J=7.6 Hz), 6.86 (2H, d, J=8.8 Hz), 7.62 (2H, d, J=8.8 Hz);
Mass spectrum (ES): 385 (M+H)

Compound 3

N-methyl-N-(1-cyclobutylpiperidin-4-yl)-4-[4-(piperidin-1-yl)piperidin-1-yl]benzamide

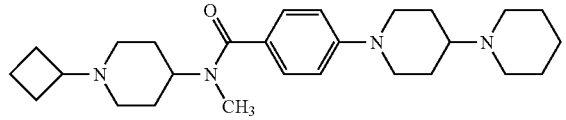

(3)

The compound was produced according to the same production method as that for the compound 1, for which, however, 1-cyclobutyl(4-methylamino)piperidine was used in place of 1-methyl(4-methylamino)piperidine.
$^1$H NMR (400 MHz, CDCl$_3$, δ ppm): 1.41-2.07 (2H, m), 2.40-2.59 (6H, m), 2.62-2.80 (4H, m), 2.83-2.90 (2H, m), 2.90 (3H, s), 3.79-3.86 (2H, m), 6.87 (2H, d, J=8.8 Hz), 7.27 (2H, d, J=8.8 Hz);
Mass spectrum (ESI): 439 (M+H)

Compound 4

N-methyl-N-(1-cyclopentylpiperidine-4-yl)-4-[4-(piperidin-1-yl)piperidin-1-yl]benzamide

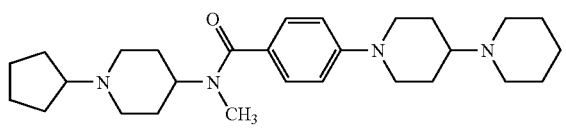

(4)

The compound was produced according to the same production method as that for the compound 1, for which, however, 1-cyclopentyl(4-methylamino)piperidine was used in place of 1-methyl(4-methylamino)piperidine.
$^1$H NMR (400 MHz, CDCl$_3$, δ ppm): 1.33-2.10 (25H, m), 2.40-2.58 (6H, m), 2.72-2.80 (2H, m), 2.90 (3H, s), 3.04-3.14 (2H, m), 3.79-3.86 (2H, m), 6.87 (2H, d, J=8.8 Hz), 7.28 (2H, d, J=8.8 Hz);
Mass spectrum (ESI): 453 (M+H)

Compound 5

N-methyl-N-(1-cyclohexylpiperidin-4-yl)-4-[4-(piperidin-1-yl)piperidin-1-yl]benzamide

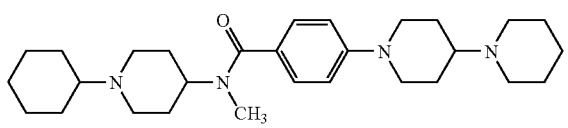

(5)

The compound was produced according to the same production method as that for the compound 1, for which, however, 1-cyclohexyl(4-methylamino)piperidine was used in place of 1-methyl(4-methylamino)piperidine.
$^1$H NMR (400 MHz, CDCl$_3$, δ ppm): 1.00-1.30 (6H, m), 1.40-1.49 (2H, m), 1.56-1.1.95 (19H, m), 2.24-2.35 (1H, m), 2.38-247 (1H, m), 2.49-2.57 (4H, m), 2.71-2.80 (2H, m), 2.86-3.00 (2H, m), 2.90 (3H, s), 3.79-3.86 (2H, m), 6.87 (2H, d, J=8.8 Hz), 7.28 (2H, d, J=8.8 Hz);
Mass spectrum (ESI): 467 (M+H)

Compound 6

N-methyl-N-(1-cyclohexylmethylpiperidin-4-yl)-4-[4-(piperidin-1-ylpiperidin-1-yl]benzamide

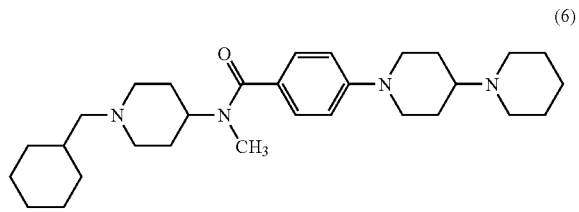

(6)

The compound was produced according to the same production method as that for the compound 1, for which, however, 1-cyclohexylmethyl(4-methylamino)piperidine was used in place of 1-methyl(4-methylamino)piperidine.
$^1$H NMR (400 MHz, CDCl$_3$, δ ppm): 0.78-0.91 (2H, m), 1.05-1.28 (4H, m), 1.33-1.49 (4H, m), 1.52-1.95 (20H, m), 2.02-2.12 (2H, m), 2.38-2.60 (4H, m), 2.68-2.80 (2H, m), 2.82-2.97 (1H, m), 2.90 (3H, s), 3.77-3.86 (2H, m), 6.87 (2H, d, J=8.8 Hz), 7.28 (2H, d, J=8.8 Hz);
Mass spectrum (ESI): 481 (M+H)

Compound 7

N-methyl-N-[(3R)-1-cyclopentylpyrrolidin-3-yl)]-4-[4-(piperidin-1-yl)piperidin-1-yl]benzamide

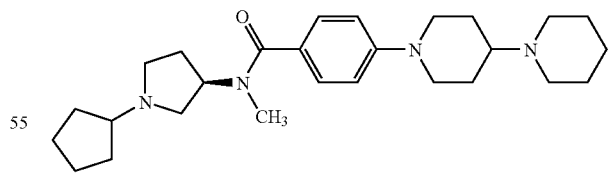

(7)

The compound was produced according to the same production method as that for the compound 1, for which, however, 1-cyclopentyl((3R)-methylamino)pyrrolidine was used in place of 1-methyl(4-methylamino)piperidine.
$^1$H NMR (400 MHz, CDCl$_3$, δ ppm): 1.33-2.13 (20H, m), 2.32-2.78 (12H, m), 3.01 (3H, s), 3.77-3.84 (2H, m), 4.50-4.80 (1H, m), 6.86 (2H, d, J=8.4 Hz), 7.27 (2H, d, J=8.4 Hz);
Mass spectrum (ESI): 439 (M+H)

Compound 8

N-methyl-N-[(3S)-1-cyclopentylpyrrolidin-3-yl)]-4-[4-(piperidin-1-yl)piperidin-1-yl]benzamide

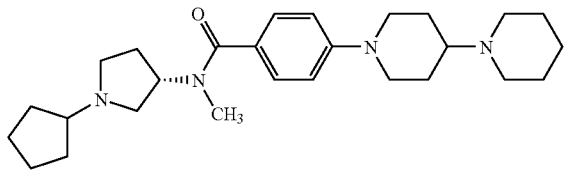

(8)

The compound was produced according to the same production method as that for the compound 1, for which, however, 1-cyclopentyl((3S)-methylamino)pyrrolidine was used in place of 1-methyl(4-methylamino)piperidine.

$^1$H NMR (400 MHz, CDCl$_3$, δ ppm): 1.33-2.13 (20H, m), 2.32-2.78 (12H, m), 3.01 (3H, s), 3.77-3.84 (2H, m), 4.50-4.80 (1H, m), 6.86 (2H, d, J=8.4 Hz), 727 (2H, d, J=8.4 Hz);

Mass spectrum (ESI): 439 (M+H)

Compound 9

N-methyl-N-[(3R)-1-benzylpyrrolidin-3-yl]-4-[4-(piperidin-1-yl)piperidin-1-yl]benzamide

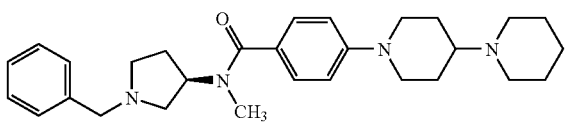

(9)

The compound was produced according to the same production method as that for the compound 1, for which, however, 1-benzyl((3R)methylamino)pyrrolidine was used in place of 1-methyl(4-methylamino)piperidine.

$^1$H NMR (400 MHz, CDCl$_3$, δ ppm): 1.41-1.48 (2H, m), 1.55-1.74 (8H, m), 1.86-1.95 (3H, m), 2.24-2.31 (1H, m), 2.38-2.58 (6H, m), 2.69-2.79 (3H, m), 2.81-2.88 (1H, m), 3.03 (3H, s), 3.45-3.50 (1H, m), 3.62-3.68 (1H, m), 3.78-3.85 (2H, m), 6.85 (2H, d, J=8.0 Hz), 7.20-7.30 (5H, m), 7.28 (2H, d, J=8.0 Hz);

Mass spectrum (ESI): 461 (M+H)

Compound 10

N-methyl-N-[(3R)-1-benzylpyrrolidin-3-yl)]-4-[4 (piperidin-1-yl)piperidin-1-yl]benzamide

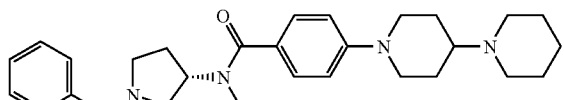

(10)

The compound was produced according to the same production method as that for the compound 1, for which, however, 1-benzyl((3S)-methylamino)pyrrolidine was used in place of 1-methyl(4-methylamino)piperidine.

$^1$H NMR (400 MHz, CDCl$_3$, δ ppm): 1.41-1.48 (2H, m), 1.55-1.74 (8H, m), 1.86-1.95 (3H, m), 2.24-2.31 (1H, m), 2.38-2.58 (6H, m), 2.69-2.79 (3H, m), 2.81-2.88 (1H, m), 3.03 (3H, s), 3.45-3.50 (1H, m), 3.62-3.68 (1H, m), 3.78-3.85 (2H, m), 6.85 (2H, d, J=8.0 Hz), 7.20-7.30 (5H, m), 7.28 (2H, d, J=8.0 Hz);

Mass spectrum (ESI): 461 (M+H)

Compound 11

N-(pyridin-4-yl)-4-[4-(piperidin-1-yl)piperidin-1-yl]benzamide trifluoroacetate

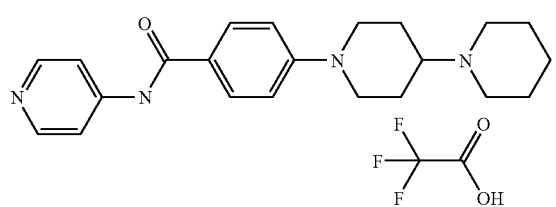

(11)

The compound was produced according to the same production method as that for the compound 1, for which, however, 4-aminopyridine was used in place of 1-methyl(4-methylamino)piperidine.

$^1$H NMR (400 MHz, CD$_3$OD, δ ppm): 1.47-1.60 (1H, m), 1.70-1.90 (5H, m), 1.95-2.05 (2H, m), 2.16-2.25 (2H, m), 2.90-3.08 (4H, m), 3.32-3.48 (1H, m), 3.50-3.59 (2H, m), 4.13-4.21 (2H, m), 7.08 (2H, d, J=8.8 Hz), 7.94 (2H, d, J=8.8 Hz), 8.29 (2H, d, J=8.4 Hz), 8.57 (2H, d, J=8.4 Hz);

Mass spectrum (ESI): 365 (M+H)

Compound 12

2-{4-(piperidin-1-yl)piperidin-1-yl]benzoyl-1,2,3,4-tetrahydroisoquinoline

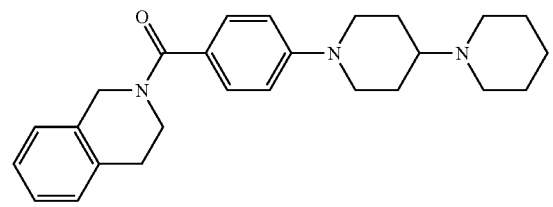

(12)

The compound was produced according to the same production method as that for the compound 1, for which, however, 1,2,3,4-tetrahydroisoquinoline was used in place of 1-methyl(4-methylamino)piperidine.

$^1$H NMR (400 MHz, CDCl$_3$, δ ppm): 1.41-1.51 (2H, m), 1.57-1.73 (6H, m), 1.88-1.97 (2H, m), 2.41-2.61 (5H, m), 2.73-2.83 (2H, m), 2.88-2.97 (2H, m), 3.72-3.92 (4H, m), 4.70-4.83 (2H, m), 6.89 (2H, d, J=8.8 Hz), 7.01-7.21 (4H, m), 7.37 (2H, d, J=8.8 Hz);

Mass spectrum (ES): 404 (M+1)

Compound 13

1-{4-(piperidin-1-yl)piperidin-1-yl]benzoyl-1,2,3,4-tetrahydroquinoline

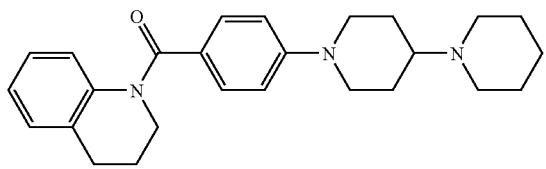

(13)

The compound was produced according to the same production method as that for the compound 1, for which, however, 1,2,3,4-tetrahydroquinoline was used in place of 1-methyl(4-methylamino)piperidine.

$^1$H NMR (400 MHz, CDCl$_3$, δ ppm): 1.28-4.42 (25H, m), 6.68-7.77 (8H, m);

Mass spectrum (ESI): 404 (M+H)

Compound 14

1-{4-(piperidin-1-yl)piperidin-1-yl]benzoyl-4-phenylpiperazine

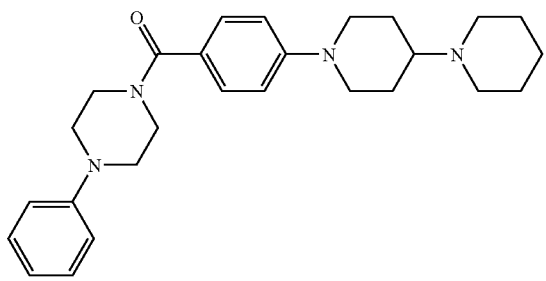

(14)

The compound was produced according to the same production method as that for the compound 1, for which, however, 4-phenylpiperazine was used in place of 1-methyl(4-methylamino)piperidine.

$^1$H NMR (400 MHz, CDCl$_3$, δ ppm): 1.40-1.50 (2H, m), 1.55-1.72 (6H, m), 1.88-1.98 (2H, m), 2.40-2.60 (5H, m), 2.72-2.82 (2H, m), 3.10-3.23 (4H, m), 3.70-3.88 (6H, m), 6.81-6.98 (5H, m), 7.21-7.30 (2H, m), 7.35 (2H, d, J=8.8 Hz);

Mass spectrum (ESI): 433 (M+H)

Compound 15

N-methyl-N-[1-(pyrimidin-2-yl)piperidin-4-yl]-[4-(piperidin-1-yl)piperidin-1-yl]benzamide

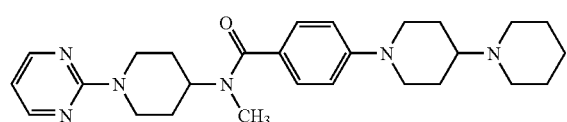

(15)

The compound was produced according to the same production method as that for the compound 1, for which, however, 1 (pyrimidin-2-yl)-4-methylaminopiperidine was used in place of 1-methyl(4-methylamino)piperidine.

$^1$H NMR (400 MHz, CDCl$_3$, δ ppm): 1.40-1.50 (2H, m), 1.55-1.88 (11H, m), 1.90-2.01 (2H, m), 2.41-2.63 (5H, m), 2.71-2.99 (4H, m), 2.87 (3H, s), 3.80-3.90 (2H, m), 4.82-4.92 (2H, m), 6.46 (1H, t, J=4.8 Hz), 6.88 (2H, d, J=8.8 Hz), 7.31 (2H, d, J=8.8 Hz), 8.28 (2H, d, J=4.8 Hz);

Mass spectrum (ESI): 463 (M+H)

Compound 16

N-methyl-N-(thiophen-2-yl)methyl-4-[4-(piperidin-1-yl)piperidin-1-yl]benzamide

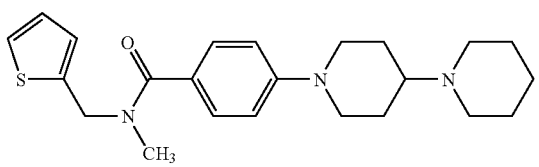

(16)

The compound was produced according to the same production method as that for the compound 1, for which, however, 2-methylaminomethylthiophene was used in place of 1-methyl(4-methylamino)piperidine.

$^1$H NMR (400 MHz, CDCl$_3$, δ ppm): 1.40-1.50 (2H, m), 1.57-1.72 (6H, m), 1.88-1.97 (2H, m), 2.41-2.60 (5H, m), 2.70-2.80 (2H, m), 3.00 (3H, s), 3.80-3.88 (2H, m), 4.70-4.81 (2H, m), 6.86 (2H, d, J=8.8 Hz), 6.92-7.00 (2H, m), 7.21-7.28 (1H, m), 7.39 (2H, d, J=8.8 Hz);

Mass spectrum (ESI): 398 (M+H)

Compound 17

N-methyl-N-phenethyl-4-[4-(piperidin-1-yl)piperidin-1-yl]benzamide

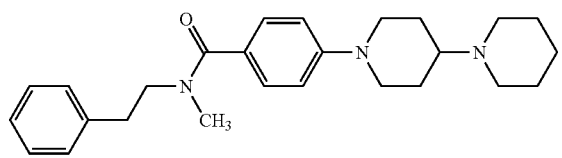

(17)

The compound was produced according to the same production method as that for the compound 1, for which, however, methylphenethylamine was used in place of 1-methyl (4-methylamino)piperidine.

$^1$H NMR (400 MHz, CDCl$_3$, δ ppm): 1.37-1.50 (2H, m), 1.52-2.72 (6H, m), 1.79-1.99 (2H, m), 2.01-2.62 (6H, m), 2.66-2.80 (2H, m), 2.82-3.12 (4H, m), 3.43-3.72 (2H, m), 3.77-3.90 (2H, m), 6.80-6.92 (2H, m), 6.96-7.40 (7H, m);

Mass spectrum (ESI): 406 (M+H)

Compound 18

1-{4-(piperidin-1-yl)piperidin-1-yl]benzoyl-3-(3,4-difluorophenyl)pyrrolidine

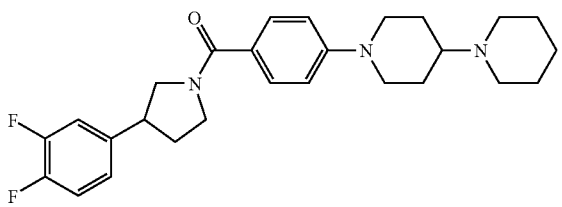

(18)

The compound was produced according to the same production method as that for the compound 1, for which, however, 3-(3,4-difluorophenyl)pyrrolidine was used in place of 1-methyl(4-methylamino)piperidine.

$^1$H NMR (400 MHz, CDCl$_3$, δ ppm): 1.40-1.50 (2H, m), 1.55-1.78 (6H, m), 1.85-2.12 (4H, m), 2.20-2.68 (6H, m), 2.70-2.88 (2H, m), 3.22-4.15 (6H, m), 6.82-7.20 (5H, m), 7.43-7.59 (2H, m);

Mass spectrum (ESI): 454 (M+H)

Compound 19

4-{-4-(piperidin-1-yl)piperidin-1-yl]benzylpiperidin-1-yl

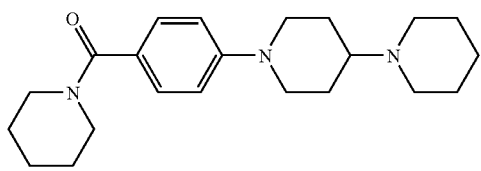

(19)

The compound was produced according to the same production method as that for the compound 1, for which, however, piperidine was used in place of 1-methyl(4-methylaminopiperidine.

$^1$H NMR (400 MHz, CDCl$_3$, δ ppm): 1.16-2.10 (16H, m), 2.34-2.64 (5H, m), 3.22-3.90 (4H, m), 6.87 (2H, d, J=7.2 Hz), 7.28 (2H, d, J=72 Hz);

Mass spectrum (ES: 356 (M+H)

Compound 20

N-methyl-N-(1-methylpiperidin-4-yl)-4-[4-(pyrrolidin-1-yl)piperidin-1-yl]benzamide

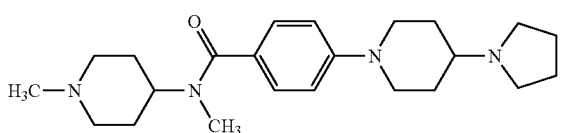

(20)

Using 4-{4-pyrrolidin-1-yl)piperidin-1-yl}benzoic acid hydrochloride that had been produced in the same production method as that for 4-{4-(piperidin-1-yl)piperidin-1-yl}benzoic acid hydrochloride produced in Reference Example, or according to the method, or in combination of the method with an ordinary method, the entitled compound was produced according to the same production method as that for the compound 1.

$^1$H NMR (400 MHz, CDCl$_3$, δ ppm): 1.62-1.72 (4H, m), 1.79-2.04 (12H, m), 2.16-2.24 (1H, m), 226 (3H, s), 2.59-2.66 (4H, m), 2.77-2.92 (3H, m), 2.90 (3H, s), 3.72-3.79 (2H, m), 6.87 (2H, d, J=8.8 Hz), 7.28 (2H, d, J=8.8 Hz);

Mass spectrum (ESI): 385 (M+H)

Compound 21

N-methyl-N-(1-methylpiperidin-4-yl)-4-[4-(azetidin-1-yl)piperidin-1-yl]benzamide

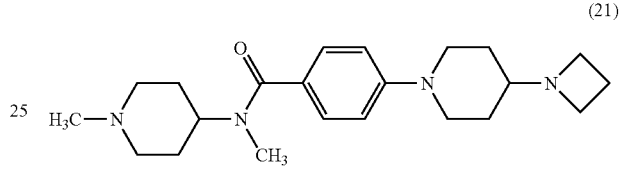

(21)

Using 4-{4-(azetidin-1-yl)piperidin-1-yl}benzoic acid hydrochloride that had been produced in the same production method as that for 4-{4-(piperidin-1-yl)piperidin-1-yl}benzoic acid hydrochloride produced in Reference Example, or according to the method, or in combination of the method with an ordinary method, the entitled compound was produced according to the same production method as that for the compound 1.

$^1$H NMR (400 MHz, CDCl$_3$, δ ppm): 1.40-1.53 (2H, m), 1.57-2.35 (14H, m), 2.29 (3H, s), 2.77-3.00 (3H, m), 2.90 (3H, s), 3.24-3.37 (3H, m), 3.66-3.75 (2H, m), 6.60 (2H, d, J=8.8 Hz), 7.29 (2H, d, J=8.8 Hz);

Mass spectrum (ESI): 371 (M+H)

Compound 22

N-methyl-N-(1-methylpiperidin-4-yl)-5-[4-(piperidin-1-yl)piperidin-1-yl]pyridine-2-carboxamide

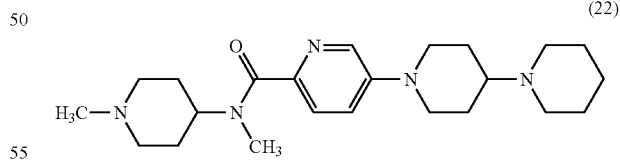

(22)

The entitled compound was produced by reacting 1-methyl(4-methylamino)piperidine and 5-{(4-piperidin-1-yl)piperidin-1-yl}pyridine-2-carboxylic acid. 5-{4-(Piperidin-1-yl)piperidin-1-yl}pyridine-2-carboxylic acid was produced in the same production method as that for 4-[4-(piperidin-1-yl)piperidin-1-yl}benzoic acid hydrochloride produced in Reference Example 1, or according to the method, or in combination of the method with an ordinary method.

$^1$H NMR (400 MHz, CDCl$_3$, δ ppm): 1.41-1.52 (2H, m), 1.57-1.73 (6H, m), 1.75-2.02 (7H, m), 2.10-2.36 (4H, m), 2.42-2.53 (2H, m), 2.54 (3H, s), 2.77-3.02 (3H, m), 2.98

(3H, s), 3.79-3.97 (3H, m), 4.46-4.58 (1H, m), 7.18 (1H, dd, J=2.8, 8.8 Hz), 7.52 (1H, d, J=8.8 Hz), 8.19 (1H, d, J=2.8 Hz);

Mass spectrum (ESI): 400 (M+H)

Compound 23

N-methyl-N-(1-methylpiperidin-4-yl)-4-[4-(4,4-difluoropiperidin-1-yl)piperidin-1-yl]benzamide

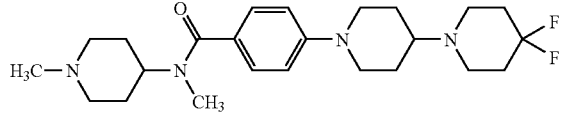

(23)

The entitled compound was produced by reacting 1-methyl (4-methylamino)piperidine and 4-{(4,4-difluoropiperidin-1-yl)piperidin-1-yl}benzoic acid hydrochloride. 4-{(4,4-Difluoropiperidin-1-yl)piperidin-1-yl}benzoic acid hydrochloride was produced in the same production method as that for 4-[(4-piperidin-1-yl)piperidin-1-yl}benzoic acid hydrochloride produced in Reference Example 1, or according to the method, or in combination of the method with an ordinary method.

$^1$H NMR (400 MHz, CDCl$_3$, δ ppm): 1.56-1.76 (6H, m), 1.84-2.06 (9H, m), 2.27 (3H, brs), 2.48-2.58 (1H, m), 2.64-2.70 (4H, m), 2.73-2.82 (2H, m), 2.84-2.97 (2H, m), 2.90 (3H, s), 3.78-2.86 (2H, m), 6.87 (2H, d, J=8.4 Hz), 7.28 (2H, d, J=8.4 Hz);

Mass spectrum (ESI): 435 (M+H)

Compound 24

2-[4-(piperidin-1-yl)piperidin-1-yl]-5-(4-cyanophenyl)pyrimidine

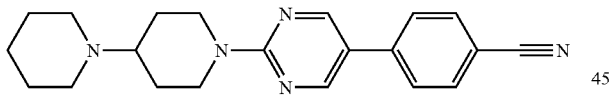

(24)

1) Production of 2-[4-(piperidin-1-yl)piperidin-1-yl]-5-bromopyrimidine 4-(Piperidin-1-yl)piperidine (342 mg, 2.03 mmols) and cesium carbonate (764 mg, 2.34 mmols) were added to DMF solution (10 ml) of 2-chloro-5-bromopyrimidine (300 mg, 1.56 mmols), and stirred at room temperature for 16 hours. Water was added to the reaction mixture, which was then extracted with ethyl acetate. The organic layer was washed with saturated saline solution, dried with anhydrous sodium sulfate, and then concentrated under reduced pressure. The residue was purified through silica gel column chromatography (C-300, chloroform/methanol=100/3) to obtain the entitled compound (349 mg, 69%).

2) 1,2-Dimethoxyethane (2.0 ml) and aqueous 2 N sodium carbonate solution (0.7 ml) were added to 5-bromo-2-[4-(piperidin-1-yl)piperidin-1-yl]pyrimidine (169 mg, 0.52 mmols), and then 4-cyanoboronic acid (95 mg, 0.65 mmols) and tetrakis(triphenylphosphine)palladium(0) (15 mg, 0.013 mmols) were added thereto and stirred in a nitrogen atmosphere at 90° C. for 4 hours. The reaction mixture was cooled to room temperature, and then extracted with ethyl acetate. The organic layer was washed with saturated saline solution, then dried with anhydrous sodium sulfate, and concentrated under reduced pressure. The residue was purified through silica gel column chromatography (C-300, chloroform/methanol=100/3) to obtain the entitled compound (113 mg, 62%).

$^1$H NMR (300 M CDCl$_3$, δ ppm): 1.38-1.66 (8H, m), 1.87-1.98 (2H, m), 2.47-2.62 (5H, m), 2.86-2.97 (2H, m), 4.8-4.94 (2H, m), 7.57 (2H, d, J=8.3 Hz), 7.71 (1H, d, J=8.3 Hz), 8.51 (2H, s);

Mass spectrum (ESI): 348 (M+H)

The following compounds 25 to 30 were produced in the same production method as that for the compound 24, or according to the method, or in combination of the method with an ordinary method.

Compound 25

2-[(4-piperidin-1-yl)piperidin-1-yl]-5-(3-pyridyl)pyrimidine

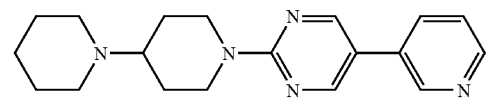

(25)

The entitled compound was obtained by reacting 5-bromo-2-{4-(piperidin-1-yl)piperidin-1-yl}pyrimidine that has been obtained in the production process for the compound 24, with pyridine-3-boric acid.

$^1$H NMR (400 MHz, CDCl$_3$, δ ppm): 1.41-1.77 (9H, m), 1.91-2.00 (2H, m), 2.51-2.65 (4H, m), 2.86-2.95 (2H, m), 4.84-4.91 (2H, m), 7.34 (1H, dd, J=4.8, 8.8 Hz), 7.74 (1H, d, J=8.0 Hz), 8.51 (2H, s), 8.55 (1H, d, J=4.8 Hz), 8.73 (1H, s);

Mass spectrum (ESI): 324 (M+H)

Compound 26

2-[4-(piperidin-1-yl)piperidin-1-yl]-5-(3-trifluoromethylphenyl)pyrimidine

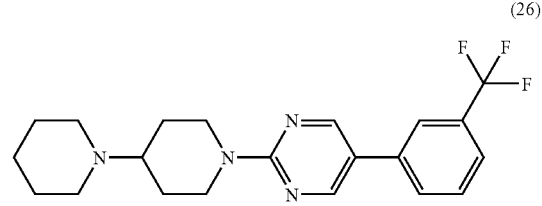

(26)

The entitled compound was obtained by reacting 5-bromo-2-{4-(piperidin-1-yl)piperidin-1-yl}pyrimidine that has been obtained in the production process for the compound 24, with 3-trifluoromethyl-phenylboric acid.

$^1$H NMR (300 MHz, CDCl$_3$, δ ppm): 1.38-1.74 (9H, m), 1.89-2.00 (2H, m), 2.49-2.64 (4H, m), 2.83-2.96 (2H, m), 4.82-4.93 (2H, m), 7.51-7.67 (3H, m), 7.70 (1H, s), 8.54 (2H, s);

Mass spectrum (ESI): 391 (M+H)

Compound 27

2-[4-(piperidin-1-yl)piperidin-1-yl]-5-(3,5-chlorophenyl)pyrimidine

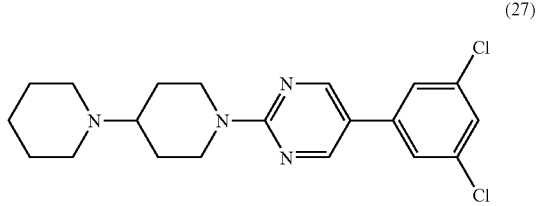

(27)

The entitled compound was obtained by reacting 5-bromo-2-{4-(piperidin-1-yl)piperidin-1-yl}pyrimidine that has been obtained in the production process for the compound 24, with 3,5-dichlorophenylboric acid.

$^1$H NMR (300 MHz, CDCl$_3$, δ ppm): 1.38-1.86 (8H, m), 1.87-2.00 (2H, m), 2.48-2.64 (5H, m), 2.83-2.97 (2H, m), 4.83-4.94 (2H, m), 7.30 (1H, s), 7.32 (2H, s), 8.47 (2H, s);
Mass spectrum (ESI): 391 (M+H)

Compound 28

2-[4-(piperidin-1-yl)piperidin-1-yl]-5-(2-naphthyl)pyrimidine

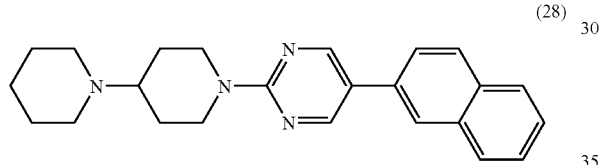

(28)

The entitled compound was obtained by reacting 5-bromo-2-{4-(piperidin-1-yl)piperidin-1-yl}pyrimidine that has been obtained in the production process for the compound 24, with naphtalene-2-boronic acid.

$^1$H NMR (300 MHz, CDCl$_3$, δ ppm): 1.40-1.67 (8H, m), 1.89-2.01 (2H, m), 2.50-2.63 (5H, m), 2.86-2.98 (2H, m), 4.85-4.95 (2H, m), 7.43-7.54 (2H, m), 7.58-7.65 (1H, m), 7.83-7.95 (4H, m), 8.67 (2H, s);
Mass spectrum (ESI): 373 (M+H)

Compound 29

2-[4-(piperidin-1-yl)piperidin-1-yl]-5-[4-(pyrrolidin-1-ylcarbonyl)phenyl]pyrimidine

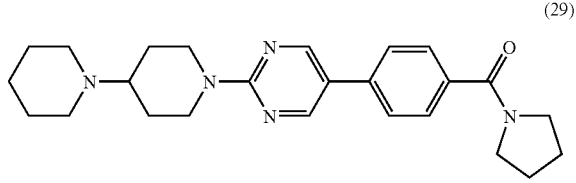

(29)

The entitled compound was obtained by reacting 5-bromo-2-{4-(piperidin-1-yl)piperidin-1-yl}pyrimidine that has been obtained in the production process for the compound 24, with 4-(pyrrolidine-1-carbonyl)phenylboric acid.

$^1$H NMR (300 MHz, CDCl$_3$, δ ppm): 1.38-1.75 (9H, m), 1.83-2.04 (6H, m), 2.46-2.63 (4H, m), 2.83-2.97 (2H, m), 3.43-3.52 (2H, m), 3.62-3.71 (2H, m), 4.82-4.93 (2H, m), 7.49 (2H, d, J=8.3 Hz), 7.60 (2H, d, J=8.3 Hz), 8.55 (2H, s);
Mass spectrum (ESI): 420 (M+H)

Compound 30

1-[4-(piperidin-1-yl)piperidin-1-yl]-4-(3-pyridyl)benzene

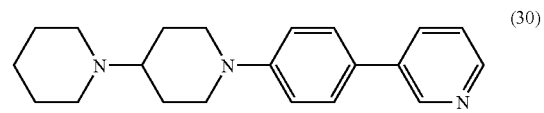

(30)

The entitled compound was obtained by reacting 4-[4-(piperidin-1-yl)piperidin-1-yl]-bromobenzene and pyridine-3-boric acid. 4-[4-(Piperidin-1-yl)piperidin-1-yl]-bromobenzene was produced in the same production method as that for 5-bromo-2-[(4-piperidin-1-yl)piperidin-1-yl]pyrimidine produced in Example 24, or according to the method, or in combination of the method with an ordinary method.

$^1$H NMR (300 MHz, CDCl$_3$, δ ppm): 1.49-2.04 (9H, m), 2.61-2.84 (8H, m), 3.83-3.87 (2H, m), 7.01 (2H, d, J=8.5 Hz), 7.26-7.34 (1H, m), 7.49 (2H, d, J=8.4 Hz), 7.81-7.84 (1H, m), 8.51 (1H, d, J=3.8 Hz), 8.81 (1H, d, J=2.3 Hz);
Mass spectrum (ESI): 322 (M+H)

Compound 31

1-(Piperidin-1-ylmethyl)-4-[4-(piperidin-1-yl)piperidin-1-yl]benzene dihydrochloride

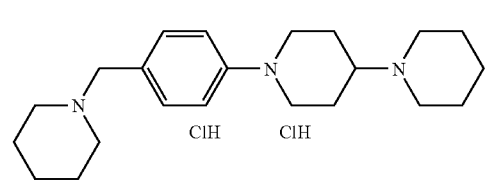

(31)

The compound was obtained by reducing the compound 19 with lithiumaluminium hydride in an ordinary method.

$^1$H NMR (400 Hz, DMSO-d$_6$, δ ppm): 1.20-2.10 (16H, m), 2.10-2.30 (2H, m), 2.62-3.00 (6H, m), 3.10-3.50 (5H, m), 3.70-4.42 (2H, m), 7.03 (2H, d, J=8.8 Hz), 7.40 (2H, d, J=8.8 Hz);
Mass spectrum (ESI): 342 (M+H)

Reference Example

4-{4-(Piperidin-1-yl)piperidin-1-yl}benzoic acid hydrochloride

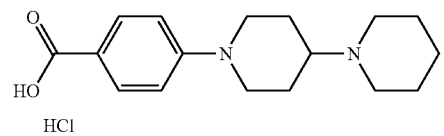

1) Production of 4-[(4-piperidin-1-yl)piperidin-1-yl]benzonitrile:

Potassium carbonate (4.14 g, 30 mmols) and (4-piperidin-1-yl)piperidine (6.05 g, 36 mmols) were added to dimethylsulfoxide solution (10 ml) of 4-fluorobenzonitrile (3.63 g, 30 mmols), and stirred at 95° C. for 3 hours. The reaction mixture was cooled to room temperature, and poured into ice-water (300 ml) and stirred. The insoluble matter formed was taken out through filtration, and dried to obtain the entitled compound (6.35 g, 81%).

2) Concentrated hydrochloric acid (10 ml) was added to 4-[(4-piperidin-1-yl)piperidin-1-yl]benzonitrile (3.81 g, 14.1 mmols), and stirred at 130° C. for 3 hours. The reaction mixture was concentrated under reduced pressure. The residue was taken out through filtration, washed with methanol/chloroform (2/1), and then dried to obtain the entitled compound (4.23 g, 92%).

Preparation of Pharmaceutical Compositions

Formulation Example 1

10 parts of the compound of Example 1, 15 parts of heavy magnesium oxide and 75 parts of lactose were uniformly mixed to prepare a powdery or granular preparation having a particle size of at most 350 µm. The preparation is encapsulated to give capsules.

Formulation Example 2

45 parts of the compound of Production Example 1, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 µm.

Formulation Example 3

A granular preparation was prepared in the same manner as in Formulation Example 2. 96 parts of the granular preparation is mixed with 3 parts of calcium stearate, and shaped under compression into tablets having a diameter of 10 mm.

Formulation Example 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

Example 2

Pharmaceutical Test

The usefulness of the histamine-H3 receptor antagonist containing a piperidine derivative of formula (I) of the invention as medicines was proven by the following pharmaceutical test examples.

Pharmaceutical Test Example 1

Histamine Analogue-Binding Inhibition Test

A cDNA sequence coding for a human histamine-H3 receptor [see International Laid-Open WO00/39164) was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see *Proceedings of the National Academy of Sciences of the United States of America*, Vol., 84, p. 7413 (1987)] to obtain histamine-H3 receptor expression cells.

A membrane specimen prepared from the cells having expressed a histamine-3 receptor was incubated in an assay buffer (50 mM Tris buffer, pH 7.4) along with a test compound and 20,000 cpm of [$^3$H]N$^a$-methylhistamine (by NEN) therein at 25° C. for 2 hours, and then filtered through a glass filter GF/C. This was washed with 50 mM Tris buffer (pH 7.4), and the radioactivity on the glass filter was measured. The non-specific binding was determined in the presence of 10 µM thioperamide (by Sigma), and the 50% inhibitory concentration (IC$_{50}$) of the test compound to specific N$^a$-methylhistamine binding was calculated [see *Molecular Pharmacology*, Vol. 55, p. 1101 (1999)].

Pharmaceutical Test Example 2

Histamine Analogue-Binding Inhibition Test

A membrane specimen prepared from the cells having expressed a histamine-H3 receptor was incubated in an assay buffer (50 mM Tris buffer, 100 mM NaCl, 5 mM MgCl$_2$, pH 7.4) along with a test compound, 20 nM R-methylhistamine (histamine analogue, by Sigma), 10 mM GDP (guanine-nucleotide diphosphate, by Sigma), 200 pM [$^{35}$S] GTPγS (guanine-nucleotide triphosphate analogue, by Amersham) and SPA resin (wheat germ agglutinin SPA beads, by Amersham) therein on a 96-well optiplate (by Packard) at 25° C. for 3 hours and then centrifuged at 3,000 rpm, and its activity was counted with Topcount (by Packard). The non-specific binding was determined in the presence of 10 µM GTPγS (by Sigma), and the 50% inhibitory concentration (IC$_{50}$) of the test compound to specific [$^{35}$S] GTPγS binding was calculated [see *British Journal of Pharmacology*, Vol. 135, p. 383 (2002)].

The results of Pharmaceutical Test Examples 1 and 2 are shown in Table 6.

TABLE 6

| Compound | GTP g S IC50 | Binding IC50 |
|---|---|---|
| 1 ![structure with H3C—N piperidine—N(CH3)—C(=O)—phenyl—N piperidine—N piperidine] | | 19 |
| 2 ![structure with H3C—N piperidine—NH—C(=O)—phenyl—N piperidine—N piperidine] | | 200 |

TABLE 6-continued

| Compound | | GTP g S IC50 | Binding IC50 |
|---|---|---|---|
| 3 | ![structure] | | 29 |
| 4 | ![structure] | | 18 |
| 5 | ![structure] | | 36 |
| 6 | ![structure] | | 14 |
| 7 | ![structure] | 1.1 | 7.5 |
| 8 | ![structure] | | 14 |
| 9 | ![structure] | | 31 |
| 10 | ![structure] | | 79 |

TABLE 6-continued

| Compound | GTP g S IC50 | Binding IC50 |
|---|---|---|
| 11 | | 230 |
| 12 | 87 | |
| 13 | 19 | |
| 14 | 64 | |
| 15 | 9.2 | |
| 16 | 16 | |
| 17 | 26 | |

TABLE 6-continued

| Compound | | GTP g S IC50 | Binding IC50 |
|---|---|---|---|
| 18 | [structure] | 24 | |
| 19 | [structure] | | 420 |
| 20 | [structure] | | 660 |
| 21 | [structure] | | 2400 |
| 22 | [structure] | | 180 |
| 23 | [structure] | | 670 |
| 24 | [structure] | | 61 |
| 25 | [structure] | | 160 |
| 26 | [structure] | | 2200 |

TABLE 6-continued

| Compound | | GTP g S IC50 | Binding IC50 |
|---|---|---|---|
| 27 | | | 1700 |
| 28 | | | 1700 |
| 29 | | | 96 |
| 30 | | | 70 |
| 31 | | | 31 |
| 32 | | | 67 |
| 33 | | | 42 |
| 34 | | | 38 |
| 35 | | | 66 |

TABLE 6-continued

| Compound | GTP g S IC50 | Binding IC50 |
|---|---|---|
| 36 | | 87 |
| 37 | | 31 |
| 38 | | 100 |
| 39 | | 78 |
| 40 | | 11 |

As is obvious from the results, the piperidine derivatives strongly inhibited the binding of $N^a$-methylhistamine histamine analogue) to histamine-H3 receptor.

INDUSTRIAL APPLICABILITY

The novel piperidine derivatives of the invention significantly inhibits the binding of Nα-methylhistamine (histamine analogue) to histamine-H3 receptor-expressing cells, and they effectively act as a histamine-H3 receptor antagonist or inverse-antagonist, and significantly inhibit the in-vitro action of R-α-methylhistamine (selective agonist). The derivatives are effective as preventives or remedies for metabolic system diseases such as obesity, diabetes, hormone secretion disorder, hyperlipemia, gout, fatty liver, circulatory system diseases, for example, stenocardia, acute/congestive cardiac insufficiency, cardiac infarction, coronary arteriosclerosis, hypertension, nephropathy, sleep disorder and various diseases accompanied by sleep disorder such as idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night worker sleep insanitation, idiopathic insomnia, repetitive insomnia, true insomnia, electrolyte metabolism disorder, and central and peripheral nervous system diseases such as bulimia, emotional disorder, melancholia, anxiety, epilepsy, delirium, dementia, shinzophrenia, attention deficit/hyperactivity disorder, memory disorder, Alzheimer's disease, Parkinson's disease, sleep disorder, recognition disorder, motion disorder, paresthesia, dysosmia, epilepsy, morphine resistance, narcotic dependency, alcoholic dependency.

The invention claimed is:

1. A compound of the formula (I):

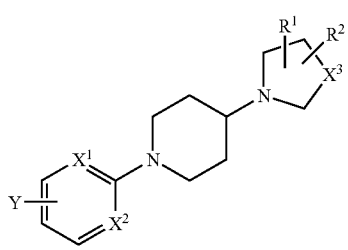

wherein:
$X^1$ represents a nitrogen atom;
$X^2$ represents a nitrogen atom;
$X^3$ represents $-O_s-(CH_2)_m-$, wherein s indicates 0 or 1, and m indicates an integer to make (m+s)=0, 1, 2, 3 or 4;
$R^1$ and $R^2$ independently represent a hydrogen atom, a halogen atom, a linear or branched lower alkyl group, a lower alkoxy group, or an acetyl group substituted with 2 or 3 fluorine atoms;
Y represents a phenyl group, a naphthyl group or a pyridyl group, which is unsubstituted or substituted with a substituent selected from a group consisting of a cyano group, a hydroxyl group, a lower alkyl group (the lower alkyl group may be further substituted with a hydroxyl group, a halogen atom, an amino group, an aryl group or a heteroaryl group), a cycloalkyl group, a lower alkoxy group (the lower alkoxy group may be further substituted with a halogen atom), a halogen atom, a mono-lower alkylcarbamoyl group, a di-lower alkylcarbamoyl group, a carbamoyl group, a cycloalkyliminocarbamoyl group, a lactam ring, a trifluoromethyl group, a mono-lower alkylamino group, a di-lower alkylamino group and an alkanoyl group;
or a pharmaceutically-acceptable salt thereof.

2. The compound of claim 1, wherein $R^1$ and $R^2$ are hydrogen atoms, $X^3$ is $-O_s-(CH_2)_m-$, wherein s is 0 and m is an integer which is 1, 2 or 3.

3. The compound of claim 2, wherein $X^3$ is $-O_s-(CH_2)_m-$, wherein s is 0 and m is an integer which is 2, to form a piperidinyl group.

4. The compound of claim 1, wherein Y is a phenyl group which is unsubstituted or substituted with 1 or 2 substituents selected from a group consisting of a cyano group, a trifluoromethyl group, a halogen atom and pyrrolidin-1-ylcarbonyl group.

5. The compound of claim 1, wherein in Y is a pyridyl group.

6. The compound of claim 1, wherein in Y is a naphthyl group.

7. A compound which is selected from the group consisting of:
2-[(4-piperidin-1-yl)piperidin-1-yl]-5-(4-cyanophenyl)pyrimidine,
2-[(4-piperidin-1-yl)piperidin-1-yl]-5-(3-pyridyl)pyrimidine,
2-[4-(piperidin-1-yl)piperidin-1-yl]-5-(3-trifluoromethylphenyl)pyrimidine,
2-[4-(piperidin-1-yl)piperidin-1-yl]-5-(3,5-dichlorophenyl)pyrimidine,
2-[4-(piperidin-1-yl)piperidin-1-yl]-5-(2-naphthyl)pyrimidine, and
2-[4-(piperidin-1-yl)piperidin-1-yl]-5-[4-(pyrrolidin-1-ylcarbonyl)phenyl]pyrimidine,
or a pharmaceutically-acceptable salt thereof.

8. A pharmaceutical composition which comprises an inert carrier and the compound of claim 1, or a pharmaceutically acceptable salt thereof.

9. A pharmaceutical composition which comprises an inert carrier and the compound of claim 7, or a pharmaceutically acceptable salt thereof.

* * * * *